(12) United States Patent
Hogg

(10) Patent No.: US 11,526,182 B2
(45) Date of Patent: Dec. 13, 2022

(54) SENSING AND OPERATION OF DEVICES IN VISCOUS FLOW USING DERIVED PARAMETERS TO REDUCE DATA-HANDLING REQUIREMENTS

(71) Applicant: CBN Nano Technologies Inc., Ottawa (CA)

(72) Inventor: Tad Hogg, Mountain View, CA (US)

(73) Assignee: CBN Nano Technologies Inc., Ottawa (CA)

( * ) Notice: Subject to any disclaimer, the term of this patent is extended or adjusted under 35 U.S.C. 154(b) by 930 days.

(21) Appl. No.: 16/363,492

(22) Filed: Mar. 25, 2019

(65) Prior Publication Data
US 2020/0310471 A1    Oct. 1, 2020

(51) Int. Cl.
| G01L 15/00 | (2006.01) |
| G05D 7/06 | (2006.01) |
| A61B 5/00 | (2006.01) |
| G01B 13/16 | (2006.01) |
| A61B 1/00 | (2006.01) |

(52) U.S. Cl.
CPC ......... *G05D 7/0676* (2013.01); *A61B 5/6861* (2013.01); *G01B 13/16* (2013.01); *G01L 15/00* (2013.01); *A61B 1/00156* (2013.01)

(58) Field of Classification Search
None
See application file for complete search history.

(56) References Cited

U.S. PATENT DOCUMENTS

| 5,065,628 A | 11/1991 | Benecke |
| 5,525,882 A | 6/1996 | Asaka et al. |
| 5,559,696 A | 9/1996 | Borenstein |
| 6,931,952 B2 | 8/2005 | Rantala et al. |
| 7,082,350 B2 | 7/2006 | Skoog |
| 7,517,695 B2* | 4/2009 | Haidekker ............. G01N 11/14 422/82.07 |
| 7,670,844 B2* | 3/2010 | Haidekker ............. G01N 11/14 422/50 |
| 7,943,390 B2 | 5/2011 | Haidekker et al. |

(Continued)

FOREIGN PATENT DOCUMENTS

CA    3038104    8/2022

OTHER PUBLICATIONS

Akers. A Molecular Rotor as Viscosity Sensor in Aqueous Colloid Solutions. *Journal of Biomechanical Engineering.* (2004) vol. 126, pp. 340-345.

(Continued)

*Primary Examiner* — Lisa M Caputo
*Assistant Examiner* — Nigel H Plumb

(57) ABSTRACT

Devices, including robotic devices, operating in viscous fluid flow can use passive sensor data collected to represent fluid parameters at an instant in time to derive information about the flow, the motion and position of the device, and parameters of the physical system constraining the flow. Using quasi-static analysis techniques, and appropriate feature selection for machine learning, very accurate determinations can be made, generally in real time, with very modest computational requirements. These determinations can then be used to map systems, navigate devices through a system, or otherwise control the actions of, e.g., robotic devices for clean-up, leak detection, or other functions.

42 Claims, 23 Drawing Sheets

(56) References Cited

U.S. PATENT DOCUMENTS

| | | | | |
|---|---|---|---|---|
| 8,505,388 | B2* | 8/2013 | Mason | G01M 5/005 |
| | | | | 73/826 |
| 8,712,588 | B2* | 4/2014 | Myeong | G05D 1/0255 |
| | | | | 901/46 |
| 8,743,659 | B1 | 6/2014 | Hogg et al. | |
| 8,743,660 | B1* | 6/2014 | Hogg | H04B 1/1027 |
| | | | | 367/137 |
| 8,755,252 | B1 | 6/2014 | Hogg et al. | |
| 8,760,972 | B1 | 6/2014 | Hogg et al. | |
| 8,787,115 | B1 | 7/2014 | Hogg et al. | |
| 8,830,091 | B2* | 9/2014 | Karlsson | G06T 7/55 |
| | | | | 340/988 |
| 8,837,258 | B1 | 9/2014 | Hogg et al. | |
| 9,218,003 | B2 | 12/2015 | Fong et al. | |
| 9,400,501 | B2 | 7/2016 | Schnittman | |
| 9,481,460 | B1* | 11/2016 | Kozloski | B64D 1/22 |
| 9,886,037 | B2 | 2/2018 | Karlsson et al. | |
| 9,895,808 | B2* | 2/2018 | Stout | B25J 5/007 |
| 9,910,444 | B2* | 3/2018 | Eade | G06K 9/6201 |
| 9,952,053 | B2 | 4/2018 | Fong et al. | |
| 10,024,950 | B1* | 7/2018 | Hogg | G01S 1/72 |
| 2005/0076724 | A1 | 4/2005 | Boudreaux | |
| 2017/0192748 | A1 | 7/2017 | Merkle et al. | |

OTHER PUBLICATIONS

Augustin & Koh. Organotypic vasculature: From descriptive heterogeneity to functional pathophysiology. *Science*. (2017) vol. 357, pp. eaal2379.

Bleckmann & Zelick. Lateral line system of fish. *Integrative Zoology*. (2009) vol. 4, pp. 13-25.

Chambers et al. A fish perspective: detecting flow features while moving using an artificial lateral line in steady and unsteady flow. *J R Soc Interface*. (2014), Aug. 1, 2014 ed., vol. 11, pp. 13.

Dusenbery. Living at Micro Scale: the Unexpected Physics of Being Small. (2009), pp. 254-257. Cambridge, MA: Harvard University Press.

Eswaran & Malarvizhi. MEMS Capacitive Pressure Sensors: A Review on Recent Development and Prospective. *International Journal of Engineering and Technology*. (2013).

R. Freitas. Nanomedicine, vol. I: Basic Capabilities. (1999), pp. 93-122, 209-274. Landes Bioscience.

Grosse & Schroder. The Micro-Pillar Shear-Stress Sensor MPS(3) for Turbulent Flow. *Sensors*. (2009) vol. 9, pp. 2222-2251.

Haidekker, Akers, Lichlyter, Brady, & Theodorakis. Sensing of Flow and Shear Stress Using Fluorescent Molecular Rotors. *Sensor Letters*. (2005) vol. 3, pp. 42-48.

Herrera-May, Aguilera-Cortes, Garcia-Ramirez, & Manjarrez. Resonant Magnetic Field Sensors Based on MEMS Technology. *Sensors (Basel)*. (2009), Jan. 1, 2009 ed., vol. 9, pp. 7785-7813.

Hogg. Stress-based navigation for microscopic robots in viscous fluids. *Journal of Micro-Bio-Robotics*. (2018).

Hogg. Identifying Vessel Branching from Fluid Stresses on Microscopic Robots. (2018).

Hogg. Coordinating microscopic robots in viscous fluids. *Autonomous Agents and Multi-Agent Systems*. (2006) vol. 14, pp. 271-305.

Hogg. Using surface-motions for locomotion of microscopic robots in viscous fluids. *J. of Micro-Bio Robotics*. (2014) vol. 9, pp. 61-77.

Hogg & Freitas. Acoustic communication for medical nanorobots. *Nano Communication Networks*. (2012).

Jain, Martin, & Stylianopoulos. The role of mechanical forces in tumor growth and therapy. *Annu Rev Biomed Eng.* (2014) vol. 16, pp. 321-346.

Kantsler, Dunkel, Blayney, & Goldstein. Rheotaxis facilitates upstream navigation of mammalian sperm cells. *eLife*. (2014) pp. 1-12.

Karimi, Yazdi, & Ardekani. Hydrodynamic mechanisms of cell and particle trapping in microfluidics. *Biomicrofluidics*. (2013) vol. 7, pp. 21501.

Koka & Sodano. High-sensitivity accelerometer composed of ultralong vertically aligned barium titanate nanowire arrays. *Nat Commun*. (2013), Nov. 2, 2013 ed., vol. 4, pp. 2682.

Li, Esteban-Fernandez, Gao, Zhang, & Wang. Micro/nanorobots for biomedicine: Delivery, surgery, sensing, and detoxification. *Science Robotics*. (2017) vol. 2, pp. 2:eaam6431.

Liu, Wang, Wang, & Liu. A Review of Artificial Lateral Line in Sensor Fabrication and Bionic Applications for Robot Fish. *Appl Bionics Biomech*. (2016), Jan. 25, 2017 ed., vol. 2016, pp. 6.

Lofdahl & Gad-El-Hak. MEMS-based pressure and shear stress sensors for turbulent flows. *Meas. Sci. Technol*. (1999) vol. 10, pp. 665-686.

Lutz et al. Wall Shear Stress Distribution in a Model Canine Artery during Steady Flow. *Circulation Research*. (1977) vol. 41, pp. 391-399.

Martel & Toner. Inertial focusing in microfluidics. *Annu Rev Biomed Eng*. (2014) vol. 16, pp. 371-396.

Martin et al. Complex fluids under microflow probed by SAXS: rapid microfabrication and analysis. *Journal of Physics: Conference Series*. (2010) vol. 247, pp. 012050.

Merkle et al. Molecular Mechanical Computing Systems. (2016). Institute for Molecular Manufacturing.

Merkle et al. Mechanical computing systems using only links and rotary joints. *ASME Journal on Mechanisms and Robotics*. (2018) vol. 10, pp. 061006.

Middlemiss et al. Field Tests of a Portable MEMS Gravimeter. *Sensors (Basel)*. (2017), Nov. 9, 2017 ed., vol. 17.

Murray. The physiological principle of minimum work: I. The vascular system and the cost of blood volume. *Proceedings of the National Academy of Sciences USA*. (1926) vol. 12, pp. 207-214.

Mustafic, Huang, Theodorakis, & Haidekker. Imaging of flow patterns with fluorescent molecular rotors. *J Fluoresc*. (2010) vol. 20, pp. 1087-1098.

Nagy, Chang, Dvorak, & Dvorak. Why are tumour blood vessels abnormal and why is it important to know? *British J. of Cancer*. (2009) vol. 100, pp. 865-869.

Pawlik, Rackl, & Bing. Quantitative capillary topography and blood flow in the cerebral cortex of cats: an in vivo microscopic study. *Brain Research*. (1981) vol. 208, pp. 35-58.

Petersson, Aberg, Sward-Nilsson, & Laurell. Free Flow Acoustophoresis: Microfluidic-Based Mode of Particle and Cell Separation. *Anal. Chem*. (2007) vol. 79, pp. 5117-5123.

Pillapakkam, Barbier, & Humphrey. Experimental and numerical investigation of a fish artifical lateral line canal. *Fifth International Symposium on Turbulence and Shear Flow Phenomena*. (2007).

Purcell. Life at low Reynolds number. *American J. of Physics*. (1977) pp. 3-11.

Secomb, Hsu, & Pries. Motion of red blood cells in a capillary with an endothelial surface layer: effect of flow velocity. *American J. of Physiology: Heart and Circulatory Physiology*. (2001) vol. 281, pp. H629-H636.

Sharp, Adrian, Santiago, & Molho. Liquid Flows in Microchannels. M. Gad-el-Hak (Ed.), *MEMS Introduction and Fundamentals*. (2005) pp. 10-11 to 10-45: CRC Press.

Sochi. Fluid flow at branching junctions. *International Jounral of Fluid Mechanics Research*. (2015) pp. 59-81.

Soundararajan et al. MEMS shear stress sensors for microcirculation. *Sensors and Actuators A: Physical*. (2005) vol. 118, pp. 25-32.

Tang et al. Design and simulation of artificial fish lateral line. *International Journal of Advanced Robotic Systems*. (2019) vol. 16, pp. 15.

Turduev, Cabrita, Kirtay, Gazi, & Marques. Experimental studies on chemical concentration map building by a multi-robot system using bio-inspired algorithms. *Autonomous Agents and Multi-Agent Systems*. (2012), Dec. 14, 2012 ed., vol. 28, pp. 72-100.

Varma, Hou, Han, & Voldman. A Cell-based Sensor of Fluid Shear Stress for Microfluidics. *17th International Conference on Miniaturized Systems for Chemistry and Life Sciences*. (2013) pp. 1644-1646. Freiburg, Germany.

Vollmayr. Snookie: an autonomous underwater vehicle with artificial lateralline system. *Flow Sensing in Air and Water*. (2014) pp. 521-562: Springer.

(56) References Cited

OTHER PUBLICATIONS

Wang et al. MEMS-based gas flow sensors. *Microfluidics and Nanofluidics.* (2009) vol. 6, pp. 333-346.

Wu, Day, & Gu. Shear stress mapping in microfluidic devices by optical tweezers. *Optics Express.* (2010) vol. 18, pp. 7611-7616.

Xie & Fedder. Fabrication, characterization, and analysis of a DRIE CMOS-MEMS gyroscope. *IEEE Sensors Journal.* (2003) vol. 3, pp. 622-631.

Yang et al. Distant touch hydrodynamic imaging with an artificial lateral line. *Proceedings of the National Academy of Sciences USA.* (2006) vol. 103, pp. 18891-18895.

Zhang et al. Red-Emitting Mitochondrial Probe with Ultrahigh Signal-to-Noise Ratio Enables High-Fidelity Fluorescent Images in Two-Photon Microscopy. *Anal Chem.* (2015) vol. 87, pp. 12088-12095.

Zou, Liu, Chen, Cardenas-Jiron, & Schulten. Flow-induced beta-hairpin folding of the glycoprotein Ibalpha beta-switch. *Biophys J.* (2010) vol. 99, pp. 1182-1191.

\* cited by examiner

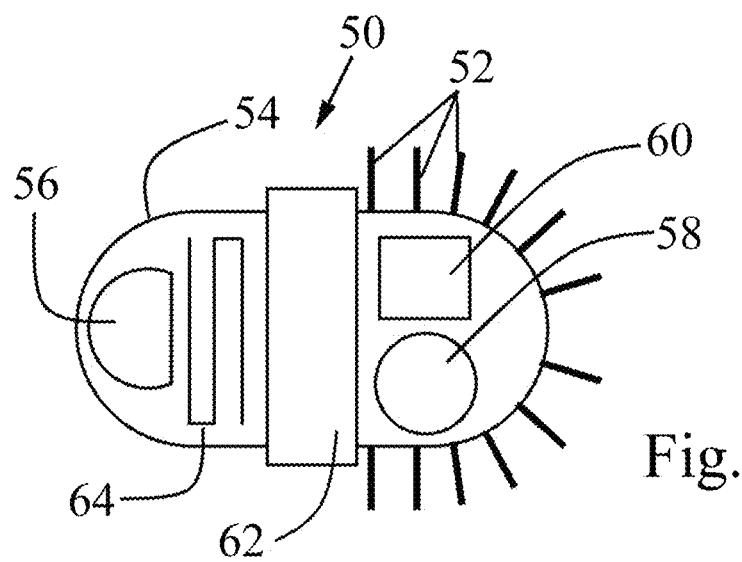
Fig. 1
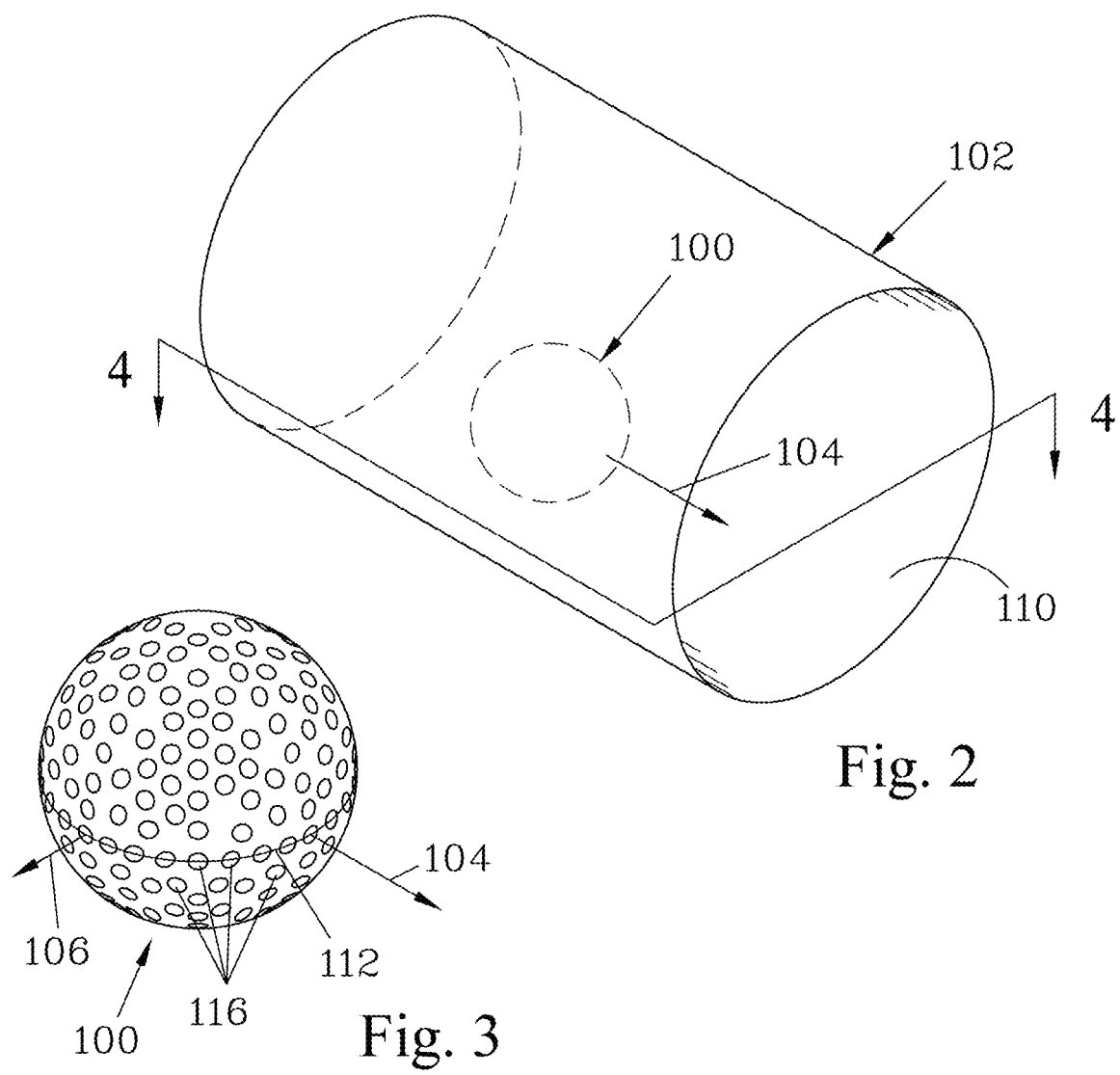
Fig. 2
Fig. 3

SENSING AND OPERATION OF DEVICES IN VISCOUS FLOW USING DERIVED PARAMETERS TO REDUCE DATA-HANDLING REQUIREMENTS

CROSS-REFERENCE TO RELATED APPLICATIONS

Not applicable.

FEDERALLY SPONSORED RESEARCH

Not applicable.

SEQUENCE LISTING OR PROGRAM

Not applicable.

FIELD OF INVENTION

The present invention is directed to improvements in the decisions and operations of devices, including robots, in viscous fluid, at least partially through efficient analysis of instantaneous data collected via passive sensors.

BACKGROUND

Fluid Flow Analysis and Applications

Fluid flow is important to multiple fields of technology and may be characterized for many reasons, including an interest in the fluid flow itself, or an interest the effects of the fluid flow (e.g., exerting forces on an object). To analyze fluid flow, various sensors may be used, and dyes or particles can help visualize flow patterns. Some of these sensors are microscopic or molecular in size. (Grosse and Schroder, "The Micro-Pillar Shear-Stress Sensor MPS(3) for Turbulent Flow," Sensors, 2009; Martin, Brooks et al., "Complex fluids under microflow probed by SAXS: rapid microfabrication and analysis," Journal of Physics: Conference Series, 2010; Mustafic, Huang et al., "Imaging of flow patterns with fluorescent molecular rotors," J Fluoresc, 2010).

Fluid flow can have biological effects. For example, fluid flow is known to affect gene expression (Zou, Liu et al., "Flow-induced beta-hairpin folding of the glycoprotein lbalpha beta-switch," Biophys J, 2010), and cells that fluoresce when subjected to shear stress have been created for use as sensors (Varma, Hou et al., "A Cell-based Sensor of Fluid Shear Stress for Microfluidics," 17th International Conference on Miniaturized Systems for Chemistry and Life Sciences, Freiburg, Germany, 2013). Shear force is also believed to affect the vasculature (LUTZ, CANNON et al., "Wall Shear Stress Distribution in a Model Canine Artery during Steady Flow," Circulation Research, 1977). Rheotaxis (navigation by facing into an oncoming current) in cells has also been studied (Kantsler, Dunkel et al., "Rheotaxis facilitates upstream navigation of mammalian sperm cells," eLife, 2014).

Fluid forces can be used for particle handling. Such techniques include inertial focusing, and can be used to position objects within a fluid (e.g., microspheres or cells in microfluidics systems) into specific bins for sorting, or otherwise position the objects (e.g., for analysis in a lab-on-a-chip or assay scenario). (Sharp, Adrian et al., "Liquid Flows in Microchannels," MEMS Introduction and Fundamentals, CRC Press, 2005; Petersson, Aberg et al., "Free Flow Acoustophoresis: Microfluidic-Based Mode of Particle and Cell Separation," Anal. Chem., 2007; Karimi, Yazdi et al., "Hydrodynamic mechanisms of cell and particle trapping in microfluidics," Biomicrofluidics, 2013; Martel and Toner, "Inertial focusing in microfluidics," Annu Rev Biomed Eng, 2014)

Software for the simulation and analysis of fluid flow is freely and commercially available. For example, SOLIDWORKS (Waltham, Mass. USA) offers a "Flow Simulation" module, which performs computational fluid dynamics calculations. Autodesk's (San Rafael, Calif. USA) CFD software offers similar capabilities, as does COMSOL's (Burlington, Mass. USA) CFD (Computational Fluid Dynamics) and FSI (Fluid Structure Interaction) modules. OpenFOAM (openfoam.com) is an open source computational fluid dynamics package. More general tools, such as Mathematica (Wolfram Research, Champaign, Ill. USA) and MATLAB (MathWorks, Natick, Mass. USA), can also be used, and statistical analysis of results can be done via many software packages, including some of those already listed, and the free R (r-project.org). These lists are only exemplary; many other packages are available, and custom software could also be used.

Computing means which can be used include conventional CPUs, GPUs (graphical processing units), FPGAs (field-programmable gate arrays), ASICs (application-specific integrated circuits), mechanical computers, embedded microprocessors (in which we include microcontrollers), and application-specific mechanical devices (for example, a device similar to a mechanical odometer could be used to register sensor counts, time, or other quantities, and such a device, being optimized for a single purpose, can be smaller and more efficient than general purpose computational devices). For convenience, we may refer to all such computational means or devices as a "CPU".

For many analysis techniques, such as FEA (finite element analysis) or FEM (finite element method), memory (e.g., RAM, or other memory or data storage means) size and memory bandwidth to one or more processors can be more limiting than CPU speed. The storage space required for the model itself is generally not a problem, and models themselves can be stored on CD, DVD, thumb drives, hard drives, or other data storage means. However, the memory required to analyze a given model can be problematically-large because memory requirements increase as degrees of freedom increase. Models with many elements or degrees of freedom may require memory beyond the capacity of, e.g., the average personal computer. Although virtual memory can be used, this substantially slows down the computations.

In general, solving fluid dynamics models in real-time or near real-time may be challenging or even impossible, depending on factors such as the hardware used, the available power (e.g., the same hardware may be run at different frequencies depending on available power and cooling), model complexity, computations required and algorithms used, and acceptable delay.

Rheological Sensors

Rheological sensors can aid in measuring properties of fluid flow, and such sensors be anywhere from macroscopic, to micron-scale (e.g., MEMS-based) or molecular-scale, and can measure flow, viscosity, velocity, shear and pressure (both of which are components of stress, and could be measured with a single type of sensor if desired), temperature, and other quantities (Lofdahl and Gad-el-Hak, "MEMS-based pressure and shear stress sensors for turbulent flows," Meas. Sci. Technol., 1999; Akers, "A Molecular Rotor as Viscosity Sensor in Aqueous Colloid Solutions," Journal of Biomechanical Engineering, 2004; Haidekker, Akers et al., "Sensing of Flow and Shear Stress Using Fluorescent Molecular Rotors," Sensor Letters, 2005; Soundararajan, Rouhanizadeh et al., "MEMS shear stress sensors for microcirculation," Sensors and Actuators A: Physical, 2005; Grosse and Schroder, "The Micro-Pillar Shear-Stress Sensor MPS(3) for Turbulent Flow," Sensors, 2009; Haidekker, "Local flow and shear stress sensor based on molecular rotors," US7517695, 2009; Wang, Chen et al., "MEMS-based gas flow sensors," Microfluidics and Nanofluidics, 2009; Haidekker, Grant et al., "Supported molecular biolfluid viscosity sensors for invitro and in vivo use," US7670844, 2010; Mustafic, Huang et al., "Imaging of flow patterns with fluorescent molecular rotors," J Fluoresc, 2010; Wu, Day et al., "Shear stress mapping in microfluidic devices by optical tweezers," OPTICS EXPRESS, 2010; Haidekker, Grant et al., "Supported molecular biofluid viscosity sensors for in vitro and in vivo use," US7943390, 2011; Eswaran and Malarvizhi, "MEMS Capacitive Pressure Sensors: A Review on Recent Development and Prospective," International Journal of Engineering and Technology, 2013; Zhang, Sun et al., "Red-Emitting Mitochondrial Probe with Ultrahigh Signal-to-Noise Ratio Enables High-Fidelity Fluorescent Images in Two-Photon Microscopy," Anal Chem, 2015).

Although not technically falling under rheological sensors, numerous types of other sensors exist that could provide additional data, such as gravity-based sensors, magnetic field sensors, angle sensors, and accelerometers. Such sensors, and many more, are well-known, but for examples see (Huikai and Fedder, "Fabrication, characterization, and analysis of a DRIE CMOS-MEMS gyroscope," IEEE Sensors Journal, 5, 2003; Herrera-May, Aguilera-Cortes et al., "Resonant Magnetic Field Sensors Based On MEMS Technology," Sensors (Basel), 10, 2009; Koka and Sodano, "High-sensitivity accelerometer composed of ultra-long vertically aligned barium titanate nanowire arrays," Nat Commun, 2013; Middlemiss, Bramsiepe et al., "Field Tests of a Portable MEMS Gravimeter," Sensors (Basel), 11, 2017).

SUMMARY

The present application includes material from the present inventor's earlier publications (Hogg, "Stress-based navigation for microscopic robots in viscous fluids," Journal of Micro-Bio-Robotics, 2018; "Identifying Vessel Branching from Fluid Stresses on Microscopic Robots," 2018).

Techniques are disclosed for controlling the actions of a device (including robots) in fluid systems having viscous flow, based on passive sensing of fluid flow data (for example, pressure and shear forces), which may be analyzed using quasi-static methods and machine learning, to derive information relating to the position and/or movement of the device, other objects in the fluid, and features of the fluid systems such as information about the fluid flow itself, and the geometry of the fluid boundaries. Examples of information about the device itself include its position, orientation, and/or movement in the channel. Examples of information about the fluid system include fluid flow velocity, channel size, detection of features such as curves, branches, and merges, and/or the presence of additional objects in the channel besides the device in question, either static or moving. Time courses may be considered in that multiple measurements over time may be analyzed for trends (e.g., changes in the curvature of the vessel as the device moves through the fluid system—this is in some sense time dependent, but only because the device location changes with time, not because the flow is turbulent and cannot be understood in an instantaneous manner), but each of these measurements is still typically collected instantaneously and the measurements for a particular time are analyzed in a quasi-static manner.

This strategy allows for advantages including faster computation, reduced hardware requirements, and reduced sensor usage. These techniques provide information on the device and the fluid system that can be used to characterize the system, such as by mapping features of the fluid system (curves, bumps, branch points, merge points, areas where the flow indicates a possible leak, etc.) Maps of the fluid system may be created, and such maps or other models of the system can be used to direct devices to desired locations in the system. Information on the fluid system features can also be used to tell the devices when to take actions, such as navigating branch points, adhering to the channel walls, or removing deposits found on the walls.

BRIEF DESCRIPTION OF THE FIGURES

FIG. 1 is a schematic view of a device, illustrating various sensors, and power, communication, computation, and other mechanisms that could be incorporated.

FIG. 2 is a view of a spherical device operating in a cylindrical vessel, used for reference discussing examples of how surface stress measurements can be processed to obtain information on the device position and motion, and information on the geometry of the vessel.

FIG. 3 is a view of the spherical device shown in FIG. 2, illustrating an array of stress sensors distributed across the surface of the device. FIG. 3 also shows a direction of movement and direction to the nearest vessel wall for the situation shown in FIG. 2.

FIG. 6A illustrates the streamlines and fluid velocities with respect to the vessel, while FIG. 6B illustrates the streamlines and flow velocities with respect to the device.

FIG. 7A compares the normal and tangential stresses about the device at the locations of several sensors, while FIG. 7B compares the speed along the vessel and angular velocity for 2D and 3D cases, as the relative position of the device in the vessel is varied.

FIG. 19A is a plot comparing the actual and calculated angular velocity of the device, while FIG. 19B is a graph comparing the correlation between stress patterns separated by a short time interval.

FIG. 20A compares values for vessel diameter, FIG. 20B compares directions to the nearest point on the wall and direction of motion, FIG. 20C compares the distance from the device to the nearest wall, and FIG. 20D compares speed of the device along the vessel.

FIGS. 22A & 22B show the region 22-1 of FIG. 21A, while FIGS. 22C & 22D show the region 22-2 of FIG. 21B. Similarly to the representations for the straight vessel shown in FIGS. 6A and 6B, FIG. 22A shows fluid velocity with respect to the vessel and FIG. 22B shows fluid velocity with respect to the device, both for the branched vessel. FIG. 22C shows fluid velocity with respect to the vessel and FIG. 22D shows fluid velocity with respect to the device for the curved vessel.

FIG. 33 graphs the area under the curve of FIG. 28 for increasing percentages of signal noise in the sensors used to make the calculated parameters used for the classifier.

DETAILED DESCRIPTION

Terminology

Figure 4:
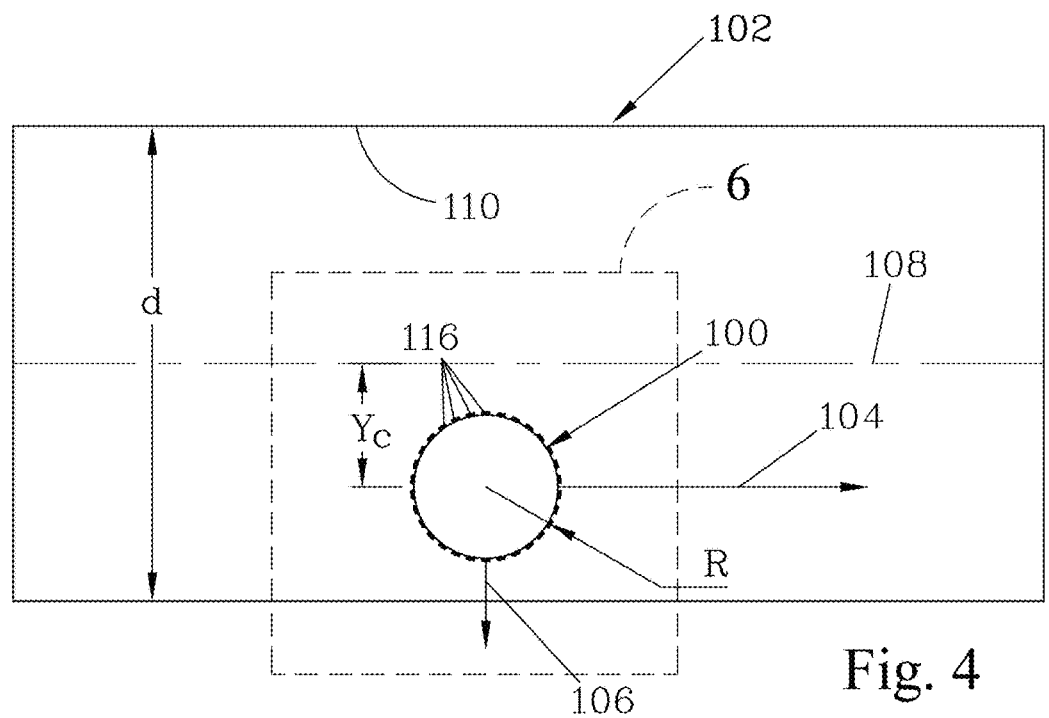
FIG. 4 is a view of the section 4-4 of FIG. 2, providing a 2-dimensional representation of the device and vessel. Region 6 shows the bounds of the area shown in greater detail in FIG. 6.

"Boundaries" are divisions between the fluid and objects adjacent to the fluid, surrounding the fluid, or within the fluid. Examples include the wall (or "channel," "vessel," or other appropriate term) surrounding a fluid a stationary object within the fluid, or a moving object within the fluid.

"Boundary layers" are transitions, often sharp transitions, of one or more properties (e.g., the velocity or vector of a fluid flow, or a chemical, thermal, or other gradient within the fluid) of a fluid flow. Boundary layers may be caused by the fluid flow itself (although at low Reynolds numbers, gradual transitions are the norm), or maybe caused by boundaries interrupting the natural flow of the fluid.

A "channel", unless context requires otherwise, is the boundary of a fluid system. Such a boundary may also be referred to as a wall or vessel, or any other term that conveys that it provides means for holding the fluid system in a particular shape (which shape is not necessarily static or rigid, though it may be). Specific examples may use terminology appropriate to the applicable field. For example, the fluid boundaries in an industrial system may be referred to as pipes, while in a biological context, they may be referred to as vasculature or capillaries.

"Features" of a fluid flow system include boundaries and their properties, fluid and its properties, fluid flow and its properties, and objects within the fluid and their properties. For example, features could include positions of boundaries holding the fluid, positions of objects within the fluid, characteristics of the fluid or fluid flow such as viscosity, velocity, direction, or the nature of any gradients present, such as gradients in temperature, velocity, or chemical concentrations. The term "feature" or "features" is also used in other contexts, such as using machine learning data-processing techniques to extract "features" from data. Context should make the intended meaning clear.

"Fluid flow system," "fluid system" or simply "system" when context makes the meaning clear, refers to any system of flowing fluid(s) (including gases) and any boundaries, including walls and other objects within the fluid. Examples include, but are not limited to, systems frequently containing water or other common solvents (e.g., microfluidics or "lab on a chip" systems), biological systems (e.g., blood flow within vasculature, lymph flow within lymphatic channels, or gas flow within lungs), and industrial systems (which may deal with highly-viscous materials, from oil, to foodstuffs such as peanut butter, honey, ketchup and sour cream, and which, as a result, may have viscous flow even at relatively large sizes, providing some cases where devices could be at least several inches in size).

"Harmonic analysis" includes any of various mathematical analysis techniques in which data are represented as the superposition of basic waveforms, including 2-dimensional and 3-dimensional Fourier transformations, spherical harmonic techniques, and other techniques known in the art.

"Instantaneous" measurement means without the need for continuous data collection or time-courses. No process is literally instant. For example, sensors take time, even if only fractions of a second, to gather data. Computing means take time to analyze the data. Data transmission takes time. So, by taking "snapshots" or "instantaneous" readings, we mean that as fast as the data representing a system having viscous flow can be gathered and analyzed, the desired inferences can be made. The distinction is that static or quasi-static systems can be analyzed "instantaneously," while time-dependent systems (which is almost all familiar everyday systems) cannot be, because even if nothing the natural flow of the fluid, the system can change over time due to turbulence.

"Machine learning" includes any appropriate mathematical operations or data analysis which allows the desired inferences or determinations to be made, including quantitative (e.g., velocity, viscosity) or qualitative (e.g., classification) analyses. Examples include Bayesian networks, classifiers, data mining, decision trees (and ensembles of decision frees such as random forests), deep learning, linear regression, logistic regression, neural networks, statistical analysis (descriptive and inferential), and wavelets. Pre- and post-processing of data, including averaging, noise reduction, normalization, Fourier transforms and many other techniques, is assumed to be inherent in machine learning and used as appropriate; such techniques are well-known. Machine learning may take place in real-time, or not, as necessary and convenient, and may be performed by computational means within a device inside a system, distributed among multiple devices in a system, offloaded to computational means outside the system, or a combination thereof. References to "inferences," "determinations," or other terms relating to the use of data to determine system properties, where contextually appropriate, are synonymous with machine learning. Machine learning is a well-developed field, with numerous publications and books on the subject. The following are but a small sampling of books on relevant topics in machine learning: (Everitt and Hothorn, "A Handbook of Statistical Analysis Using R, 2nd Edition," CRC Press, 2010; Bishop, "Pattern Recognition and Machine Learning (Information Science and Statistics)," Springer, 2011; Witten, Frank et al., "Data Mining, Practical Machine Learning Tools and Techniques, 3rd Edition," Burlington, Mass., Elsevier, 2011; Aster, Borchers et al., "Parameter Estimation and Inverse Problems, 2nd Edition," Academic Press, 2012; Mostafa, Ismail et al., "Learning From Data," AMLBook, 2012; Goodfellow, Bengio et al., "Deep Learning (Adaptive Computation and Machine Learning series)," MIT Press, 2016; Géron, "Hands-On Machine Learning with Scikit-Learn and TensorFlow: Concepts, Tools, and Techniques to Build Intelligent Systems," O'Reilly Media, 2017)

Features and Position in Fluid Systems

Fluid forces are routinely used to position objects within a fluid. The design problem to be solved in such cases might be stated as "An object within the fluid flow starts at position X, and needs to end up at position Y. How can the fluid flow be designed to make that happen?"

However, there is another position-related problem to be solved, and one which, to the best of our knowledge, has not been previously addressed for Stokes flow (aka, viscous flow) scenarios. This problem might be stated as "Given the ability to gather fluid-flow data, what information can be determined about the location, identity, and characteristics of system features?"

In addition to having different goals, the context of these two problems may be very different due to different levels of control (or lack thereof) over various aspects of the respective fluid flow systems. Diagnostic capabilities may differ greatly as well.

For example, in microfluidics systems or other systems designed for particle handling, the systems are designed to achieve some goal (e.g., move an object from point X to point Y). In order to do this, the designer of the system has, within the limits of manufacturability and cost, complete control over system design. The size and shape of the fluid channels can be controlled, the wall material can be controlled, the flow rate can be controlled, valves can be added as needed, etc. In short, almost all aspects of the system are amenable to being engineered so that the system meets its functional goals. And, to ensure that this is happening reliably, diagnostic capabilities may be built into, or facilitated, by the system. For example, visual (including microscopic) inspection of microfluidics chambers can be permitted by using a transparent cover material, and such inspection can ensure that the objects within the fluid are being positioned as desired, or that the correct number of objects end up in various bins.

Further, not only are many of the features of an engineered system optimized for a given purpose, but the very fact that they were engineered implies that they are likely to be known. There is generally no need to experimentally determine, for example, the diameter of a microfluidics channel, its shape, or the path that it takes; even if it was arbitrary (which is unlikely), it is still known.

Such an example contrasts with a scenario where there is little or no control over system design, where knowledge of at least some of the system features may range from incomplete to non-existent, and where the system design does not facilitate information gathering (e.g., a transparent cover over the system allowing visual inspection).

As an industrial example, assume fluids (which could be anything from gasses, to water, to highly-viscous fluids such as oil, or foodstuffs such as peanut butter, honey, or sour cream) are pumped through pipes in a processing plant. It may be desirable to put one or more sensor-containing objects into the fluids for quality assurance or other data collection, either of the fluid, of the system itself (e.g., to find leaks, cracks, temperature variations, contaminant buildup, map the system if it has not been completely documented, etc.), or both. The parameters of such a system, such as the layout and construction of the pipes, the fluid in the pipes, and the flow velocities may not be amenable to being changed. And, it is likely that these parameters have not been engineered to be able to easily determine an object's location at a given point in time (for example, the pipes may not be transparent, not just to light, but to radiofrequency, ultrasound, or other sensing modalities, and they may not be easily accessible). Despite this, the sensor-laden objects (aka, devices, which may also be robots) must be able to identify system features, including their own location at a given time if mapping of system features is desired.

Similar problems occur in very different contexts and at very different scales. For example, consider the use of a medical micro-camera or other diagnostic object that could be injected into the blood stream. Some diagnostic data may be useful regardless of knowing the object's position (e.g., blood glucose level), but for other data (e.g., the existence of plaques on the vasculature walls, mapping the vasculature itself, or determining blood oxygen levels, which vary from the arterial to venous side of the circulatory system), it would be useful to be able to determine the position of the object as it moves through the system and correlate that position with the data being collected.

There are many ways to address the issue of position tracking of objects. At some scales, GPS, Wi-Fi, BlueTooth or RFID can be used for position tracking. In other scenarios, such as with medical applications, ultrasound, electromagnetic, or optical methods can be used for imaging and/or position tracking.

Despite the existence of several solutions to the problem of position and feature determination in a fluid system, not all solutions work well at all scales or Reynolds numbers. And regardless, alternative solutions can still be useful, particularly if they offer greater accuracy, a reduction in data processing to reduce computational capacity required, or allow faster processing and analysis of data with the same capacity. Also, alternative solutions need not stand alone, but rather data could be incorporated from multiple methods to refine accuracy and reliability.

Determining Feature Characteristics Using Flow Data

Some embodiments discussed herein include the indirect determination of feature information via the measurement of fluid flow-related data. For example, among the possible feature data of interest, indirect position determination is included in some embodiments of the invention. By "indirect," it is meant that rather than measuring or observing, e.g., position, directly or using well-known means (e.g., using optical or ultrasound inspection), the desired information is inferred by collecting fluid flow data and computing the information of interest.

As an example of the process of indirect position determination, consider a device moving through a fluid system. The device may use various sensors to gather flow data, such as sensors capable of determining the fluid pressure and shear forces at multiple locations across the device's surface. Using these sensors, the device can map, spatially and over time, the patterns of the fluid flow which surround it. However, this information by itself does not provide the device's position. The patterns of fluid flow must be used to deduce information about the local environment. For example, pressure and shear values which differ from one side of the device to the other may indicate the proximity of a wall near one side of the device and give the device information about its velocity relative to the channel. Different values and patterns of the same sensor data may indicate that the device has passed another object in the fluid or could indicate a change in the geometry of the fluid channel (e.g., a curve, branch point, merge, narrowing, widening, or some irregularity such as a plaque or leak). Once such features are determined, the device position can be determined, at least relative to the features (e.g., the position of the device relative to the local channel geometry, or relative to another object in the fluid).

In some cases, device position relative to some feature(s) may be sufficient. However, in other cases it will be useful to determine the device's absolute position within the system. This can be done in a variety of ways, depending on the data available. If a map of the system is available, the position relative to one or more features may be able to be translated into an absolute position. For example, if sensors can gather data, which is then processed using machine learning, allowing the device to determine the geometry of the immediate channel (and perhaps having stored the geometry of other portions of the channel through which the device has already passed), if the geometry is unique and overlaps with data on other regions for which information exists, this may be all that is required to unambiguously identify the position of the device within the overall fluid system (an analogy might be made to the way DNA fragments are assembled into the sequences of complete chromosomes when using shotgun sequencing). If such data are insufficient to unambiguously identify the device's position, it will likely at least narrow down the choices, which may be sufficient for a given situation. If the position of the device needs to be still further refined, additional data can be brought to bear on the problem. For example, if the device has collected additional data over time, the history of where it has been may help to narrow down where it could be now, given known characteristics of the system (e.g., approximate flow rate, or various paths that could have been taken). If such data does not exist or is insufficient, the device may need to make additional passes through the system (and multiple devices could be used to speed up the process), each time gathering data until it is sufficient.

In addition to data directly related to the fluid flow, such as speed and direction, pressure, shear information, and viscosity, other ancillary data may help to infer the desired information. For example, data such as temperature and chemical concentrations can also be collected and can be used to provide information to aid device missions, such as mapping of the fluid system. (Hogg, "Coordinating microscopic robots in viscous fluids," Autonomous Agents and Multi-Agent Systems, 3, Kluwer Academic Publishers-Plenum Publishers, 2007; Turduev, Cabrita et al., "Experimental studies on chemical concentration map building by a multi-robot system using bio-inspired algorithms," Autonomous Agents and Multi-Agent Systems, 1, 2014) If such data varies across the system in known ways (such as temperature decreasing with distance from a heated source), or correlations can be determined, this information may be useful in enhancing the accuracy of inferences made using other data. Various data can not only be combined but can also be measured over time and in multiple locations, allowing spatial and time-based patterns to be analyzed. Note that this still assumes Stokes flow. Time-based patterns are not assumed to exist due to turbulent fluid flow, but rather because something that affects the system is changing over time (e.g., consider variation in diastolic versus systolic blood pressure as the heart beats, or changes in flow rates or temperatures dictated by other equipment in an industrial setting).

Note that all the main sensing modalities described can be passively implemented. They do not require sending electromagnetic waves (e.g., LIDAR, active electrolocation), acoustic waves (e.g., SONAR), or any other type of emission into the environment. Although such techniques could be used for other purposes, such as communication, or could be used in addition to the passive sensing modalities described, they are not needed for, e.g., shear or stress sensing. Additional examples of passive sensing include viscosity sensing, heat or chemical gradient sensing, gravitational direction sensing, gyroscopic or rotation sensing, acceleration sensing, or passive sensing of electromagnetic or acoustic waves (either existent in the system or deliberately induced to facilitate measurements).

It should be noted that passively-sensed characteristics other than shear and stress may be suitable for analysis techniques similar to those described in detail with regard to shear and stress forces. In general, such passive techniques will be more energy-efficient that active techniques. And, as the inventor has discovered, even instantaneous sampling of just a few (in some cases even one, e.g., stress) variables, as long as they are the right variables, and properly analyzed, can be highly accurate and informative, and very tractable to use in real-time or near-real-time.

Inferences made from collected data may be subject to problems like sensor noise or ambiguity in the data. However, it is not always necessary to obtain exact positions, unambiguous feature identity, or complete reliability in any inference for the inference to have value, either by themselves, or in combination with other data or inferences. Any relevant data, even if some uncertainty is present, may, to use Bayesian terminology, help refine the posterior probabilities which can be used to make inferences about the environment.

Computational Modeling

Techniques for modeling fluid flows given the channel geometry and fluid properties are well-known and frequently referred to as "computational fluid dynamics" (CFD). Techniques for inferring channel features and other information of interest given only passive sensor data have not been studied nearly as much. The only work of which the applicant is aware pertains to the lateral lines of fish, and artificial variants thereof, in turbulent environments (Yang, Chen et al., "Distant touch hydrodynamic imaging with an artificial lateral line," Proceedings of the National Academy of Sciences USA, 2006; Pillapakkam, Barbier et al., "Experimental and numerical investigation of a fish artifical lateral line canal," Fifth International Symposium on Turbulence and Shear Flow Phenomena, 2007; Bleckmann and Zelick, "Lateral line system of fish," Integrative Zoology, 2009; Chambers, Akanyeti et al., "A fish perspective: detecting flow features while moving using an artificial lateral line in steady and unsteady flow," J R Soc Interface, 99, 2014; Vollmayr, "Snookie: An autonomous underwater vehicle with artificial lateralline system," Flow Sensing in Air and Water, Springer, 2014; Liu, Wang et al., "A Review of Artificial Lateral Line in Sensor Fabrication and Bionic Applications for Robot Fish," Appl Bionics Biomech, 2016; Tang, Feng et al., "Design and simulation of artificial fish lateral line," International Journal of Advanced Robotic Systems, 1, 2019).

For convenience, fluid flows are often categorized as being viscous (also called Stoke's flow or creeping flow), laminar, or turbulent, depending on Reynolds number. However, the cutoffs between these various regimes are not exact. Mathematically, viscous flow is characterized by a low Reynolds number. The Reynolds number is a dimensionless number defined as: (size*speed*density)/viscosity. A "low" Reynolds number is frequently taken to be less than 1, but there is no sharp cutoff to differentiate viscous flow from laminar flow (or laminar flow from turbulent flow). Rather, as the Reynolds number gets higher, the behavior of the fluid gradually becomes less viscous, and therefore analytical techniques which assume viscous flow become gradually less accurate. Given the gradual decrease in accuracy as the Reynolds number increases, if systems are being analyzed under the assumption of Stokes flow, a Reynolds number of <1 is preferred, a Reynolds number of <0.3 more preferred, and a Reynolds number of <0.1 even more preferred; in many cases, the number will be lower still, such as less than 0.03. Fluid flow systems do not necessarily have a single Reynolds number. Rather, depending on factors such as the local channel geometry, speed of fluid flow, and viscosity, different parts of a fluid flow system could have quite different Reynolds numbers, and the same area of a fluid flow system could have different Reynolds numbers at different times. The devices, methods, and techniques described herein are directed to parts of fluid flow systems with appropriate Reynolds numbers.

Advantages of Analyzing Viscous Flow

A substantial amount of the literature on fluid flow concerns turbulent systems, where quasi-static assumptions do not apply, and where an accurate analysis of physical systems requires gathering data over time to sample the system in its various states. This creates a higher computational burden and requires a non-instantaneous data sampling period.

On the other hand, viscous flow can be treated as being quasi-static at low Reynolds numbers and low Womersley numbers (which generally occur together, unless the system has some force which is causing it to change rapidly, such as high-frequency vibrations, e.g., ultrasound) because viscous forces are much more significant than inertial forces. In terms of data gathering from an actual system, this means that a snapshot in time of the fluid flow parameters suffices. And when modeling a system, a viscous flow system can be treated as static rather than time-dependent. Static models frequently solve much faster than time-dependent models. For example, using the commercial software COMSOL and its CFD module, static models often solve at least 10 times faster than models solved in a time-dependent manner. The difference can be even more extreme depending on the time period analyzed for time-dependent models.

For a device that is often limited in its capabilities (e.g., power storage, computational speed, memory, communication bandwidth) due to its size, and functioning within what may be a relatively small, closed system, a reduction in computational requirements has important physical repercussions. For example, slower computational hardware may be used, which is often smaller and/or more power efficient than faster computational means. Less energy devoted to computations means, e.g., more power is available for other systems, or the device's power production/storage system can be smaller, or the device can run for a longer period without recharging/refueling, or the device can have less impact on its environment when its power requirements affects that environment (e.g., using oxygen and/or giving off carbon dioxide, or generating heat or electromagnetic interference).

Similarly, sensors need only gather data that represents a snapshot in time, rather than gathering a time course of data as would be required to analyze a turbulent (aka, unsteady or transient) system. Not only does this reduce the power required to run the sensors, but by reducing the amount of data that must be collected, this affects things such as reducing the memory requirements to store the data, reducing the power to write that data to memory, and reducing the communication power and bandwidth required to communicate the data to another device in the system, or an external computational resource. Also, as described herein, with proper analysis, just one or two measured values can provide a great deal of information about the local system, further cutting down on memory and communication requirements.

Given that sensors (along with other components that may be involved, such as acoustic transducers) may be mechanical in nature, not only is power consumption reduced, but so is wear on the mechanisms of the device. Computational means may also be mechanical. In such systems, memory may be stored by setting different configurations of jointed connections, and logic is computed through the movement of, e.g., a set of links and rotary joints whose positions change as computations take place. The following references describe how such mechanical computational devices can be implemented and are hereby incorporated by reference: (Merkle, Freitas et al., "Mechanical Computing Systems," US Patent Application 20170192748, 2015; Merkle, Freitas et al., "Molecular Mechanical Computing Systems," Institute for Molecular Manufacturing, 2016; "Mechanical computing systems using only links and rotary joints," ASME Journal on Mechanisms and Robotics, 2018)

Even where computational means are of more traditional types (e.g., electronic), physical wear and tear (and of course, power consumption) still must be considered. For example, even electronic memory storage devices eventually break down. In a traditional hard drive, where bits are stored as magnetically-oriented areas on a platter and changing the value of the bit involves magnetizing the area in a different direction, the platter can be damaged, or the read/write arm can be damaged. For example, when a shock or vibration causes the read/write arm to hit the platter, the magnetic media may be damaged, as may be the read/write arm.

In solid state memory (e.g., NAND- or NOR-based flash memory, where individual memory cells contain NAND or NOR logic gates), the gates eventually wear out because, for example, the voltage pulses uses to change the values stored in the logic gates eventually degrade the semiconductor material to the point where some gates no longer function correctly. Because of this apparently unavoidable problem, some memory devices devote extra space to spare memory cells that can be used when others break down. Of course, this requires extra hardware and software to detect and account for failed memory cells. For example, wear-leveling algorithms (or other techniques, such as BBM, or "Bad Block Management") can be used to try and ensure that, on average, each cell is used the same number of times so that none wear out prematurely. But that only improves the average lifetime of the device, it does not eliminate the damage. So, not only do such devices still fail, but in small devices there may not be space for optional features such as spare memory cells, or space, time or extra power for running wear-leveling algorithms.

Data Inferences

There are various ways in which inferences or determinations can be made using acquired fluid flow data (and other data as desired). For example, one way to interpret such data would be to develop a database of fluid data "fingerprints" or patterns (which could be based on raw sensor data, but more often would be based on select data features). This could be done, e.g., by placing sensors in known positions in an actual system of interest, collecting and analyzing the data, and converting the results to different features of the system (e.g., via machine learning). Subsequently, new data can be compared to the initial database to determine which pre-existing patterns are the closest match. This is referred to in the field of machine learning as classification. To avoid confusion and ambiguity, it is worth repeating that system features are parameters of the fluid system, such as channel geometry, and characteristics of the fluid flow. Data features are not the same as system features. Data features are select data, often transformed in some manner from the raw sensor data, which are used to train machine learning routines. One way to think about this is that machine learning allows data features to be converted to system features, so that when a device collects data, an interpretation of the data can be provided that is easily interpreted by a human. For example, rather than a string of numbers, which may not be very useful to a human, machine learning allows the data features to be turned into inferences such as "the device is in a channel with a diameter of X which branches up ahead."

Another way in which inferences can be made using fluid flow data is to collect the necessary data using system mock-ups. For example, if one is interested in being able to identify features in a vascular system, a microfluidics device could be created that mimics various features of the vasculature but has the advantage that the sensing device can be placed and/or located to allow aliasing the collected data to the position of the device.

Simulations can also be used to create virtual environments which can provide data that is used to train machine learning algorithms which allow inferences to be made from the data. Such simulations offer the advantages of fast iteration time and can provide a large amount of data on many different scenarios without having to build physical mock-ups. For example, by setting up appropriate virtual systems which contain straight segments, curved segments, branching segments, merging segments, other objects in the fluid, or other scenarios, it is possible to run, e.g., Monte Carlo simulations as many times as needed to generate a data set that is used to provide input to a machine learning system and allows robust system feature determination.

If a device were to run into a scenario (e.g., a new geometry) that was not classifiable per the existing data, the scenario could be added to mock systems or simulations, and the system retrained until it could accurately distinguish the new scenario.

The data may be analyzed in its raw form or may be preprocessed. Techniques for preprocessing data for subsequent machine learning are well known. For example, noise can be removed, data averaged, and Fourier and other transforms (optionally including dimension reduction and/or feature selection techniques) can be done on the data.

As an example of the practical application of these techniques, using data obtained from simulations, the present Applicant has been able to achieve very accurate feature discrimination via the collection of surprisingly small amounts of data. For example, using computational model in two dimensions and three dimensions, stress and shear were measured on the surface of an object in a low Reynolds number fluid flow. The virtual channels used included many different geometries, and within these geometries, the device was placed in many different locations. The data were subsequently subjected to a Fourier transform. Then the first few modes of the transformed data were used for regression analysis. The regression analysis showed that devices in viscous flow, by collecting just these pieces of data, can make multiple important quantitative (e.g., velocity) and qualitative (e.g., classification of vessel geometry) determinations. Additionally, it has been shown that this can be done in a manner which is very computationally efficient where it is most important: in a power- and/or space-limited device. The reason for this is that most of the processing is in the generation of the virtual data and the training of the system (e.g., for classification), which can be performed by a remote device (e.g., a typical desktop computer, workstation, or cluster of computers). Once the machine learning training is complete, classifying new data based on the training results is not nearly as computationally demanding as creating and analyzing the data initially.

Of course, the devices and methods described are only exemplary. It will be obvious to those skilled in the relevant arts that, given the teachings herein, many other combinations of devices (along with sensors), data, data processing or preprocessing (including none), and machine learning techniques could also be used.

Device Requirements

In one of the simplest implementations, a device for fluid flow analysis could be comprised of a single type of sensor, and preferably (although optional) some way of communicating the data gathered by the sensor to an external computer (e.g., RF, acoustic, or optical communications, or some direct data transfer after the device has exited the fluid system) for analysis.

While some method of communication, and therefore a power source, is preferable, it is not required in all instances. For example, molecules which have different fluorescent or other properties depending on shear could rely upon external activation or assays. For example: (Haidekker, Grant et al., "Supported molecular biolfluid viscosity sensors for invitro and in vivo use," U.S. Pat. No. 7,670,844, 2010; Mustafic, Huang et al., "Imaging of flow patterns with fluorescent molecular rotors," J Fluoresc, 2010; Zou, Liu et al., "Flow-induced beta-hairpin folding of the glycoprotein Ibalpha beta-switch," Biophys J, 2010; Varma, Hou et al., "A Cell-based Sensor of Fluid Shear Stress for Microfluidics," 17th International Conference on Miniaturized Systems for Chemistry and Life Sciences, Freiburg, Germany, 2013; Zhang, Sun et al., "Red-Emitting Mitochondrial Probe with Ultrahigh Signal-to-Noise Ratio Enables High-Fidelity Fluorescent Images in Two-Photon Microscopy," Anal Chem, 2015).

Assuming communication hardware is built into the device, many means of communication are possible, including wired, wireless (e.g., electromagnetic, such as RF or optical), or acoustic (e.g., generated by piezo-based mechanisms, which could also serve as pressure sensors).

A power source could also take many forms, including a battery, a fuel cell (e.g., a hydrogen fuel cell, or a glucose fuel cell for medical purposes or other environments where a glucose supply, and potentially an oxygen supply, is available, although any necessary fuel could also be carried in onboard storage tanks), induction-based power collection, or a mechanism which uses ambient pressure changes or vibrations to harvest energy from the environment (including pressure changes induced by, e.g., the application of an external ultrasound source).

The ability of a device to actively position itself within a fluid system could be useful, but not required. Data could be gathered as the device passively moves through the system with the fluid flow, or in some cases, device position could be externally manipulated (e.g., magnetically). If onboard locomotion is desired, there are many ways of providing this. For example, traditional propellers, flagella- or cilia-like mechanisms, undulating surfaces, tank tread- or treadmill-like mechanisms (which, while uncommon in everyday experience, can be very efficient at low Reynolds numbers), brachiation with device arms, or mechanisms which allow the device to adhere to the channel wall.

An onboard computer, including memory to store data, could also be convenient, but not necessary. Where onboard computation is used, power and space may be limited, making efficient means of data analysis potentially more important than if sensor data are offloaded to external computing devices.

Note of these choices are mutually exclusive—any combination could be used, of the above examples, or of other methods of addressing such functionality well-known in the arts. The size and shape of a device may be environment- and mission-specific, and could assume any shape, from a sphere, cylinder, or ellipsoid to much more complex shapes (or could change shape as needed), and could be covered with, for example, any number of sensors, propulsion mechanisms, energy harvesting mechanisms, and communication equipment (e.g., antennae).

Exemplary Sensor Positioning or Integration

Sensors can be in many places, and often multiple sensors, potentially of various types, would be placed in one or more locations within a system or on a device within a system. For example, sensors could be external to the fluid system (e.g., the Doppler ultrasound equipment used for medical diagnostics resides outside of the systems it measures). Sensors could be mounted on, or an integral part of, the walls of the fluid system (e.g., wall-mounted or wall-integral sensors can be built into micro-fluidics channels).

Sensors could be mounted on the surface of devices within a system (e.g., pillar-type shear sensors), or within devices (e.g., pressure sensors, such as can be fabricated using piezoelectric sensors). Sensors could also be incorporated directly into the fluid itself when appropriate (e.g., molecular shear sensors).

As an example of device-mounted sensors that could be employed, FIG. 1 depicts a device 50 having shear sensors 52 distributed across part of the surface of a shell 54, and a piezo pressure sensor 56 (which could also serve as an acoustic transducer for both communication and power harvesting) on another part of its surface. The sensors employed could be of various types, such as shear sensors, velocity sensors, direction sensors, pressure sensors, and many other types, including combination sensors that collect more than one type of data. Of course, FIG. 1 is a diagrammatic representation and the shapes, sizes, numbers, placement and types of sensors, propulsion, power storage, communication, and other mechanisms, can vary as desired, and some may not be present at all. The illustrated device 50, by way of example, employs a battery 58 to provide power to the sensors (52, 56) as well as to an on-board computer 60, and a treadmill locomotion unit 62. An antenna 64 allows the computer 60 to receive data from a remote site, and may allow transmission to such site, which could be an operator interface and/or could be other devices.

Exemplary Analysis of Non-Locomoting Device in a Vessel

Figures 5A, 5B:
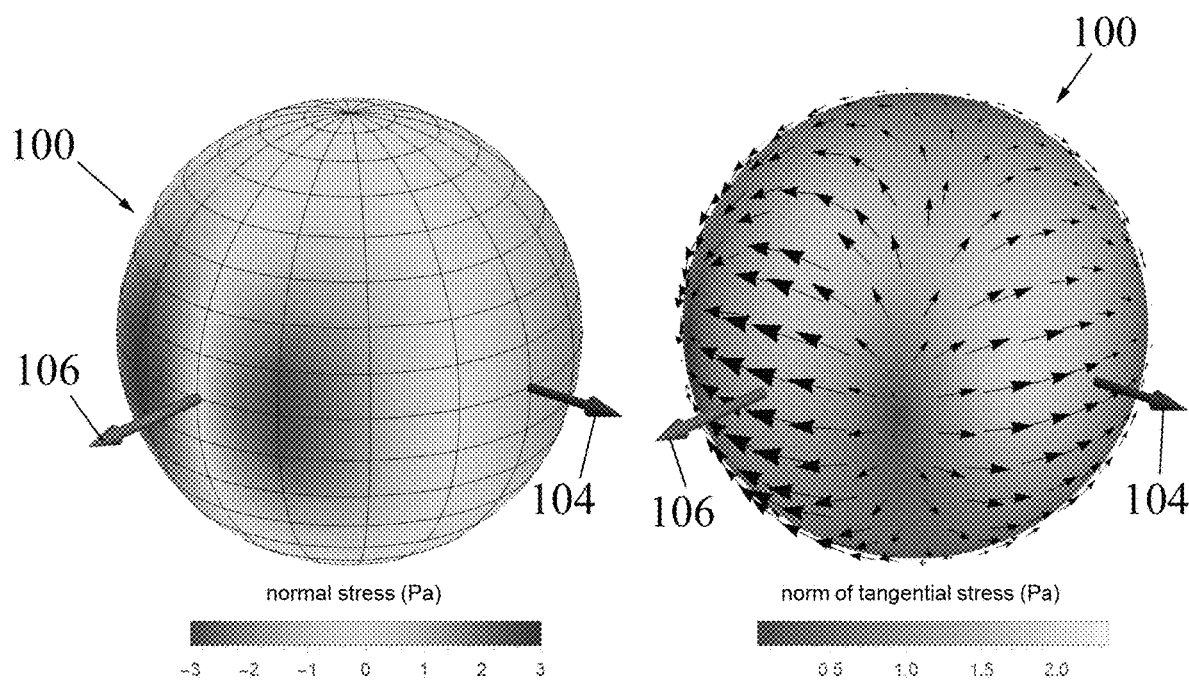
FIGS. 5A and 5B respectively illustrate the normal and tangential (shear) stresses across the surface of the device resulting from the fluid flow and the device movement relative to the fluid and boundaries in the situation shown in FIGS. 2 and 4.

To illustrate the present techniques, FIGS. 2-4 illustrate a relatively simple situation for analysis, where a spherical device 100 moves passively through a straight, cylindrical vessel 102. FIG. 2 shows the device 100 and vessel 102, while FIG. 4 illustrates a cross-section that can be used in a 2D analysis of the device motion. This motion results in stresses on the surface of the device 100, as illustrated in FIGS. 5A and 5B (3-dimensional analysis) and in FIGS. 6A-8B (2-dimensional analysis). In the cases considered herein, the flow speed, vessel size and fluid viscosity result in viscous flow (also known as Stokes flow or creeping flow). (Happel and Brenner, "Low Reynolds Number Hydrodynamics," The Hague, Kluwer, 1983), (Hogg, "Using surface-motions for locomotion of microscopic robots in viscous fluids," J. of Micro-Bio Robotics, 2014). For purposes of the present discussion, Stokes flow can be considered to exist when the Reynolds number:

$$Re = \frac{ud}{v} \quad (1)$$

of the flow is small (i.e., Re<1). In this expression, v is the fluid's kinematic viscosity, d is the vessel diameter and u is the flow speed. For a device moving slowly in such flows, the fluid motion at each time is close to the static flow associated with its instantaneous position, velocity, and orientation. This quasi-static approximation applies for small values of the Womersley number:

$$W_o = \frac{r}{\sqrt{vt}} \quad (2)$$

where r is the radius of the device and t is the time over which the geometry changes. As with the Reynold's number, there is no strict cutoff for values of the Womersley number at which quasi-static analysis is applicable; rather, such analysis becomes less accurate as the number increases. For many purposes, the approximation should be appropriate for a Womersley number of less than 1 (and like the Reynolds number, a Womersley number of <1 is preferred, <0.3 more preferred, <0.1 even more preferred, and some systems will have even far lower Womersley numbers, where the quasi-static approximation then becomes almost exact). Changes in device geometry can arise from and actual change in its shape (e.g., if the device were flexible or had moveable segments), or changes in its position and/or orientation. The time for significant change in the device's position is of order $r/v_{device}$, which is larger than r/u because a device moving passively in the fluid moves more slowly than the fastest fluid speed in the vessel. Similarly, significant changes in orientation take time of order $1/\omega_{device}$, which is also larger than r/u. Thus, a lower bound on the time for significant geometry change, at least from passive changes in position or orientation, is t>r/u.

Evaluating the flow in this example requires specifying boundary conditions at the ends of the vessel segment and on the wall. Specifically, the incoming flow can be taken to be fully-developed Poiseuille flow (Happel and Brenner, "Low Reynolds Number Hydrodynamics," The Hague, Kluwer, 1983). This gives a parabolic velocity profile at the inlet, with maximum speed u at the center of the vessel. A pressure gradient drives the flow, so shifting the pressure by a constant leaves the flow unchanged. For definiteness, the pressure can be set to zero at the outlet. The vessel walls are no-slip boundaries, where the fluid velocity is zero. The flow velocity matches the device's motion at each point on the device's surface, expressed in terms of the device's center-of-mass velocity and angular velocity.

FIGS. 5A and 5B illustrate the resulting pattern of normal stress and tangential stress, respectively, on the surface of the spherical device 100, when moving through the vessel 102 with the geometry and viewpoint of FIG. 2 (the specific parameters used in generating the figures for the present discussion are described in the numerical example discussed herein). The arrow 104, on the right of the spherical device as shown in FIGS. 5A and 5B, indicates the direction of motion of the device 100, as also shown in FIGS. 2 and 4. The arrow 106 indicates the direction to the nearest point on the vessel wall. FIG. 4 shows a section of the vessel 100, with diameter d, and the spherical device 100, with radius r, with its center at position $y_c$ with respect to the cylindrical vessel axis 108, and distance $d/2-|y_c|$ from the vessel wall 110.

Comparing Two- and Three-Dimensional Flow Analysis

FIG. 5A illustrates the normal components of stress on the surface of the device 100, where positive and negative values correspond respectively to tension and compression. FIG. 5B illustrates the tangential components of stress on the surface, with arrows showing the direction and relative size of the tangential stress vectors and the color indicating its norm. The fluid flow is driven by a pressure gradient in the vessel. Adding an arbitrary constant to the pressure does not change the flow but contributes to the normal force on the device surface. To remove this arbitrariness, the present calculations select this constant such that the total measured normal stress on the surface of the device is zero.

The stress is relatively large on the side of sphere facing the nearby vessel wall. In addition, the largest variation of the stress is in the azimuthal direction around the sphere's equator 112. In particular, the largest magnitude of the tangential stress is at the point of the sphere closest to the vessel wall 110. The sphere's direction of motion is nearly 90° around the equator from that closest point.

Figure 7A:
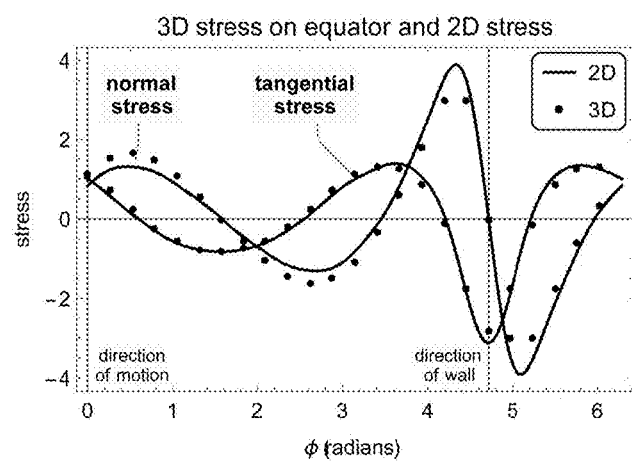
FIGS. 7A and 7B compare results for 2-dimensional and 3-dimensional analyses of the stresses on the device, corresponding to the situation illustrated in FIGS. 2 and 4.

FIG. 7A compares the stress from 2-dimensional analysis of fluid flow (indicated in solid lines) with the stress around the sphere's equator from 3-dimensional flow (indicated with individual points). In the latter case, by symmetry, the tangential stress is directed around the equator, thereby matching the direction of the tangential stress of the 2-dimensional case. The normal and tangential stresses for the scenario illustrated in FIGS. 5A and 5B, as a function of azimuthal angle φ from 0 to 2π, are measured from the direction of a cylinder axis 108 (shown in FIG. 4), which is nearly parallel to the device's direction of velocity. The two vertical lines indicate the direction of motion (indicated by arrow 104 in FIGS. 5A and 5B) and the direction of the nearest point on the vessel wall (indicated by arrow 106). Positive tangential stress is in the direction of increasing φ, i.e., counterclockwise rotation. The stress components correspond to the stress vectors shown in FIG. 8A.

Figure 7B:
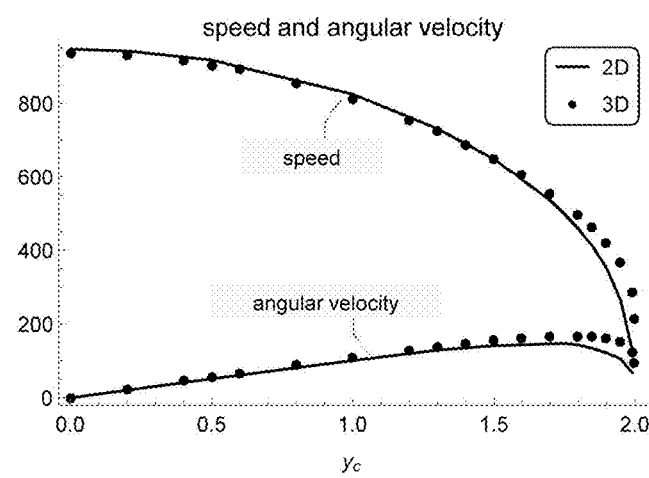

As an additional comparison between the 2-dimensional analysis and the 3-dimensional analysis, FIG. 7B compares the device's speed through the vessel, $v_{device}$, and angular velocity, $\omega_{device}$, as a function of relative position in the vessel, $y_c$, for the geometry of FIGS. 2 & 4, but varying the position of the device in the vessel (as used herein, "relative position" or r.p. is a measure of the center of the device relative to the center of the vessel, accounting for the device and vessel diameter so as to range from 0, where the device is centered in the vessel, to 1, where the device is just touching the vessel wall). The resulting speed and angular velocity are calculated varying the position, $y_c$, of the sphere's center within the vessel, ranging from zero (where the sphere is in the center of the vessel), to slightly less than d/2−r=2 μm (where the sphere is almost touching the vessel wall). In these cases, the device's motion is very nearly parallel to the cylinder's axis because the transverse component of the device's velocity is significantly smaller than its velocity parallel to the vessel. In all comparisons performed, the 2-dimensional and 3-dimensional calculations give very similar results. Thus, in the following discussions, two dimensional examples are generally used for simplicity.

Surface Stresses Resulting from Fluid Flow and Device Movement

In the case discussed above, where a spherical device moves passively in a straight vessel, such as shown in FIGS. 2 and 4, and where the effects of gravity and Brownian motion can be considered negligible, the stresses on the device surface can be determined by numerically evaluating the flow and device motion in the segment of the vessel. Due to symmetry in this basic example, the device's velocity lies in the cross section of the plane shown in FIG. 4, and a simplified numerical evaluation can be made by using two-dimensional quasi-static Stokes flow analysis, as discussed above.

Figure 6A:
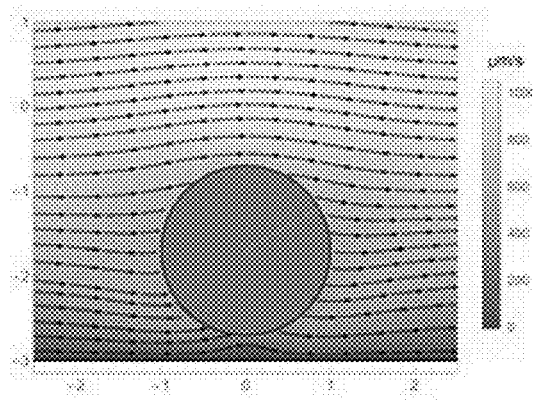
FIGS. 6A and 6B illustrate a 2-dimensional representation of the flow that causes surface stresses on the device, corresponding to the region 6 shown in FIG. 4.
Figure 6B:
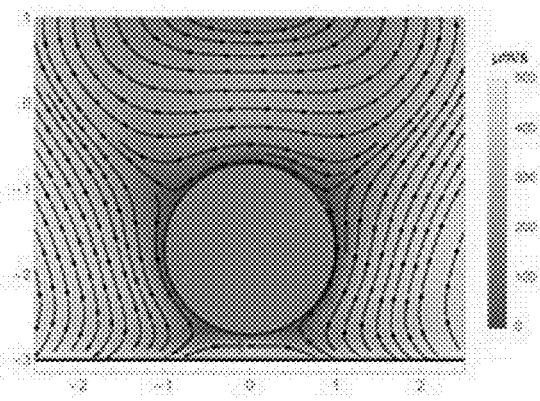
Figure 8A:
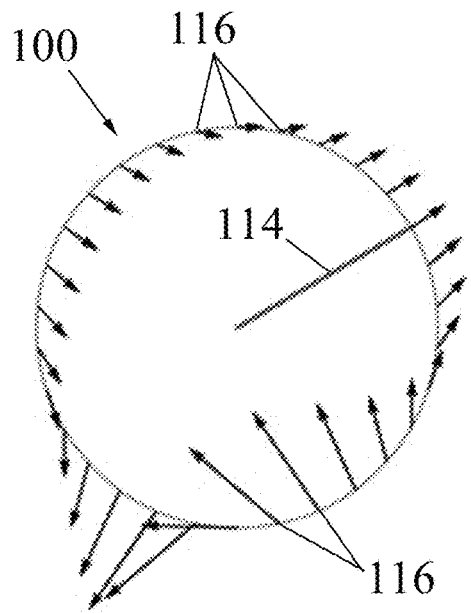
FIG. 8A illustrates a 2-dimensional representation of the resulting stress vectors at the locations of 30 sensors on the device, for the situation shown in FIG. 4.
Figure 8B:
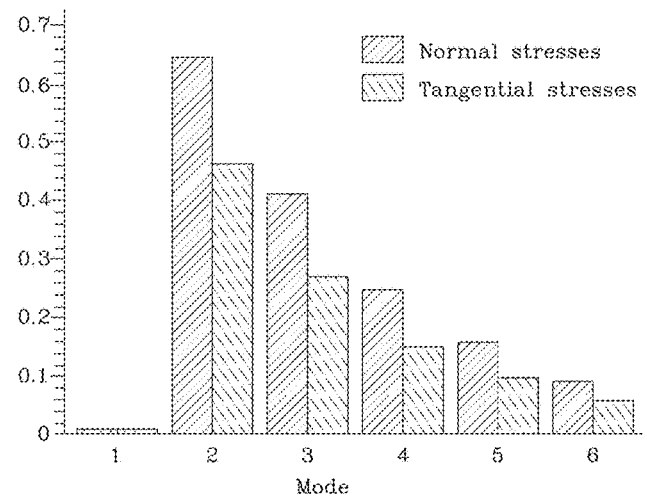
FIG. 8B illustrates the resulting first six Fourier components that result from a Fourier decomposition of stresses as a function of angular position.

FIGS. 6A and 6B illustrate a 2-dimensional representation of the flow and stresses on the device surface, of the region 6 shown in FIG. 4, using an arbitrary choice for the orientation of the device 100, illustrated by orientation line 114 (labeled in FIG. 8A), with respect to the vessel 102. The fluid pushes the device through the vessel with a translational velocity $v_{device}$ (from left to right as viewed in FIG. 6A) and with an angular velocity $\omega_{device}$ which is negative (i.e., clockwise rotation as viewed in FIG. 6A). FIG. 8A shows how resulting stresses vary over the device surface. A useful representation of the stress pattern is its Fourier decomposition (discussed in greater detail herein, with regard to determining device orientation). In this example, the largest contribution is from the second mode, for both normal (pressure) and tangential (shear) components of the stress, as shown in FIG. 8B.

Evaluating Device Orientation, Location, and Vessel Geometry

FIGS. 6A, 6B, 8A, and 8B illustrate one example of instantaneous stress measurements that can be used to calculate values of device orientation and position in a vessel, and the vessel's diameter; in this case, a 2-dimensional analysis is performed. Together, these calculated values give the device's relation to the vessel through which it moves. The following discussion again refers to the spherical device 100 and cylindrical vessel 102 shown in FIGS. 2 and 4 (using data generated from the specific numerical example discussed herein).

FIGS. 6A and 6B indicate the fluid flow near the device 100, in the section of the vessel 102 shown in FIG. 4. The orientation of the device 100 is indicated by the orientation line 114 (shown in FIGS. 8A & 9). Arrows show streamlines of the flow and colors show the flow speed. FIG. 6A illustrates the fluid velocity with respect to the vessel. Velocity is zero at the vessel wall 110, and matches the motion of the device 100 at its surface. FIG. 6B shows the fluid velocity with respect to the device 100. Velocity is zero at the device surface. FIG. 8A illustrates the stress vectors on the device surface. The arrow lengths show the magnitude of the stresses at the locations of sensors 116 distributed on the device surface at different angles ϕ with respect to the orientation line 114; in this example, 30 sensors 116 are employed. FIG. 8B shows the relative magnitudes of Fourier coefficients of the first six modes of normal and tangential components of stress on the device's surface.

Device Orientation

Objects may rotate as fluid pushes them through a vessel. As seen in FIG. 8A, the device 100 has large tangential stress on its side closest to the vessel wall 110. This stress arises from the large velocity gradient between the device's moving surface and the stationary fluid at the wall, as illustrated in FIG. 6A. Thus the location on the device's surface with largest tangential stress magnitude identifies the direction to the nearest vessel wall 110.

The simplest orientation value based on this observation would be to use the location of the device's stress sensor 116 with largest tangential stress magnitude. However, this approach is limited in resolution to the spacing between sensors (as well as positioning of sensors on a 3-dimensional spherical surface not aligning with a plane most suitable for a related 2-dimensional analysis) and is sensitive to noise that might be present in a single sensor 116. A more robust implementation uses the angle $\vartheta_{extreme}$ with respect to the front of the device (as indicated by the orientation line 114), that maximizes the magnitude of an interpolation of tangential stress measurements around the surface. In one example of such analysis, the interpolation is based on low-frequency Fourier modes. This interpolation combines information from multiple sensors to reduce noise and can identify locations that lie between sensor positions for improved resolution. The calculated direction to the wall, $\vartheta_{wall}$, is taken to be the direction of the normal vector at the location $\vartheta_{extreme}$ on the surface. For circular devices, the surface normal vector aligns with the center of the device such that $\vartheta_{extreme}=\vartheta_{wall}$. However, these angles can differ for other shapes, as discussed herein regarding elongated devices.

As shown in FIGS. 2 and 4, the device's motion is nearly parallel to the vessel wall 110. Thus, the device 100 can evaluate its direction of motion as being roughly perpendicular to its calculated direction to the closest wall 110

(indicated in FIGS. 2 and 4 by the arrow 106). More specifically, FIG. 8A shows that, near the direction to the wall 110, the normal stress is negative in the direction of motion. This observation allows the device 100 to determine whether the direction of motion is +90. or −90. from the direction to the wall 110, as discussed regarding determining device motion.

Calculated Values from Stress Measurements

Fourier Coefficients

Stresses vary fairly smoothly over the device surface, as illustrated in FIG. 7A. This observation motivates representing the stresses by a Fourier expansion in modes with low spatial frequencies. Limiting consideration to these modes reduces the effect of noise and is computationally efficient.

The Fourier coefficient for mode k is $$c_k = \frac{1}{n}\sum_{j=0}^{n-1} f_j \exp\left(2\pi i \frac{jk}{n}\right) \quad (3)$$

where n is the number of sensors and k ranges from 0 to n−1. To focus on low-frequency modes, the present analysis considers only modes up to k=M, with M<n/2.

Figure 9:
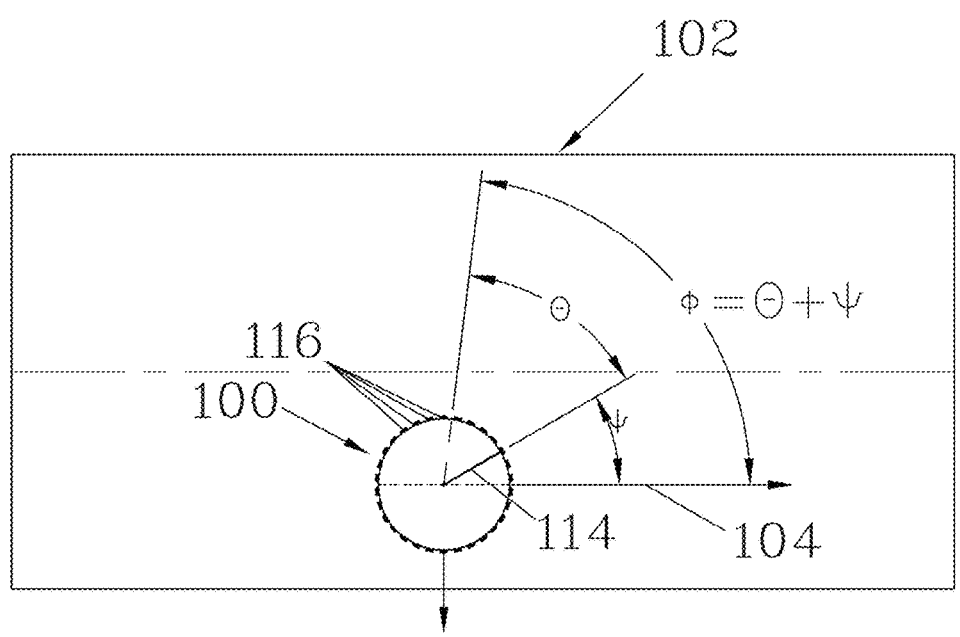
FIG. 9 illustrates the positions of a 2D array of sensors on the device shown in FIGS. 2-4 and an orientation line used to define a front of the device for reference when analyzing the stress pattern across the device surface.

The examples discussed herein use M=6 and n=30 (six modes, thirty sensors 116), as shown in FIGS. 8A and 9. In the following discussion, these coefficients are used in two ways.

First, the stress measurements are extended from the locations of the device's sensors to the full surface by interpolating the Fourier modes. Mode k is the real part of $c_k e^{-i\theta k}$, where θ is the angle around the device's surface measured counterclockwise from the front of the device (see FIG. 9). The interpolated stress values are $$f(\theta) = \Re\,(c_0 + 2\Sigma_{k=1}^M c_k e^{-\theta k}) \quad (4)$$

where $\Re$ denotes the real part and the factor of 2 accounts for the symmetry between modes k and n−k.

Second, machine learning is applied to determine relations between these Fourier coefficients and properties of the vessel near the device. To simplify this procedure, the relative magnitudes of the Fourier coefficients $m_k$, are used, with components $$m_{k,s} = \frac{1}{C}|C_{k,s}| \quad (5)$$

where s denotes either the normal or tangential component of the stress, and C is the root-mean-square magnitude of the coefficients, i.e., $C=\sqrt{E_k|c_k|^2}$ with $|c_k|^2=\Sigma_s|c_{k,s}|^2$. The constant mode, $c_0$, does not contribute to the variation in stresses around the device, so is not included in this normalization. The relative magnitudes simplify the evaluation because they are independent of the device's orientation, the overall fluid flow speed, and the fluid's viscosity. This is because 1) the device's orientation affects the phase of the Fourier coefficients, but not their magnitudes, and 2) the stresses for Stokes flow are proportional to the flow speed and fluid viscosity (Kim and Karrila, "Microhydrodynamics," Dover Publications, 2005), so the normalization removes this dependence. This allows for a very efficient process from a computational standpoint: All that ends up being needed to accurately determine several important system features are the relative magnitudes of the first few Fourier modes of the normal and tangential components of stress.

Evaluating the Direction of Motion

As pointed out when discussing FIG. 8A, a device can evaluate its direction of motion through the vessel from the observation that the direction of motion is nearly perpendicular to the direction to the wall. Specifically, FIG. 8A shows the derivative, $df_{normal}/d\theta$, of the normal stress at $\theta_{extreme}$ is negative. If the direction of flow, and hence motion, were reversed, this derivative would be positive. Thus, the sign of this derivative, s, identifies whether the motion is +90° or −90° from the direction to the wall, i.e., the direction of motion is $\theta_{wall}-90°$ or $\theta_{wall+s}90°$, respectively.

This evaluation technique was modeled for a sample of devices at various positions and orientations in vessels, using variations of the situation show in FIGS. 2 & 4 for a range of vessel diameters and flow speeds, and the mean magnitude of the errors for both the indicated direction to the wall and the indicated direction of motion were found to be less than 1 degree (surprisingly accurate due not only to the small number of data features being used, but also because this resolution is far smaller than the spacing of the sensors, which in this example is one every 12 degrees). The largest errors occurred for devices near the center of the vessel, where the tangential stresses on the sides facing the opposite walls are nearly the same. However, for devices near the center, the wall in either direction is at about the same distance from the device, so such errors have little significance at such central location. Devices in such locations could adopt various strategies to address the possible inaccuracy in such circumstances; examples include ignoring or de-weighting current readings and relying on previous values, or, if present, communicating with other nearby devices (particularly those located near the vessel wall, having a large value for relative position) to obtain more accurate values.

Relating Stresses to Device and Vessel Properties

The pattern of stresses across the device surface are affected by the relative position of the device in the vessel and the geometry of the vessel. These differences can allow evaluating, based on stress measurements across the device surface, information on the position of the device in the vessel and the geometry of the vessel. Some of this information is available based on instantaneous measurements, while additional information can be obtained by monitoring how such instantaneous measurements change over time. The discussion below describes examples of the use of particular machine learning techniques to obtain evaluations for parameters of the device position in the vessel and geometric properties of the vessel.

Relative Position in the Vessel

The patterns of surface stresses are significantly different for devices near the center of the vessel and those near its wall. A useful way to express this variation independently of vessel diameter is through the device's relative position in the vessel, defined as $$rp = \frac{|y_c|}{d/2 - r} \quad (6)$$

where $y_c$ is the position of the device's center relative to the central axis of the vessel, as shown in FIG. 4. Relative position ranges from 0, for a device at the center of the vessel, to 1, for a device just touching the vessel wall. The relative position can be calculated from stress measurements with a regression model, as discussed below.

Different machine learning methods have a variety of trade-offs among expressiveness, accuracy, computational cost for training and use, and availability of training data (Hastie, Tibshirani et al., "The Elements of Statistical Learning: Data Mining, Inference, and Prediction," Springer, 2009; Mostafa, Ismail et al., "Learning From Data," AML-Book, 2012; Jordan and Mitchell, "Machine learning: Trends, perspectives, and prospects," Science, 2015). The following discussion describes regression methods, which perform well with only a modest number of training instances, and whose trained models require only a relatively small number of computations to evaluate. It will be obvious to those skilled in the art given the teachings herein, including the data gathered, features selected, and inference models used, that many alternative techniques could be employed.

Principal Components of Fourier Coefficients

To evaluate the device's position in the vessel and the vessel diameter, training samples were used to fit regressions between these properties and the Fourier coefficients of the stresses. However, these Fourier coefficients are highly correlated in these samples, which make regressions numerically unstable. To avoid this problem, these correlations were removed by using the main principal components of the Fourier coefficients. That is, the regressions were trained using just the principal components accounting for most of the variation among the modes (Golub and Loan, "Matrix Computations," Baltimore, Md., John Hopkins University Press, 1983). With M=6 Fourier coefficients for each of normal and tangential stresses, the first two principal components account for 98% of the variance among the training samples. Thus, just the first two principal components were used for evaluation in this example.

Figure 10:
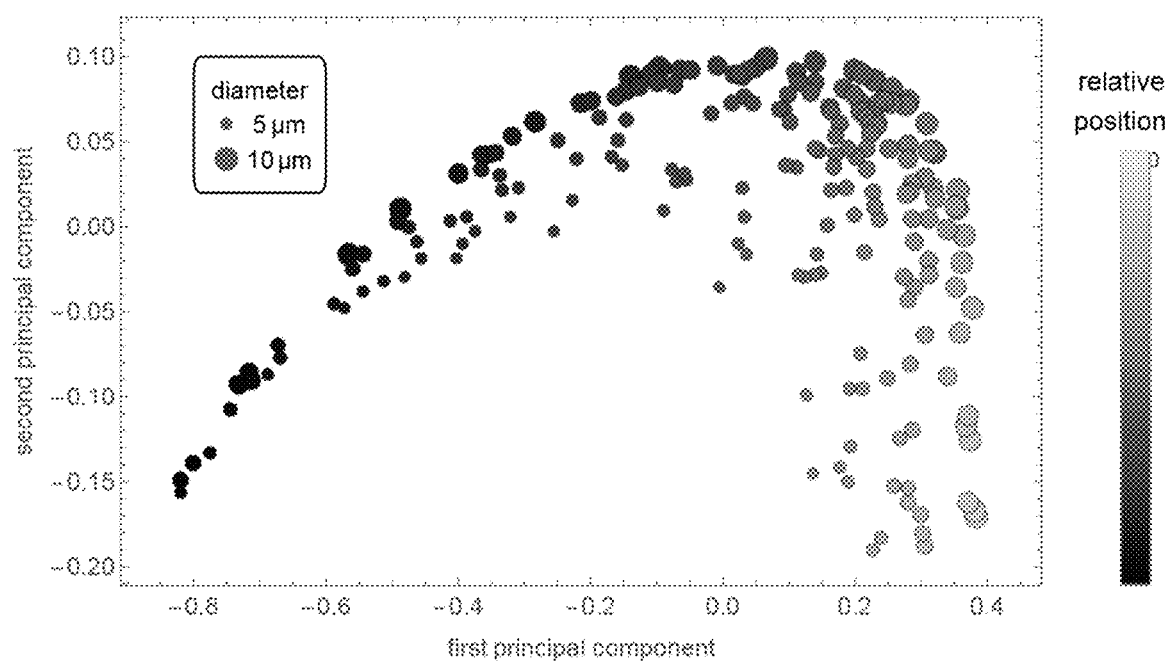
FIG. 10 is a plot showing how both vessel diameter and relative position of the device relate to the first two principal Fourier components of the stresses. For both parameters, values fall within distinct regions, allowing machine learning techniques to accurately evaluate each of these parameters based on just the first two components.

FIG. 10 is a graph that indicates the range of the first two principal components for 200 test samples evaluated in the numerical example discussed herein. In FIG. 10, the disk sizes indicate vessel diameter and colors show the device's relative position, given by Equation (6). The lower left portion of the graph of FIG. 10 shows cases with the device near the center of the vessel. The lower right shows devices near the vessel wall. Thus, the first component mainly varies with the device's position in the vessel and the second with the vessel's diameter. The small spread in points for devices near the center of the vessel indicates relatively little information on vessel geometry from pattern of stress in that case. This leads to worse evaluation performance when devices are near the center of the vessel.

Figure 11:
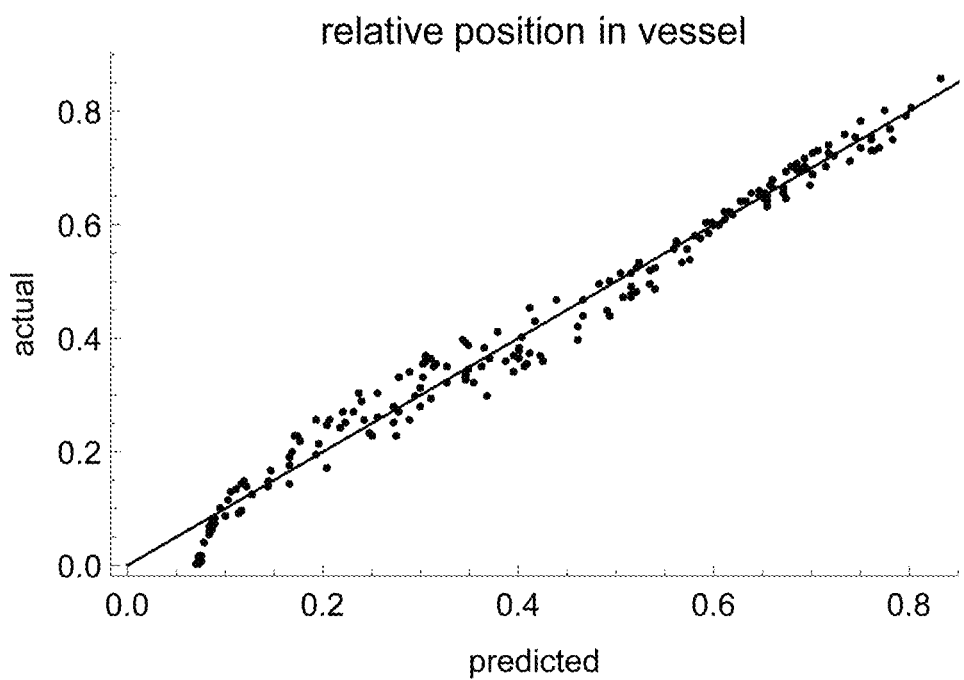
FIG. 11 is a plot comparing actual values for the relative position of the device to calculated values based on machine learning samples.

FIG. 11 is a graph that compares predicted and actual values of relative position for the set of test samples discussed herein. The root mean square (RMS) error is 0.032. Thus, by measuring surface stress, a device can fairly accurately determine its relative position in the vessel. The regression is least accurate for devices close to the center of the vessel, i.e., with relative position less than about 0.1.

Vessel Diameter

For flow at a given speed, wider vessels have smaller fluid velocity gradients than narrower ones. These leads to different stress patterns for devices at given relative positions in those vessels, especially for devices close to the wall, where gradients are largest. A device can exploit these differences with a regression relating vessel diameter to Fourier coefficients of the stress.

Since diameter is a positive value, an evaluator can be constrained to give positive values. Specifically, a generalized linear model (Dobson and Barnett, "An Introduction to Generalized Linear Models," CRC Press, 2008) with logarithm link function and gamma distribution for the residual was studied. Vessel diameter has a strong nonlinear relation with the first two principal components of the Fourier coefficients, as seen in FIG. 10. A regression using only linear variation of the principal components gives less accurate values; depending on the accuracy requirements of the intended application, greater accuracy may be desirable. Including quadratic terms accounts for much of the nonlinear relationship, giving a value for the diameter d, in microns, as:

$$d = \exp(\beta_0 + \Sigma_{i=1}^{2} \beta_i p_i + \Sigma_{1 \leq i \leq j \leq 3} \beta_{i,j} p_i p_j) \qquad (7)$$

(using the parameters provided in Table 4 herein).

Figure 12:
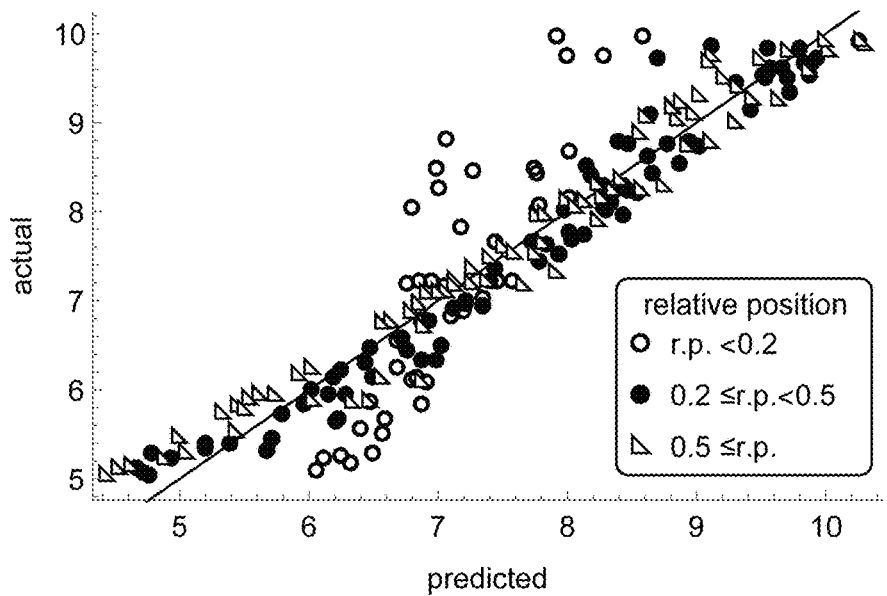
FIG. 12 is a plot comparing actual values for vessel diameter to calculated values based on machine learning samples, indicating that the accuracy is to some degree dependent on the relative position of the device in the vessel, with devices near the center of the vessel providing less accurate values.

To evaluate the accuracy of this regression, predicted and actual values for vessel diameter for the test samples are compared in the graph of FIG. 12. The straight line in FIG. 12 indicates perfect prediction (i.e., where predicted and actual values are the same). The point markers group the instances by their relative positions, as described in the legend. The root mean square (RMS) error was found to be within about 10% of the actual diameters, with the largest errors being for devices near the center of the vessel (e.g., relative positions smaller than 0.2).

Distance to Vessel Wall

Eq. (6) defining the relative position of the device relates the relative position of the device, the vessel diameter, and the distance of the device's center to the vessel wall, such that the distance to the wall can be expressed in terms of the calculated relative position and vessel diameter.

$$d_{wall} = \frac{d}{2} - \frac{rp*d}{2-r} - r \qquad (8)$$

Figure 13:
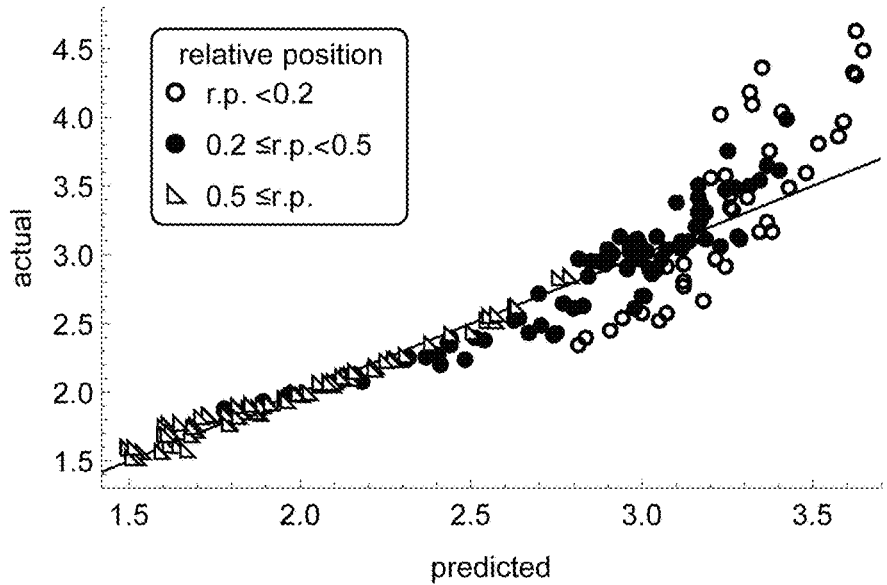
FIG. 13 is a plot comparing actual and calculated values for distance from the device to the nearest wall, derived from the values for relative position and vessel diameter. Again, the accuracy is dependent on relative position.

Thus, combining the calculated values of relative position and vessel diameter as discussed above provides a value for the device's distance to the wall. An evaluation of this procedure for the test samples is shown in FIG. 13. Calculated values for distance to the wall are accurate for devices near the wall, allowing the device to identify when it is close to the wall. On the other hand, prediction error is particularly large for devices near the center of the vessel (r.p.<0.2, where "r.p." stands for "relative position," and is measured as distance from the center of the vessel).

Evaluating Device Motion

The above examples describe evaluation of instantaneous parameters based on measurements of the stresses on the surface of the device. Further analysis can evaluate the motion of the device in the vessel. For Stokes flow, the stresses, and hence the Fourier coefficients, are linear functions of the device's speed and angular velocity. The stresses have a more complex dependence on the geometry (i.e., vessel diameter and the relative position of the device within the vessel). One approach to evaluating motion is to train regression models of these relationships, like the procedure discussed for evaluating position.

An alternative approach derives a value for angular velocity from how stresses change with time and combines that value with a regression model to evaluate the device's speed through the vessel. The capability of monitoring changes in the stresses over time could be accomplished using an onboard timer or by receiving a time signal communicated from an external source.

Angular Velocity

For straight vessels, the rate of change in the direction to the vessel wall relative to a defined "front" of the device equals the device's angular velocity. Because a device's motion in the vessel is mainly directed downstream (assuming the case of a passively-moving device), the distance to the wall changes relatively slowly, and thus the pattern of stress on the device surface, measured from the front of the device, maintains roughly the same shape but shifts around the device due to its rotation. Thus, the device can evaluate its angular velocity from the angle $\Delta\theta$ that the stress pattern moves around its surface in a short time interval $\Delta t$: $\omega_{device} \approx -\Delta\theta/\Delta t$. A device can determine $\Delta\theta$ from the correlation between the surface stresses at these two times. A device can use the shift in its surface stress pattern over a short time Otto evaluate its angular velocity, if the device has access to a clock with sufficient precision (as noted, this could be either an onboard clock or an externally-provided time signal).

The analysis supposes that $f(\theta,t)$ is the stress at angle $\theta$ and time t. If the stress maintains its shape as the device rotates, then $\Delta\theta$ would be the value such that $f(\theta+\Delta\theta,t+\Delta t)=f(\theta,t)$ for all $\theta$. However, any change in the shape of the stress pattern will mean there is no such constant value. A more robust approach to determine $\Delta\theta$ is the value maximizing the correlation between the stresses at the two times. A check on the assumptions underlying this method is that the maximum correlation is close to one, indicating that the main change in stresses is rotation around the device, rather than, say, significant change in vessel geometry or the device's distance to the vessel wall during time interval $\Delta t$.

This procedure must compare stresses close enough in time to avoid the device completing a full turn, i.e., avoiding aliasing. For instance, the device could measure the shift at a sequence of increasing intervals of time until there is a sufficient change in the angle of maximum correlation to reliably identify the change, but not so much that the shift exceeds a full turn. A simpler approach is to use a fixed time interval, selected based on the expected angular velocities such that the change in orientation within a measurement interval is a fraction of a full rotation (e.g., less than one radian), thereby avoiding aliasing.

One way to apply this method is to evaluate the correlation at shifts of an integer number of sensors. This is a simple computation, but limits $\Delta\theta$ to be an integer multiple of spacings between sensors. A more precise method, discussed herein, has the device interpolate its stress measurements (Eq. (4)), and determine $\Delta\theta$ as the value maximizing correlation between interpolated stress values at the two times. Calculated values based on normal and tangential stresses are similar. In the current example, the average from these two stress components was employed.

Figure 14:
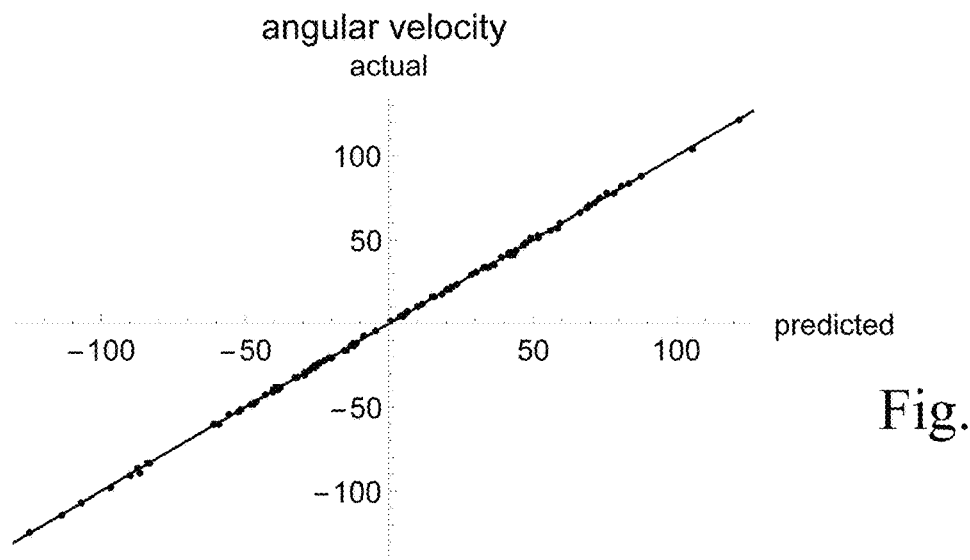
FIG. 14 is a plot comparing actual to calculated values for angular velocity of the device, with the calculated value being obtained by monitoring the change in the pattern of instantaneous stresses after a short time interval.

This method was evaluated with 100 of the test samples, where the motion of each sample was evaluated for small time intervals and the angle $\Delta\theta$ maximizing the correlation between the stresses before and after the motion was determined. The maximal correlations were above 99.9% for all the samples, indicating negligible change in the shape of the stress pattern during this time interval. FIG. 14 shows a comparison of predicted and actual values of the angular velocity (in arbitrary units since the relationship holds for wide-ranging size and time scales as long as the flow is viscous; the same concept applies to FIGS. 12 and 13, and other plots where specific units are not provided) for these samples, with the reference straight line indicating perfect prediction (i.e., where predicted and actual values are the same).

Relating Stresses to Device and Vessel Properties

The flow in a vessel has a parabolic speed profile (Happel and Brenner, "Low Reynolds Number Hydrodynamics," The Hague, Kluwer, 1983). Thus, near the center the flow is relatively fast and the gradient of speed with distance from the vessel wall is relatively small. Conversely, near the vessel wall the speed is low and gradient large. These variations mean that a device near the center moves relatively quickly along the vessel, but rotates slowly, since the flow on either side is fairly similar (or identical, for a device exactly in the center). On the other hand, a device near the wall moves slowly along the vessel, but the large velocity gradient makes the device rotate rapidly. Thus, the ratio of speed through the fluid to rotational velocity at the device's surface:

$$S_{ratio} = \left|\frac{\vartheta_{device}}{\omega_{device} r}\right| \qquad (9)$$

is large for a device near the center of the vessel and small for a device near the wall. Since both device speed and angular velocity are proportional to overall fluid sped and viscosity, their ratio is independent of these factors. The speed ratio is close to a linear function of the odds ratio, $(1-\text{r.p.})/\text{r.p.}$, of the relative position defined by Eq. (6). Thus, a useful model for evaluation of the speed is a least-squares fit to the training samples, which gives $$S_{ratio} = a + b\left(\frac{1-rp}{rp}\right) \qquad (10)$$

with $a=3.1\pm0.2$ and $b=5.41\pm0.03$, where the ranges indicate the standard errors of the values. For the test samples of this example, this fit was found to give a median relative error of 8% for the speed ratio. The largest errors arise when the device is very close to the center of the vessel (i.e., cases with r.p.<0.01).

Speed

Figure 15:
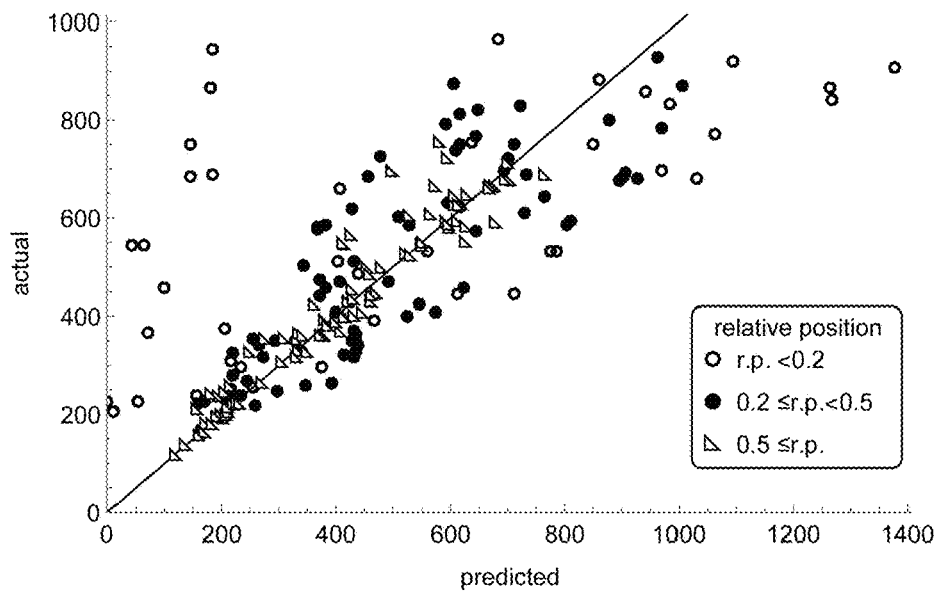
FIG. 15 is a plot comparing actual and calculated values for speed of the device along the vessel.

Combining calculated values of angular velocity and speed ratio gives a value for the device's speed through the vessel via Eq. (9). FIG. 15 illustrates a comparison of evaluated and actual speeds (in arbitrary units, for reasons described herein) for the test samples, with the straight line indicating perfect evaluation (i.e., where calculated and actual values are the same), and with the point markers grouping the instances by their relative positions, as described in the legend. The mean relative error is 20%. The prediction error varies significantly with device position; specifically, mean relative errors are respectively 43%, 21%, and 7% for relative positions less than 0.2, between 0.2 and 0.5, and at least 0.5. The large error for small relative positions (i.e., when the device is close to the center of the vessel) is due to unreliable calculated values of the speed ratio in such cases.

To illustrate specific calculations to evaluate the effectiveness of the above analysis techniques, the following discussion refers to the example of microscopic devices operating in human capillaries, where the vessel size, fluid velocity, and fluid kinematic viscosity result in a Stokes flow condition. It should be appreciated that the dimensions involved are related to the kinematic viscosity, and thus significantly larger vessel and device sizes could be used for more viscous fluids of interest. As discussed herein, for some industrial applications involving highly viscous fluids, devices could be many thousands of times larger. But, even for medical applications devices could be significantly larger than the example of Table 1 given the Reynolds number of <0.04, and that some biological fluids, such as blood plasma and lymph, have significantly higher viscosities than 1 mPaS.

Table 1 shows typical parameters for fluids and microscopic devices for the application of microscopic devices operating in capillaries. In some cases, the last column gives a range of values or approximate bounds rather than a single value. Values for the examples discussed in detail are within about a factor of two of these bounds. In the present example, Table 1 shows the Reynold's number for typical examples of flow parameters discussed in this section, which is much less than 1.

TABLE 1

| Quantity | Symbol | Value |
| --- | --- | --- |
| temperature | Tfluid | 310K |
| density | ρ | $10^3$ kg/m$^3$ |
| viscosity | η | $10^3$ Pa · s |
| kinematic viscosity | ν = η/ρ | 10−6 m2/s |
| vessel diameter | d | 5–10 μm |
| maximum flow speed | u | 200–2000 μm/s |
| Reynolds number | Re = ud/ν | <0.04 |
| device radius | r | 1 μm |
| device speed | vdevice | <u |
| device angular velocity | ωdevice | <u/r |

For the device motion considered here, with the parameters of Table 1, the resulting Womersley number (Eq. 2) is Wo<0.05, which is sufficiently small that quasi-static Stokes flow is a good approximation.

Passively-moving devices may be moved by fluid forces, gravity, and Brownian motion. For purposes of simplification, the devices in the present analysis are assumed to be neutrally buoyant in the fluid, so that the effect of gravity can be ignored. To evaluate the importance of Brownian motion in this example, the diffusion coefficient of a sphere is:

$$D = \frac{k_b T_{fluid}}{6\pi(eta)r} \approx 10^{-13} \text{ m}^2/\text{s} \quad (11)$$

with the parameters of Table 1, and where $k_B$ is Boltzmann's constant. The Peclet number:

$$P_e = \frac{r v_{device}}{D} \quad (12)$$

characterizes the relative importance of convective and diffusive motion over distances comparable to the device size. At the lower range of velocities for the specific numerical examples discussed, Vdevice 100 μm/s, the resulting Pe=1000, which is large compared to 1. Thus, diffusion is not important. The Peclet number represents the gradually decreasing importance of convective and diffusive motion for a particular size, and thus there is no distinct threshold at which diffusion becomes insignificant. But for example, for many purposes, Pe>100 will give adequate accuracy, and in more stringent cases, Pe>500 should assure that the effects of Brownian motion do not significantly impact the analysis. Lower Peclet numbers can be analyzed, just with the understanding that Brownian motion will increasingly add noise to the measurements as the number gets smaller (although this could be offset, e.g., by averaging multiple measurements).

The rotational diffusion coefficient of a sphere is:

$$D_{rot} = \frac{k_b T_{fluid}}{8\pi(eta)r^3} \approx 0.1 \text{ rad}^2/\text{s} \quad (13)$$

(Berg, "Random Walks in Biology," Princeton University Press, 1993) For the parameters of Table 1, $\omega_{device} \approx 100$ rad/s so for a change in orientation of θ=1 rad, $\omega_{device}/D_{rot} \approx 1000$, showing that rotational diffusion is not significant.

Since diffusive motion is relatively small over the times considered, the motion can be analyzed on the basis of assuming that such motion results entirely from the fluid forces on the device. For the time scales considered here, viscous forces keep the device close to its terminal velocity in the fluid (Purcell, "Life at low Reynolds number," American J. of Physics, 45, 1977). Thus, the device's velocity and angular velocity can be considered as the values giving zero net force and torque on the device.

The pattern of normal and tangential stresses on the device 100 shown in FIGS. 5A, 5B, 6A, 6B, and 8A, when moving through the vessel 102, were determined with the geometry and viewpoint of FIG. 2 and the further parameters set forth in Table 2, for purposes of illustration. This example, using the parameters given in Tables 1 and 2, is comparable to that of a micron-sized device moving in a small blood vessel such as a capillary. With radii of curvature of tens of microns (Gunter Pawlik, "Quantitative capillary topography and blood flow in the cerebral cortex of cats: an in vivo microscopic study," Brain Research, 1981), such vessels are approximately straight over the distances considered in the present example.

In this example, the fluid pushes the device through the vessel at 530 μm/s and with angular velocity −150 rad/s (i.e., clockwise rotation as viewed in FIG. 6A). The position tic marks shown on the axes in FIGS. 6A and 6B are in microns. The arrow lengths shown in FIG. 8A indicate the magnitude of the stresses at each of the 30 sensors, ranging from 0.8 Pa to 3.9 Pa.

TABLE 2

| Quantity | Symbol | Value |
| --- | --- | --- |
| device position | $y_c$ | 1.7 μm |
| vessel diameter | d | 6 μm |
| maximum inlet flow speed | u | 1000 μm/s |
| vessel segment length | — | 10 μm |

Direction to Wall and Direction of Motion Values

Evaluations for direction to the wall and direction of motion were modeled for device samples at various positions and orientations in vessels. Using variations of the situation show in FIGS. 2 & 4, a range of vessel diameters and flow speeds corresponding to small blood vessels were simulated. These samples employed parameters chosen uniformly at random according to the following criteria:

The maximum inlet fluid speed is between 200 and 1000 μm/s, equally likely flowing to the right or to the left. The vessel diameter is between 5 and 10 μm. The vessel segment length is between 18 and 20 μm. The position of device's center horizontally is within 2 μm of the middle of the vessel's length. The position of device's center vertically is between the center of the vessel and a minimum distance of 0.5 μm from the wall. Any device orientation was allowed (0 to 360 degrees).

The samples tested used 800 training and 200 test samples. The results from these samples showed mean magnitudes of error less than 1 degree for both the calculated direction to the wall and the calculated direction of motion, with the largest errors occurring for devices near the center of the vessel.

Position and Vessel Geometry Values

Training samples were also used to evaluate the device's position in the vessel and the vessel diameter; in this case, the training samples were used to fit regressions between these properties and the Fourier coefficients of the stresses. Only the first two principal components of the Fourier coefficients, for each of normal and tangential stresses, were used for evaluation in this example.

Specifically, principal components are linear combinations of the relative magnitudes of the Fourier coefficients, $m_{k,s}$ given in Equation (8). Specifically, the $h^{th}$ component has the form:

$$p_h = \Sigma_{k=1}^M \Sigma_s a_{h,k,s}(m_{k,s} - m\hat{}_{k,s}) \quad (14)$$

where $m\hat{}_{k,s}$ is the average of $m_{k,s}$ over the training samples and $a_{h,k,s}$ are weights, with values for the first two principal components given in Table 3, which provides weights for first two principal components (i.e., $a_{h,k,s}$ for h=1,2). For each component, weights for normal and tangential stresses are on the first and second lines, respectively.

TABLE 3

| k     | 1      | 2     | 3      | 4      | 5      | 6      |
|-------|--------|-------|--------|--------|--------|--------|
| h = 1 | −0.419 | 0.508 | −0.268 | 0.060  | 0.027  | 0.010  |
|       | −0.419 | 0.473 | −0.298 | 0.047  | 0.018  | 0.006  |
| h = 2 | 0.451  | 0.184 | −0.266 | −0.352 | −0.181 | −0.080 |
|       | 0.451  | 0.479 | −0.097 | −0.258 | −0.132 | −0.052 |

To evaluate relative position using the training samples, the relative position was related to the first two principal components of the Fourier coefficients, $p_1$ and $p_2$, by $$r.p. = 1/1 + \exp(-(\beta_0 + \beta_1 p_1 + \beta_2 p_2)) \quad (15)$$

where the $\beta_i$ are the fit parameters given in Table 4. These parameters were obtained from standard statistical models fit to the training data; such procedures are well known in the art, and are available in conventional statistics software (e.g., R, Mathematica, MATLAB).

TABLE 4

| Parameter | Value | Standard Error |
|-----------|-------|----------------|
| $\beta_0$ | −0.51 | 0.09           |
| $\beta_1$ | 3.3   | 0.3            |
| $\beta_2$ | −4.6  | 1.1            |

Using Equation 12, the vessel diameter in microns could be calculated using the parameters given in Table 5. The resulting root mean square (RMS) error was 0.51 μm, or within about 5-10% of the actual diameters considered in this example. The largest errors were for devices near the center of the vessel; e.g., the RMS errors were 0.9 μm and 0.3 μm for relative positions smaller and larger than 0.2, respectively.

TABLE 5

| Parameter    | Value | Standard Error |
|--------------|-------|----------------|
| $\beta_0$    | 1.66  | 0.01           |
| $\beta_1$    | 0.68  | 0.01           |
| $\beta_2$    | 4.05  | 0.06           |
| $\beta 1,1$  | 2.74  | 0.05           |

TABLE 5-continued

| Parameter   | Value | Standard Error |
|-------------|-------|----------------|
| $\beta 2,2$ | 11.0  | 0.4            |
| $\beta 1,2$ | −5.4  | 0.2            |

A calculated distance to the wall can be derived from the relative position of the device and the vessel diameter. In this example, as shown in FIG. 13, calculation error was largely dependent on relative position, with devices near the center of the vessel (relative position less than 0.2) having relatively high errors. Note that "high" error in this case is about 5-10% of vessel diameter, which is surprisingly accurate, but perhaps no more so than the fact that at larger relative positions, the predicted points generally fall almost exactly on the line, having average errors of about 2% or less.

TABLE 6

| Relative Position  | RMS Error in Distance to Wall |
|--------------------|-------------------------------|
| less than 0.2      | 0.5 μm                        |
| between 0.2 and 0.5| 0.2 μm                        |
| at least 0.5       | 0.05 μm                       |

Device Motion Values

For the cases considered here, angular velocities were typically about 100 rad/s, so a 5 ms measurement interval was selected to provide a change in orientation of less than one radian between measurement to avoiding aliasing. To evaluate angular velocity, the method discussed above of determining the angle $\Delta\theta$ by maximizing the correlation between the stresses before and after the motion was used to evaluate angular velocity using 100 of the test samples. The motion of each sample was evaluated for $\Delta t=5$ ms. The resulting predicted and actual values of the angular velocity for these samples is shown in FIG. 14 and the mean error for the calculated values was 0.51 rad/s (about 0.5% of the angular velocity).

Complex Vessel Geometries

The stress-based calculated values discussed above illustrate techniques that treat the simple case of a single spherical device moves passively with the fluid through a straight vessel. Using the samples of those cases as a basis, new analyses to calculate values for more complex situations can be created. One approach would be to modify the machine learning techniques described herein (many techniques would likely produce accurate results with the teachings herein to guide) for vessels with other shapes. An alternative approach is to apply the evaluation methods set forth for straight vessel to these more complex situations. Even though the resulting calculated values are almost certain to be less accurate, it is of interest to see how well the analysis process performs in situations for which it was not trained, so this latter approach is discussed below.

Figure 16:
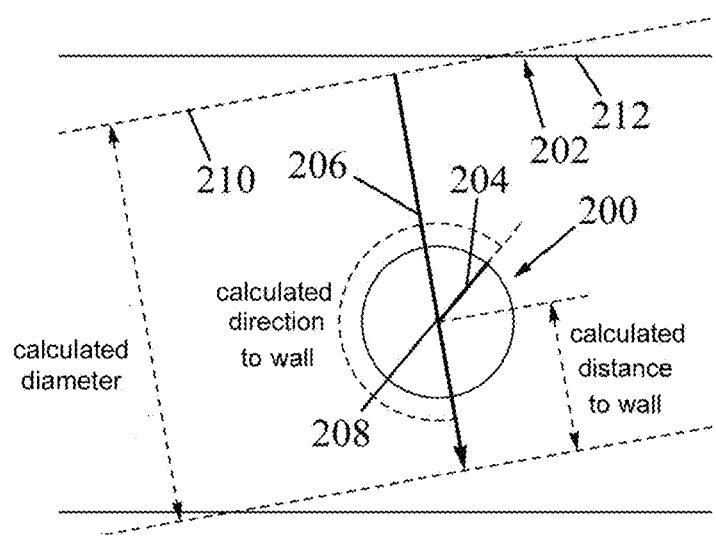
FIG. 16 provides a graphic representation of the calculated parameters for direction to the wall, vessel diameter, and distance to the wall, compared to the actual parameters.

In evaluating the use of these techniques, it is helpful to graphically show how inaccuracies can occur in the calculated values through the assumption of incorrect geometries (e.g., a straight channel being assumed when in fact it is not straight). The quality of the calculated values of the device's relation to the vessel can be graphically represented with an arrow through the device's center, as shown in FIG. 16. The calculated relation of a device 200 to a vessel 202 is indicated with respect to an orientation line 204 shows a relative "front" to index the orientation of the device 200. Solid calculated value arrow 206 through the device's center 208 graphically summarizes three calculated values: the direction and distance from the device's center 208 to the nearest vessel wall 210 (the calculated distance being indicated by the portion of arrow 206 from the device's center to the arrowhead), and the vessel's calculated diameter $D_{calc}$ (the calculated diameter being indicated by the total length of arrow 206). The actual vessel 202 has vessel walls 212, while the calculated values indicate the positions of calculated walls 210 indicated in dashed lines. In the particular example shown schematically in FIG. 16, the device 200 slightly underestimates both its distance to the actual wall 212 and the vessel's actual diameter. Perfect values would show the solid arrow 206 directed perpendicular to the vessel walls 212 and extending from one wall 212 to the other.

Curved Vessels

Figure 17:
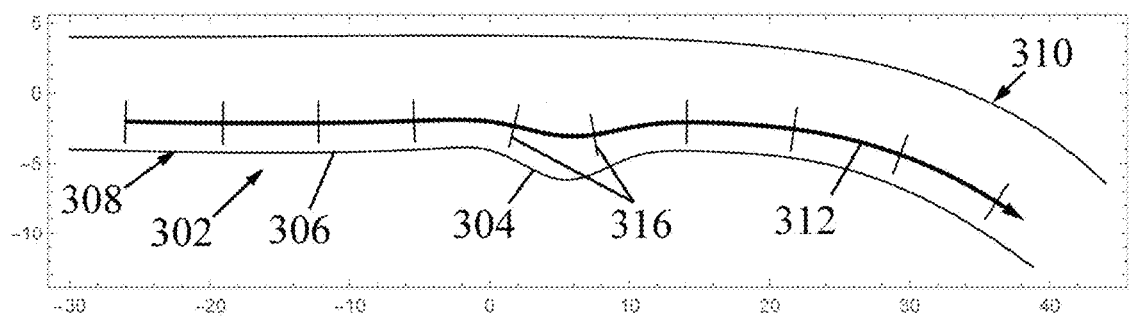
FIG. 17 illustrates the path of a device traveling passively through a vessel containing a straight section (with a discontinuity in the vessel wall) and a curve.
Figure 18:
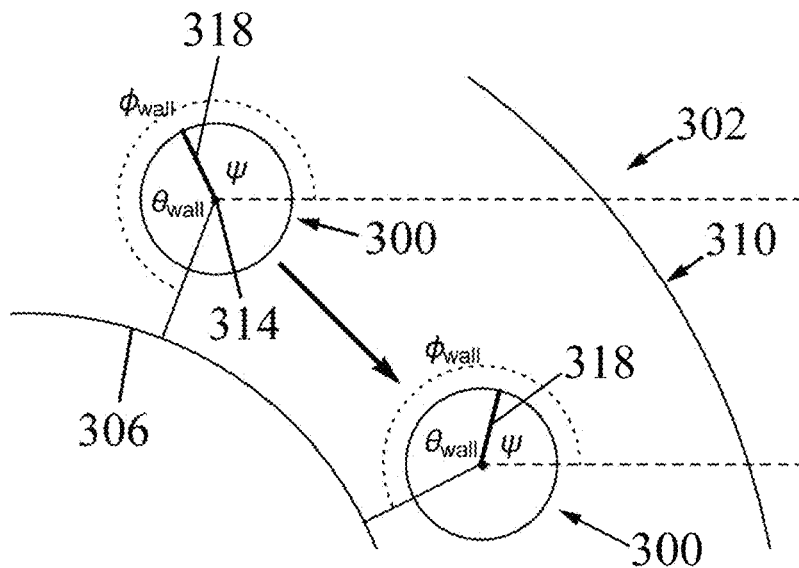
FIG. 18 illustrates the device when moving through the curve of the vessel shown in FIG. 17.

The following discussion examines how calculated values based on straight vessels perform as a device 300 as depicted in FIG. 18 moves through an exemplary curved vessel 302, such as illustrated in FIGS. 17 and 18. The vessel 302 has two types of curvature: a bump 304 (shown in FIG. 17) in the vessel wall 306 having a radius of curvature similar to the size of the device 300, occurring along a straight section 308, and a gradually-curved section 310, with a radius of curvature that is large compared to the size of the device 300. For the numerical examples discussed herein, the values used for analysis used a maximum inlet flow speed of u=1000 μm/s, and positions along the axes in FIG. 17 are represented in microns. These parameters can be significantly greater in scale when applying the present techniques to fluids having a higher viscosity. In FIG. 17, the curved arrow 312 shows the path of the device's center 314 (shown in FIG. 18), as fluid moves it through the vessel 302. Ticks 316 along the curve 310 indicate positions of the center 314 at various times.

Evaluating Angular Velocity

In FIG. 18, as the device 300 moves through the vessel 302, the stresses on the device 300 surface mainly change due to the device's rotation with respect to the vessel wall 306. In particular, the position on the surface of the maximum tangential stress generally faces the closest vessel wall 306. The direction to the wall 306 changes due to a combination of the device's rotation and the vessel curvature, as shown in FIG. 18. Specifically, $$\frac{d\theta_{wall}}{dt} = \frac{d\varphi_{wall}}{dt} - \frac{d(psi)}{dt} \quad (16)$$

where ψ is the device's orientation (indicated with respect to orientation line 318, shown in FIG. 18), and $\theta_{wall}$ and $\varphi_{wall}$ are respectively the angle to the vessel wall measured from the front of the device and measured from the x-axis (comparable to the same angles shown for the device 100 in FIG. 9). The first term on the right is due to the vessel curvature. The second term is $-\omega_{device}$, the negative of the device's angular velocity.

In general, measuring the change in stresses evaluates how rapidly the direction to the wall 306 changes with respect to the front of the device 300. Alternatively, $-d\theta_{wall}/dt$ is how rapidly the device 300 rotates with respect to the vessel wall 306, giving the rate of change of the orientation with respect to the wall 306. In a straight vessel, $-d\theta_{wall}/dt=\omega_{device}$ so the rate of stress change is directly proportional to the device's angular velocity. However, in a curved vessel, Eq. (16) shows this value has an additional contribution from the vessel curvature.

Figure 19A:
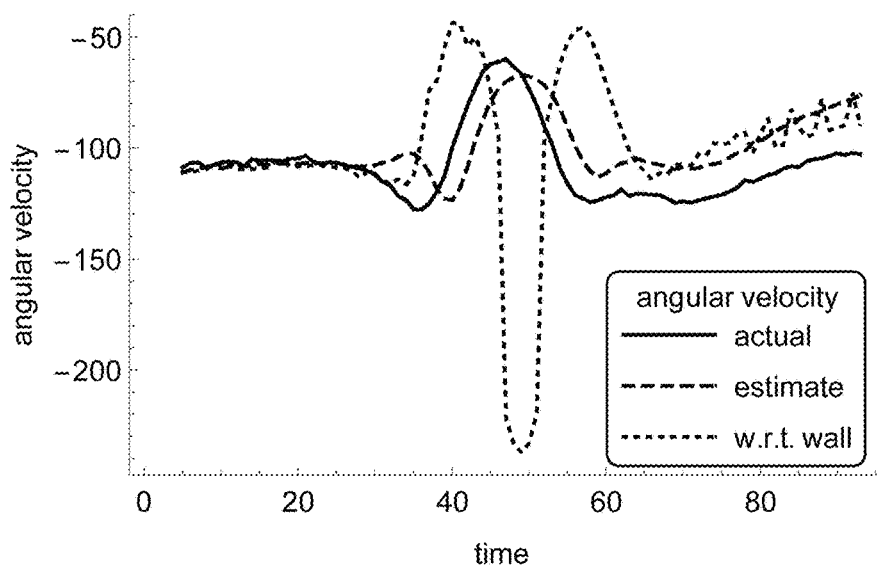
FIGS. 19A and 19B illustrate the difference in stress experienced due to a discontinuity versus a curve.
Figure 19B:
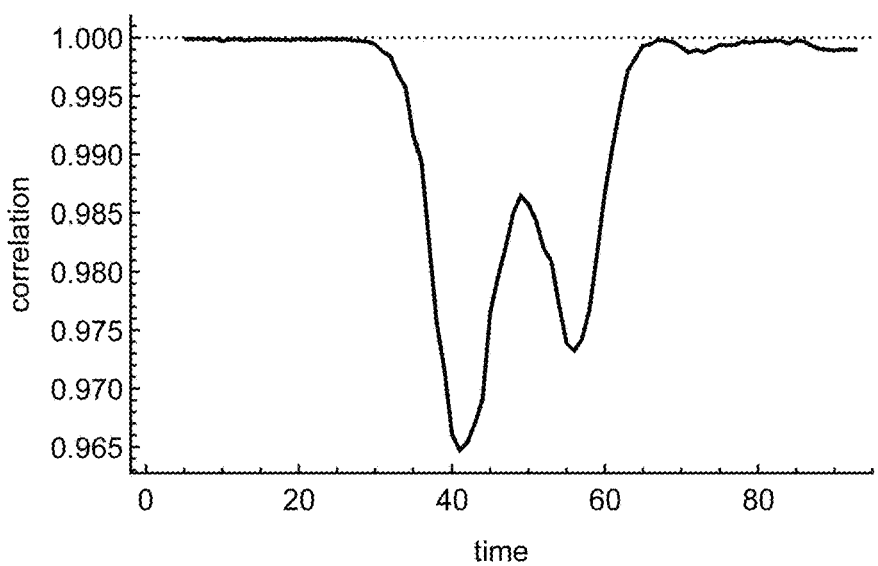

For a device moving through the curved vessel, FIG. 19A shows a comparison of the angular velocity, calculated from correlation over Δt=5 ms, with the actual value, $\omega_{device}$, where the calculation of angular velocity is made as described for a straight vessel. While the device 300 is in the straight portion 308 of the vessel 302, the calculated value is close to the actual value. The angular velocity changes as the device 300 passes the bump 304 in the vessel wall 306, and the calculated value tracks the change with a delay of about Δt. FIG. 19B shows the correlation between stress patterns separated by 5 ms (the time interval used to evaluate the angular velocity in this example).

In the slowly curving portion 310 of the vessel 302 (time after 60 ms), the calculated value for angular velocity deviates systematically from the actual value. This difference is because the evaluation procedure actually measures the rate of the device's orientation changes with respect to the vessel wall, i.e., $-d\theta_{wall}/dt$ from Eq. (16), rather than with respect to an external reference. To test this relationship, FIG. 19A also shows the average rate of change of the device's orientation with respect to the wall 306. This is close to the calculated value in both the straight section 308 and the gently curved section 310 of the vessel 302. As the device 300 passes the bump 304, the value deviates significantly from $-d\theta_{wall}/dt$, in part because the direction of maximum tangential stress deviates from the direction to the nearest point on the vessel wall (as seen in FIG. 20B). So in this case, large tangential stress is not an accurate indication of the direction to the vessel wall, and its change over Δt also gives an inaccurate value for $-d\theta_{wall}/dt$. Instead, for small, high-curvature bumps in the vessel wall, the calculated value more closely tracks the actual angular velocity.

FIG. 19B shows the drop in correlation of interpolated stress patterns as the device 300 passes the bump 304, indicating that the stress pattern is changing more than it would just due to device rotation in a straight vessel. This is useful information. The decreased correlation is an indication of an abrupt geometry change in the vessel. While a hypothetical bump 304 may be of relatively minor interest (though it at least provides a system feature for mapping) in this context, if it were a bulge in a high-pressure industrial pipe, or plaque in pipes or vasculature, this could be important information.

Evaluating the Device's Relation to the Vessel

Figure 20A:
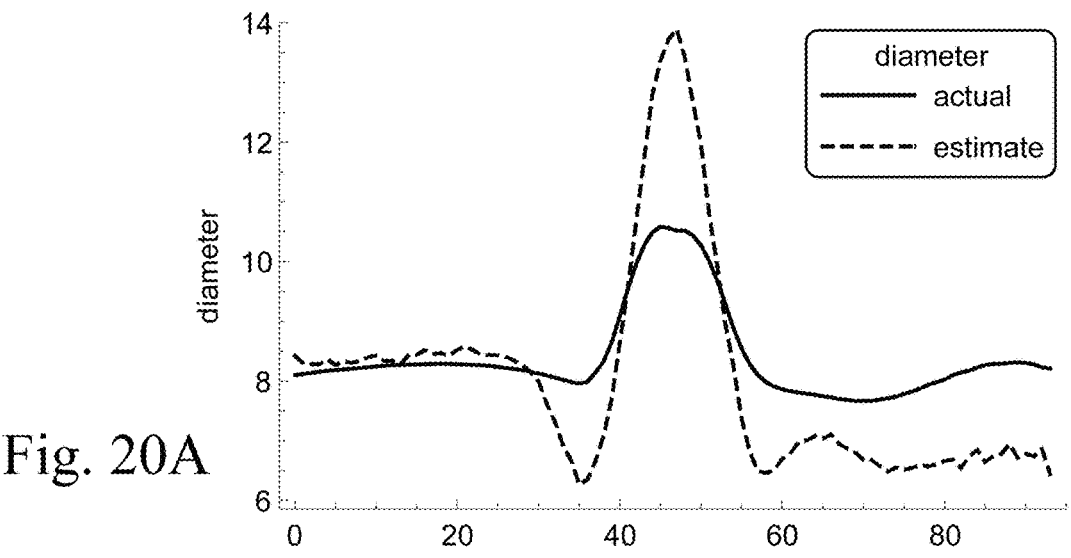
FIGS. 20A-20D are plots comparing actual and calculated values of parameters for the position of the device as a function of time as it moves through the vessel shown in FIGS. 17 and 18.
Figure 20B:
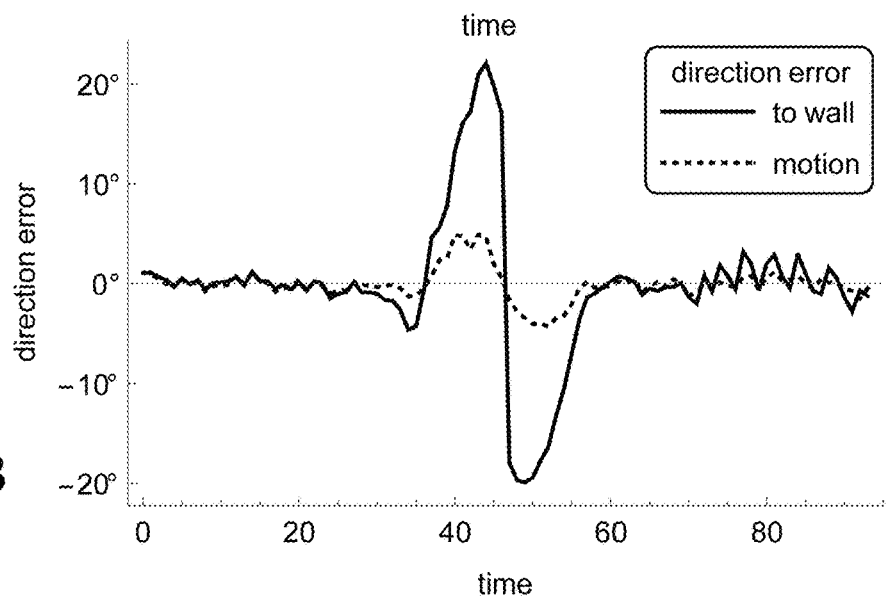
Figure 20C:
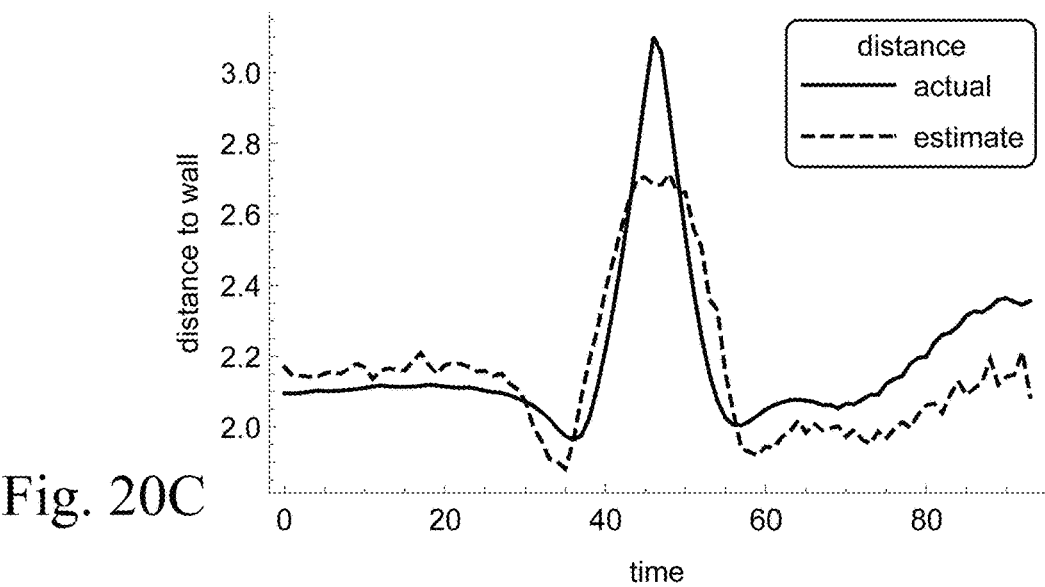
Figure 20D:
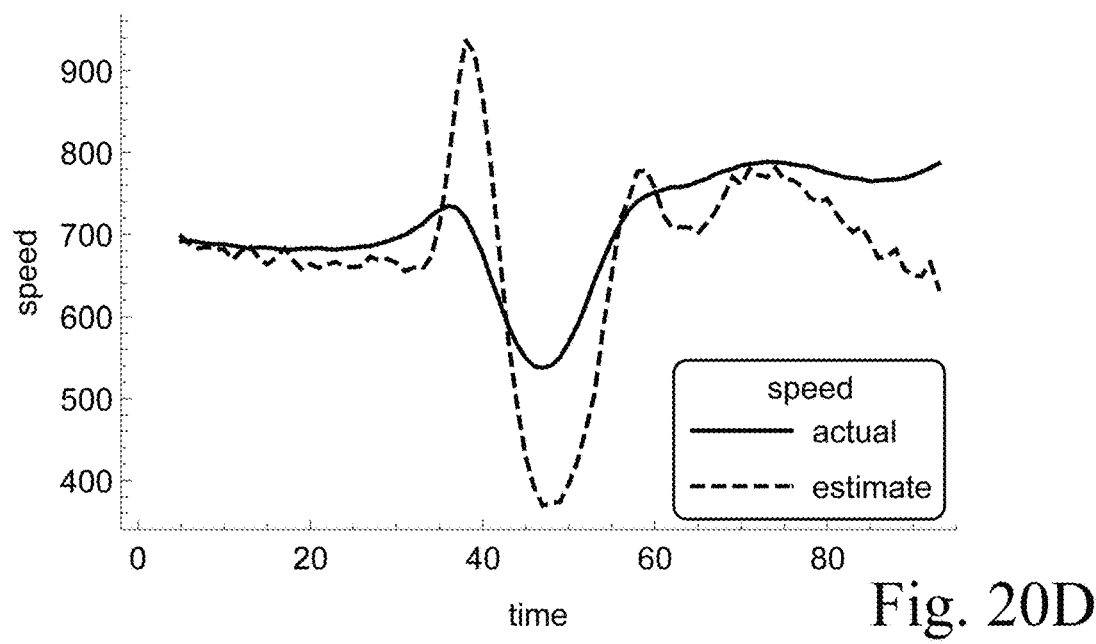

FIGS. 20A-20D show comparisons of actual and calculated values of information relating to the position of the device 300 and its relation to the vessel 302 as a function of time as the device 300 moves through the vessel 302 shown in FIGS. 17 and 18. The graph of FIG. 20A compares actual and calculated vessel diameter at the device's position. FIG. 20B shows the differences between the calculated and actual directions to the nearest point on the wall and the calculated and actual direction of motion. FIG. 20C compares the actual and calculated distance between the device's center and the nearest point on the vessel wall. FIG. 20D compares the actual and calculated speed at which the device 300 moves through the vessel 302. The calculated values are determined using the techniques discussed herein for a straight vessel.

The device 300 is in the nearly straight section 308 of the vessel 302 for the first 30 ms, and the calculated values are close to the actual values. During 35-55 ms, the device 300 passes the small bump 304 in the vessel wall 306, and the calculated values deviate significantly from the actual values. The fairly abrupt changes in the calculated values (not only alone, but in combination, since the relationships between the calculated values may change as well) allow the device 300 to identify when such changes in geometry occur. Finally, after about 60 ms, the device 300 moves in the gently curved section 310 of the vessel 300. The direction values (as shown in FIG. 20B) are quite accurate despite the curvature of this section, but the other calculated values have somewhat larger errors than in the straight vessel section 308. Overall, the calculated values give the device 300 a rough idea of its relation to the curved vessel section 310, and a clear signal that a change has occurred.

Of course, this is using machine learning algorithms trained for straight vessels on curved vessels. Obviously, appropriate retraining with data gathered from analogous vessels would yield higher accuracy. But, there is also a somewhat different method of handling such situations, which is by using classification techniques.

Branching Vessels

A bump or curve is one of the simplest possible geometry changes. Consider more complex cases such as where the vessel branches, or multiple branches merge. This is a common occurrence in fluid systems from vasculature, to microfluidics, to industrial piping. Such changes are important to device goals such as mapping and navigation, given that they are the fluid system equivalent of street intersections, highway on/off ramps, or other features common to roads.

In biological systems, the identification of such system features could aid in, for example, organ detection and discrimination (Augustin and Koh, "Organotypic vasculature: From descriptive heterogeneity to functional pathophysiology," Science, 2017) as well as tumor detection (Nagy, Chang et al., "Why are tumour blood vessels abnormal and why is it important to know?," British J. of Cancer, 2009; Jain, Martin et al., "The role of mechanical forces in tumor growth and therapy," Annual Review of Biomedical Engineering, 2014). In such cases, devices able to determine vessel geometry could supplement other available information, such as chemical concentrations, to more accurately identify different types of tissue.

Considering all these possible uses (and these are just examples, certainly there are more), the ability to detect branching or merging vessels is an important device capability. Some methods to detect where a vessel splits into branches, or when multiple vessels merge into a larger one, have been previously suggested. For example, acoustic detection seems possible (Freitas, "Nanomedicine, Volume I: Basic Capabilities," Landes Bioscience, 1999), though interpreting reflected signals could require significant computation in the presence of multiple reflections, scattering, and in some cases, the small difference in acoustic impedance between the fluid and walls, among other possible issues.

The approach taken here is that the detection of branches (in which we will include merges, which can be viewed as branches with the fluid traveling in the opposite direction) can be made based on measured changes in the patterns of fluid-induced stresses on their surfaces when the size, fluid speed, and fluid kinematic viscosity are such that a viscous flow regime exists.

Geometry of Vessels

For purposes of illustration, the following discussion again employs the parameters of the specific numerical example discussed herein for a spherical device of neutral buoyancy. These examples are used to evaluate device behavior in vessels with geometry comparable to that of short segments of capillaries, generally having radii of curvature of tens of microns (Gunter Pawlik, "Quantitative capillary topography and blood flow in the cerebral cortex of cats: an in vivo microscopic study," Brain Research, 1981). Typically, such vessels split into just two branches (CASSOT, LAUWERS et al., "A Novel Three-Dimensional Computer-Assisted Method for a Quantitative Study of Microvascular Networks of the Human Cerebral Cortex," Microcirculation, 2006), and the branches have a larger total cross section than the main vessel (Murray, "The physiological principle of minimum work: I. The vascular system and the cost of blood volume," Proceedings of the National Academy of Sciences USA, 1926), leading to slower flows in the branches (Sochi, "Fluid flow at branching junctions," International Jounral of Fluid Mechanics Research, 42, 2015). For simplicity, the examples discussed focus on planar vessel geometry, where incoming and outgoing axes of curved vessels are in the same plane, and where branching vessels have the axes of the main vessel and the branches in the same plane. Obviously, in many actual scenarios, the fluid system would not be planar, and this would actually help with goals such as mapping, because the off-plane angle could serve as an additional identifier to reduce ambiguity of similar sections of the fluid system. Such angle changes could be detected by the same methods we describe for classification of planar systems, and could also be detected by additional sensors, such as gyroscopes, providing additional data to confirm or increase the accuracy of inferences.

Figure 21A:
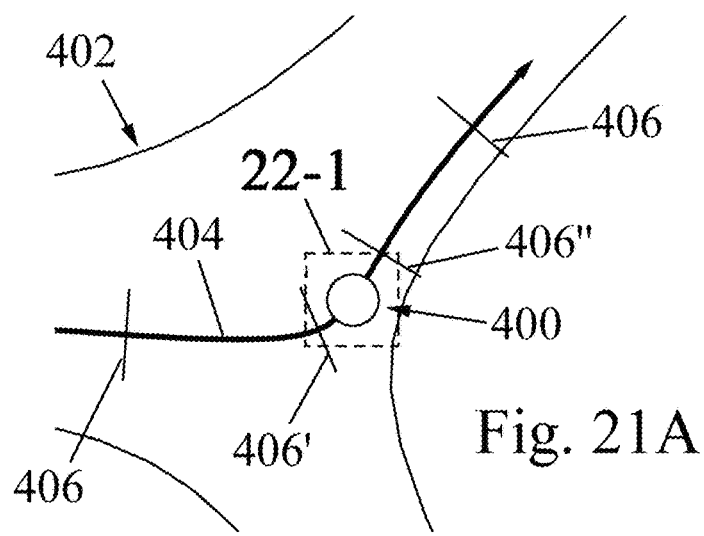
FIGS. 21A and 21B illustrate 2-dimensional analyses which are used to compare the stresses resulting from a device passing through a branched vessel (shown in FIG. 21A) versus passing through a curved vessel (shown in FIG. 21B).
Figure 21B:
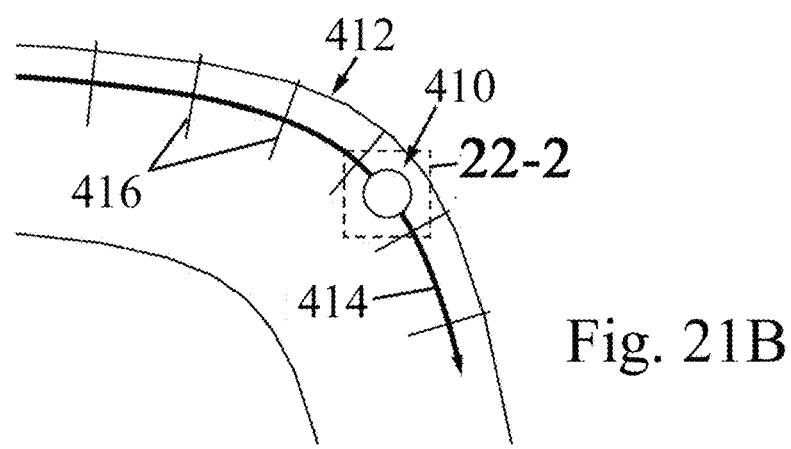

FIGS. 21A and 21B show examples of two vessel geometries considered, with FIG. 21A showing a device 400 moving through a branched vessel 402 and FIG. 21B showing a device 410 moving through a curved vessel 412 (similar to the device 300 and curved section 310 discussed with regard to FIGS. 17 & 18). In each case, the curved arrow (404, 414), shows a portion of the path of the device's center as it moves through the vessel (402, 412) with the fluid. The ticks (406, 416) along the paths indicate times (in milliseconds for this example) before or after the location of the device (400, 410). The dashed rectangle 22-1 of FIG. 21A indicates the part of the branched vessel 402 shown in FIGS. 22A-B. The dashed rectangle 22-2 of FIG. 21B indicates the part of the curved vessel 412 shown in FIG. 22C-D. The device (400, 410) in each case for this example has a radius 1 µm and the vessel inlets, on the left side of each vessel, both have diameters of 7.8 µm.

To simplify comparison, the fluid flow speed for these two cases is chosen so the devices (400, 410) have the same average stress magnitudes on their surfaces at the indicated position along each path (404, 414). Specifically, the maximum speed at the inlet is 1000 µm/s for the branched vessel 402 and 530 µm/s, for the curved vessel 412. At the position of the device 400 shown in the branch 402, the device 400 moves at 189 µm/s and rotates with angular velocity −34 rad/s, i.e., clockwise. For the device 410 in the curve 412 these values are 186 µm/s and +39 rad/s. Again, the values provided are exemplary, and other values would be appropriate for situations that have dynamic similarity, including much larger values where much more viscous fluids are considered.

Computational models of devices in branched and curved vessels were created to develop and test a branch classifier based on stresses on the device's surface. These models were used to generate data samples. Such data samples could also be obtained experimentally, e.g., by measuring forces on microfluidic devices (Wu, Day et al., "Shear stress mapping in microfluidic devices by optical tweezers," OPTICS EXPRESS, 2010). For this analysis, models of device paths were created for a range of vessel diameters and flow speeds corresponding to small blood vessels, with parameters given in Table 1. These samples are variations of the situations shown in FIGS. 21A and 21B, with parameters chosen uniformly at random according to: A maximum inlet fluid speed between 800 and 1000 µm/s. For curved vessels, a vessel diameter between 6 and 13 µm, and a bend angle, between direction of inlet and outlet, between 25 degrees and 75 degrees. For a vessel splitting into two branches, diameters of the branches, d1 and d2, were between 6 and 10 µm. The diameter of the main vessel, d, is determined from d1 and d2 according to Murray's law (Murray, "The physiological principle of minimum work: I. The vascular system and the cost of blood volume," Proceedings of the National Academy of Sciences USA, 1926; Sherman, "On connecting large vessels to small: The meaning of Murray's law," Journal of General Physiology, 1981; Painter, Eden et al., "Pulsatile blood flow, shear force, energy dissipation and Murray's law," Theoretical Biology and Medical Modeling, 3, 2006). The two branch angles were between 25 degrees and 75 degrees, and −25 degrees and −75 degrees, respectively. Vessel segment length extended 30 µm in each direction from the curve or branch. The initial position of the device's center was eight times the device radius from the vessel inlet, and randomly positioned between the vessel's walls with minimum gap 0.2r between the device surface and the wall. The device orientation was between 0 and 360 degrees.

From the initial device position, the device's motion through the vessel until it comes within 8 µm of an outlet was solved. Boundary conditions on the flow were a parabolic velocity profile at the inlet, no-slip along the vessel wall, and zero pressure at the outlet for a curve, or at both outlets for a branch. A total of 2000 samples created according to this procedure were studied, with 1000 for each vessel type (i.e., curve or branch). For each of these vessel types, 800 samples were used for training the classifier and the remaining 200 were used to test the classifier performance. The paths in these samples are about 40 µm in length. The fluid typically moved the device along the path in about 100 ms.

Device Stresses and Motion in Vessels

Figure 22A:
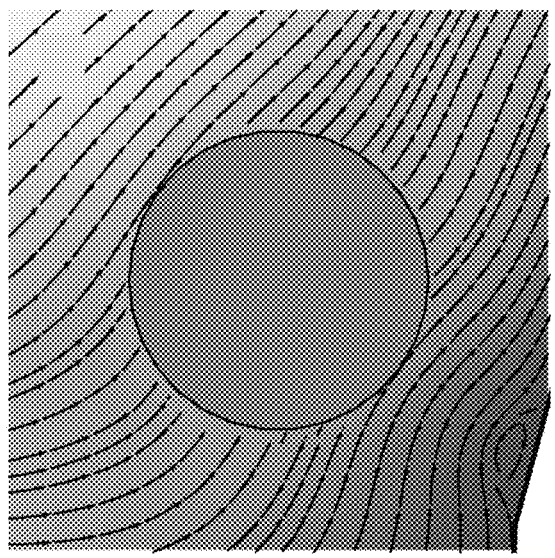
FIGS. 22A-22D illustrate the streamlines and fluid velocities for the device positioned in the branched and curved vessels as shown respectively in FIGS. 21A and 21B.
Figure 22B:
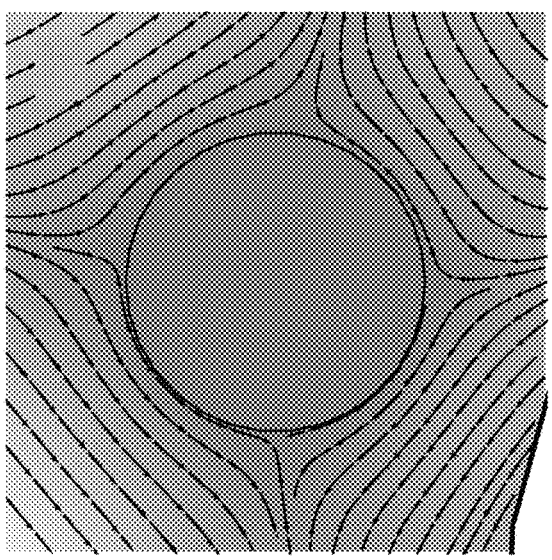
Figure 22C:
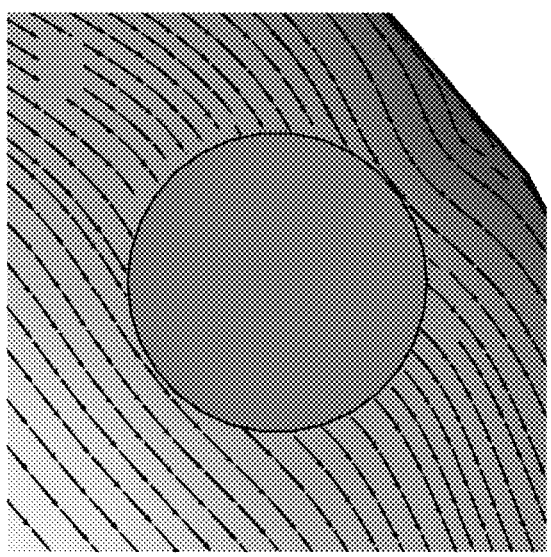
Figure 22D:
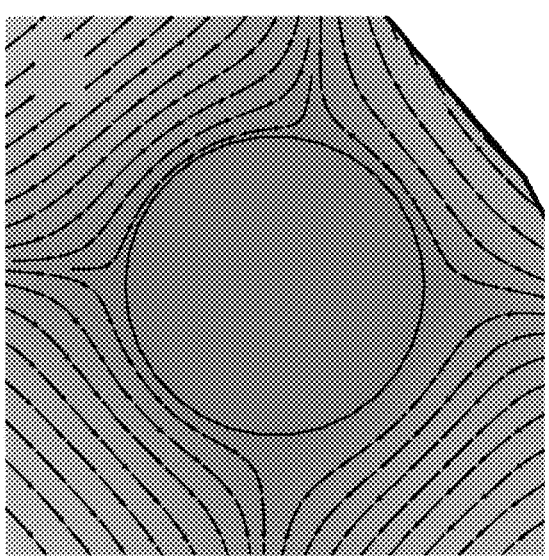

Stresses on the device surface can be determined by numerically evaluating the flow and device motion in a segment of the vessel. For the vessel sizes, planar geometries, and fluid speeds considered here, the motion and stresses can be approximated by two-dimensional quasi-static Stokes flow. As examples, FIGS. 22A-22D show the fluid velocity near the device, in the sections of the vessels indicated by the dashed rectangles 22-1 and 22-2 in FIGS. 21A & 21B, respectively. Despite the different vessel geometries, the flow near the device is similar in the two cases. In FIGS. 22A-22D, the arrows show streamlines of the flow and colors show the flow speed. FIG. 22A shows fluid velocity with respect to the vessel in the branched vessel case. Velocity is zero at the vessel wall, and matches the motion of the device at its surface. FIG. 22B shows fluid velocity with respect to the device in the branched vessel. Velocity is zero at the device surface. FIG. 22C shows fluid velocity with respect to the vessel in the curved vessel. FIG. 22D shows fluid velocity with respect to the device in the curved vessel.

Stresses on Device Surface

The stresses on a device's surface are denoted by $s(\theta,t)$ for the stress vector at angle $\theta$ at time $t$. The angle $\theta$ specifies a location on a device's surface, measured from an arbitrary fixed point on the device called its "front" (such as illustrated in FIG. 9). A device can evaluate $s(\theta,t)$ by measuring stresses at various locations on its surface with force sensors, and interpolating between these locations. By measuring forces normal and tangential to the surface, the sensors determine the stress vector.

Figure 23:
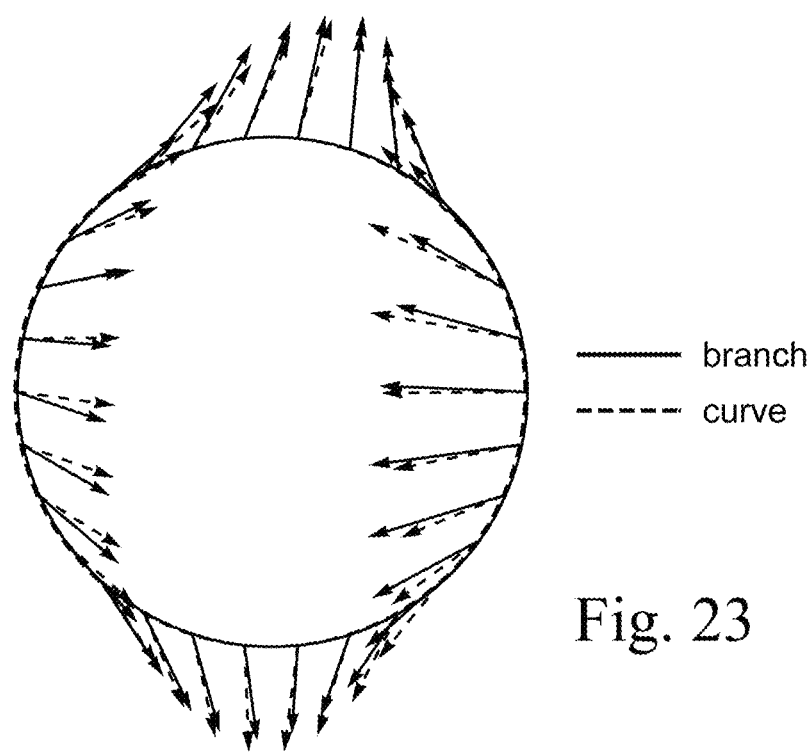
FIG. 23 illustrates the stress vectors relating to the flows shown in FIGS. 22A-22D, in a manner similar to the stress vectors shown in FIG. 8A.

The stresses depend on the vessel geometry near the device and the speed of the flow. However, this relationship may not be not unique: different geometries can produce similar stress patterns. FIGS. 21A & 21B provide one such example of similar stress patterns, as indicated by the diagram of stresses about the device shown in FIG. 23. FIG. 23 compares how stresses vary over the device's surface for the branched vessel and for the curved vessel, with the arrows indicating the stress vectors at points spaced uniformly around the surface (comparable to the illustration of stress vectors for a straight vessel as shown in FIG. 8A). The arrow lengths show the magnitude of the stresses, ranging up to 0.58 Pa, at locations of sensors on the device surface. The patterns of stress on the surfaces are nearly the same for the branched and curved vessels. Thus, in general, the pattern of stresses at a single instant does not reliably identify the geometry of the vessel near the device, and in such situations it is necessary to analyze changes in the stress patterns as the device moves to distinguish the cases. In use, continuous data collection is not needed; rather instantaneous "snapshots" of stress data at two or more time points can be used.

Changing Stress Patterns

As a device moves through a vessel with changing geometry, the stresses on its surface change. In many cases, the stresses change significantly as a device moves through a branch, whereas changes are fairly small as a device moves around a curve (as noted in the discussion of curved vessels), allowing these two cases to be distinguished from each other.

One measure of changing stresses is the correlation of the stress pattern at two times. For example, if $f(\theta)$ and $g(\theta)$ are two vector-valued functions of the angle $\theta$ around the device's surface. The correlation between these vector fields is:

$$cor(f, g) = \frac{1}{\|f\|\|g\|} \int_0^{2\pi} f(\theta) \cdot g(\theta) d\theta \qquad (17)$$

with the norm $\|f\|=\sqrt{\int_0^{2\pi} f(\theta) \cdot f(\theta) d\theta}$ and $f \cdot g$ denoting the inner product of the two vectors. In this case, the vector fields are the stresses on the device surface. As an example, the correlation between the surface stresses in the two cases shown in FIG. 23 is 0.98. Due to the normalization, the correlation is independent of the overall magnitude of the stresses. In particular, this means that the correlation does not depend on the fluid viscosity.

As noted, the device can evaluate the stress field $s(\theta,t)$ by interpolating surface stress measurements, and a particularly useful method is interpolating the stress pattern from a few Fourier modes. The correlation between two stress patterns can be computed directly from the Fourier coefficients, avoiding the need to explicitly evaluate the integrals in Eq. (17). As in the straight vessel example, the first six modes are analyzed, which is sufficient to capture most of the variation in stress over the device's surface for the cases considered herein.

When viewed from a fixed location on the device surface (such as a specific sensor), the stress changes both due to changing vessel geometry and due to the device's rotation caused by the fluid. For spherical devices, this rotation is not relevant for identifying vessel geometry, and thus the device must remove the component of change that is due to rotation of the device. One way to do so is to maximize the correlation over all possible rotations of the device between the two measurements used in the correlation. Specifically, this approach compares the stress at time t, $s(\theta,t)$, with shifted versions of the stress at a prior time, $s(\theta+\Delta\theta, t-\Delta t)$, and uses the maximum correlation over all shifts $\Delta\theta$. That is, the device measures changes in the pattern of stress that are not due to its rotation by evaluating:

$$c(t, \Delta t) = \max_{\Delta\theta} cor(s(\theta, t), s(\theta + \Delta\theta, t - \Delta t)) \qquad (18)$$

for the correlation function of Eq. (17). Another application of this maximization is evaluating the device's angular velocity because the shift in angle, $\Delta\theta$, giving the maximum as a value for how much the device has rotated between these two times.

Figure 24:
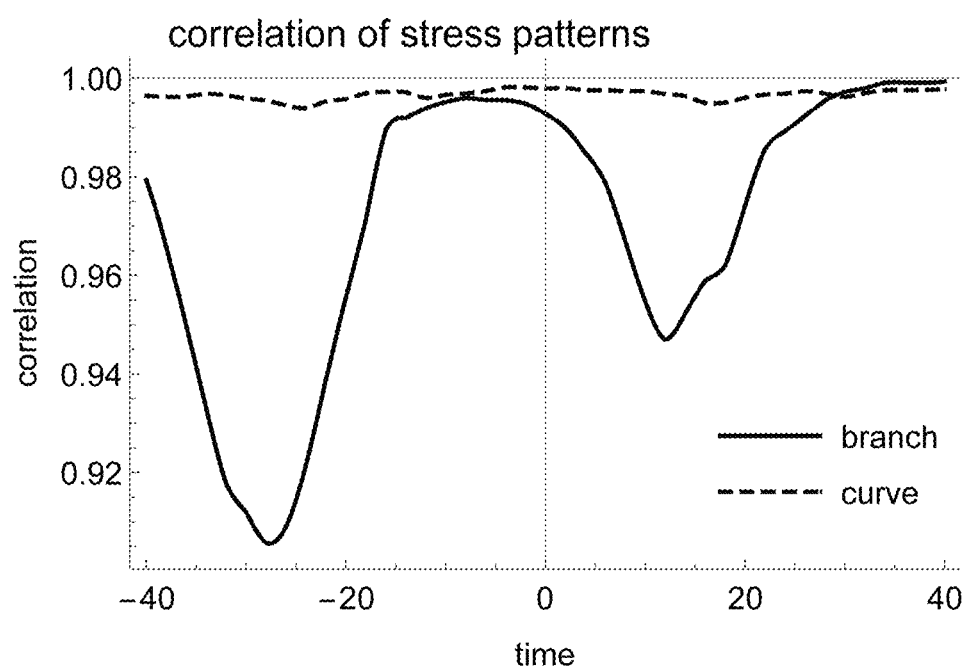
FIG. 24 is a plot that compares the correlation between stress patterns after a short time interval, for the device traveling through the branched vessel and curved vessel shown in FIGS. 21A & 21B.

Using the example of a micron-sized device in capillary-sized vessels, FIG. 24 shows the correlation between stress patterns separated by 10 ms as the device moves through the branch and curved vessels shown in FIGS. 21A and 21B. The times on the horizontal axis correspond to the tick marks along the paths shown in FIGS. 21A and 21B, with t=0 corresponding to the device positions shown in those figures. For the curve, the stress pattern remains nearly the same, so correlations are close to one. For the branch, however, the correlation drops as the device approaches the branch, about 30 ms before it reaches the position shown in FIG. 21A. Later, the correlation drops again as the device moves into one of the branches. Similarly, if the device were moving the opposite direction, i.e., the flow was a merge of two small vessels into a larger one, the device would encounter these drops in correlation in the opposite order and at times shifted by 10 ms as it compares its current stress pattern with the pattern it had encountered earlier along the reversed path.

For the flow speeds and vessel sizes considered here, $\Delta t=10$ ms is a reasonable choice, as it represents an interval during which a device can move a distance comparable to the extent of branching or curving, but not so far as to completely pass the changing geometry. However, the precise value of $\Delta t$ is not important. For example, comparing stresses separated by $\Delta t=5$ ms or 20 ms is qualitatively similar to the behavior shown in FIG. 24. For definiteness, we use $\Delta t=10$ ms in the following discussion. For more viscous fluids and larger device and vessel sizes, depending on device velocity, it is likely that substantially larger time intervals could be used.

Classifiers for Vessel Geometry

Figure 25:
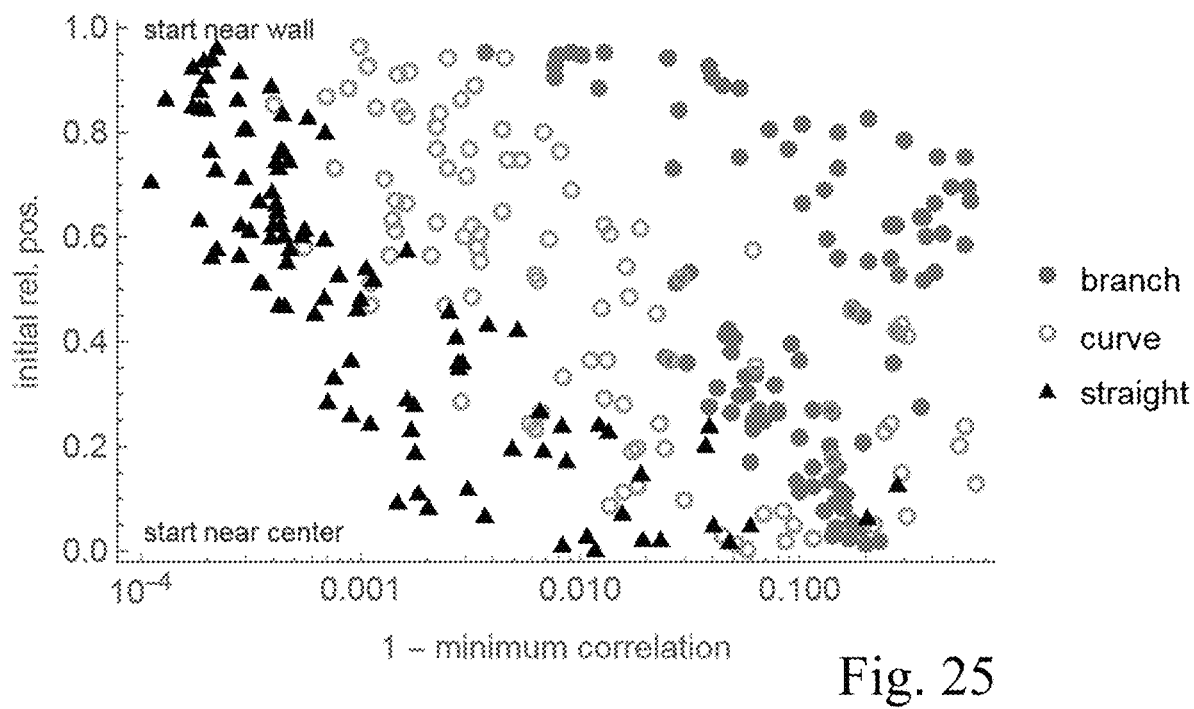
FIG. 25 is a plot of minimum correlation along the path of the device for devices traveling in either a straight, branched, or curved vessel, starting from different relative positions in the vessel. Unlike the plot shown in FIG. 10, where the values fall within distinct regions, in this case there is some overlap for devices that start near the center of the vessel.

The results shown in FIG. 24 suggests that a device can identify vessel branches by checking for when the correlation of stresses separated by a short time is sufficiently small. This procedure should reliably distinguish branches from curves if there is little overlap in the distributions of minimum correlations for these two geometries. Unfortunately, the behavior shown in FIG. 24 does not occur in all cases. Instead, the distributions of minimum correlation for curves and branches have considerable overlap, especially when the device is near the center of the vessel, as shown in FIG. 25, which is a scatterplot of the minimum value of $c(t,\Delta t)$ along a path (for $\Delta t=10$ ms) and initial relative position; this plot quantifies the difficulty caused by overlap in minimum correlation values, by showing how the minimum correlation along a path depends on how close the device is to the vessel wall before it reaches the curve or branch, i.e., while still in a fairly straight portion of the vessel. How close a device is to the vessel wall is given by the device's relative position (r.p.) from Equation (6), which can be calculated from instantaneous surface stresses when in a straight vessel. The points on the plot of FIG. 25 distinguish devices moving through a branch, around a curve, or along a straight vessel. To highlight the differences among these geometries, the horizontal axis shows 1−c on a logarithmic scale. Thus, situations where the stress pattern changes only slightly over time $\Delta t$ (i.e., correlations are close to 1), appear on the left side of the diagram.

In cases where the device starts near the center of the vessel, FIG. 25 shows that curved paths have a wider range of minimum correlations than branches, and this range includes the values occurring in branches. Combined with smaller, noisier stresses for devices relatively far from the vessel wall, this indicates correlation is not a reliable identifier of branches when devices start near the vessel center.

Identifying Branches from Stress Measurements

To improve identification for paths starting close to vessel center, additional information available to the device can be used. In one example of creating a vessel geometry classifier, a summary of the stress pattern at the time the device evaluates the correlation was used. That is, to identify branches, at time t, three pieces of information were employed in this example: the correlation $c(t,\Delta t)$, the relative position for the path that was determined prior to any significant change in the stress, and the current stress $s(\theta,t)$. Using this information, a set of training samples was generated. For each training sample (created as discussed above), the time t was determined along the path with the minimum correlation, and the three pieces of information from that time along the path were employed. This method is an example of off-line training; that is, the training samples are assumed to have measurements from a completed path (i.e., a path starting before the device reaches the branch or curve and continuing until the device is well past those changes). With measurements along the whole path, the time of minimum correlation can be obtained and values at that time used for training. Using such training samples from both branch and curve vessels results in the example of a logistic regression classifier for branches described herein. The parameters of the resulting model were then applied to evaluate the accuracy of the model.

Regression Classifier for Branch Detection

In the present example of a branch classifier, branches are identified using a logistic regression based on the three characteristics of the device's stresses along its path through a vessel: First, the correlation between the current stress and that of a short time earlier. Second, the device's relative position in the vessel evaluated during the device's most recent passage through a nearly straight section of the vessel. Third, a measure of the shape of the device's current stresses, specifically the first principal component of the Fourier coefficients of the stress pattern (as discussed for analysis of the stresses when moving through straight vessels).

The regression model for the probability of a branch, $P_{branch}$, is $$P_{branch}=1/1+\exp(-b(\log(1-c)rp,p_1)) \qquad (19)$$

where c is the correlation between changing stress patterns, defined in Eq. (18), rp is the relative position, defined in Eq. (6), $p_1$ is the first principal component of the stress pattern, and $$b(lc,rp,p_1)=\beta_0+\beta_1 lc+\beta_2 rp+\beta_{1,1} lc^2+\beta_{2,2} rp^2+\beta_3 p_1$$

where the β . . . are the parameters, given in Table 7, determined from the training samples.

TABLE 7

| Parameter | Value | Standard Error |
|---|---|---|
| $\beta_0$ | −0.8 | 0.7 |
| $\beta_1$ | −1.7 | 0.6 |
| $\beta_2$ | 9.0 | 1.8 |
| $\beta_{1,1}$ | −0.97 | 0.11 |
| $\beta_{2,2}$ | 6.8 | 2.3 |
| $\beta_3$ | 11.6 | 0.8 |

Training this regression used stress measurements along the complete path of each sample to identify the time with minimum correlation along the path. This "off-line" training corresponds to the situation after devices complete their paths, so stress measurements all along the paths are available for training. Specifically, for each training sample, rp is the relative position at the start of the sample path where, by construction, the device is in a straight vessel segment prior to reaching the curve or branch. Moreover, c is the minimum correlation along the path, i.e., the minimum value of $c(t,\Delta t)$ along a path, for $\Delta t=10$ ms. The branch and curve points in FIG. 25 are examples of these relative position and correlation values. Finally, the value of $p_1$ used for training is the principal component of the device's stress at the time of the minimum correlation.

Applying the Classifier to Identify Branches

The classifier described above was trained with the minimum correlation along a path. A device using the same method when applying the classifier would have to wait until it was sufficiently far past a changing geometry to be sure it had detected the minimum correlation along the path for that change. This off-line application of the classifier could be useful in reporting vessel geometry changes well after encountering them, e.g., to provide a description of the path leading the device to a target location.

The discussion below addresses the more demanding classification task of recognizing a branch near the time the device encounters it. This on-line or real-time classification allows the device to take action while still near the branch. In this case, a device uses the classifier by repeatedly evaluating Eq. (19) as it moves. During these evaluations, the correlation $c(t,\Delta t)$ is not necessarily the minimum correlation along the path: i.e., the device could encounter smaller values as it continues through the vessel. Thus, the device using this method is extrapolating beyond the values used for training.

The classifier uses the device's relative position in the vessel before it encounters a branch or significant curve. Thus, the device must save its calculated value for relative position, updating the value only while vessel geometry is not changing. A device could determine when this steady behavior occurs by checking when the correlations between stresses at various delay times $\Delta t$ are close to 1, and the pattern of stress on its surface is consistent with its presence in a straight vessel segment. When the device encounters changing geometry, it uses the saved value for its relative position when evaluating the classifier, i.e., Eq. (19). This procedure applies to typical capillaries (Gunter Pawlik, "Quantitative capillary topography and blood flow in the cerebral cortex of cats: an in vivo microscopic study," Brain Research, 1981) where significant geometry changes are separated by tens of microns, a considerably larger distance than the size of the devices small enough to pass through those vessels.

Figure 26:
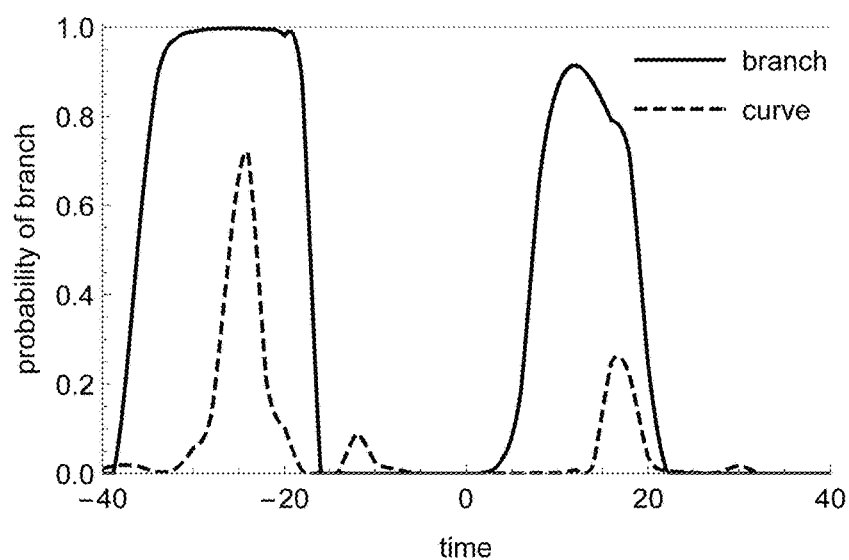
FIG. 26 is a plot showing probabilities of a branch being encountered, based on a classifier developed by analyzing the correlation of current stress on the device to a previously measured stress, the calculated relative position, and the first Fourier component of the stress pattern. A properly set threshold value for the probability can distinguish branched vessels from curved vessels.

As an example of how the classifier applies to on-line classification, FIG. 26 shows the values of $P_{branch}$ from Eq. (19) along the device paths of FIGS. 21A & 21B. FIG. 26 plots the calculated probability of encountering a branch ($P_{branch}$) vs. time as the device moves along the paths shown in FIGS. 21A & 21B, based on correlation $c(t,\Delta t)$ with $\Delta t=10$ ms. The branch path (shown in FIG. 21A) has higher values than the curved path (shown in FIG. 21B). This example indicates how a device could use the classifier for on-line branch identification, such as by considering a branch to be nearby whenever $P_{branch}$ exceeds a predetermined threshold. For this example, a threshold around 0.8 serves to distinguish the branch from the curve.

In addition to identifying whether the device passes a branch, FIG. 26 indicates when this method detects the branch. In this case for the branching vessel, $P_{branch}$ becomes large about 30 ms before the device reaches the location shown in FIG. 21A. This corresponds to the device entering the branch. The device slows as it moves through the branch, leading to a period of large correlation for about 20 ms. As the device leaves the branch, the stress pattern changes again, leading to a second minimum in the correlation (see FIG. 20) and another maximum in $P_{branch}$. In other cases, the device moves more rapidly through the branch, so the $\Delta t=10$ ms time difference used here gives a single minimum in the correlation and, correspondingly, a single peak in $P_{branch}$. A device could distinguish these cases by checking for a second peak within a few tens of milliseconds. Over that amount of time, the second peak indicates the device is leaving the branch rather than encountering a second branch. This is consistent with the typical spacing of branches in capillaries.

Selecting a Threshold to Identify Branches

A suitable threshold to use for identifying branches with the classifier discussed above depends on the relative importance of false negatives (i.e., missing a branch) and false positives (i.e., incorrectly considered a curved vessel to have a branch). The relative importance of these errors depends on the particular application. For example, if a device with locomotion capability needs to move into a branch, it is better to recognize a branch before passing it, so the device would only need to actively move a short distance to reach the desired branch. This contrasts with the situation of not recognizing the branch until well after the device has passed it, in which case it would need to move a larger distance, and move upstream against the flow of the fluid, expending greater energy reserves. In this situation, the device could use a relatively low threshold for branch classification, thereby being fairly sure it will identify branches as it encounters them, though it may also, incorrectly, attempt to move into a branch when passing through some curved vessels (in which case, at worst, the device may hit the vessel wall). Such errors are more likely the earlier the device needs to identify a branch because the flow well upstream of a branch is similar to that in vessel without branch.

Another action the device could take upon detecting a branch is to move to the vessel wall near the branch and act as a beacon to other devices arriving at the branch. The beacon signal could, for example, direct subsequent devices into one branch or the other to ensure roughly equal numbers explore each branch despite the fluid flow favoring one branch over the other. More generally, branches could be useful locations to station devices for forming a navigation network (Freitas, "Nanomedicine, Volume I: Basic Capabilities," Landes Bioscience, 1999). With a limited number of devices to form this network, and if it is sufficient to station devices at some rather than all branches, the device could use a high threshold of probability to ensure that branches identified by the classifier are very likely to actually be branches.

Other applications have less need for identifying branches while devices are close to them, but instead collect information on the number and spacing of branches for later use, e.g., as a map or diagnostic tool at larger scales than short segments of a single vessel. This applies to identifying vessel geometries that distinguish different organs or normal tissue from cancer tissue (Nagy, Chang et al., "Why are tumour blood vessels abnormal and why is it important to know?," British J. of Cancer, 2009; Jain, Martin et al., "The role of mechanical forces in tumor growth and therapy," Annual Review of Biomedical Engineering, 2014). In such cases, the emphasis could be on identifying all branches, favoring a relatively low threshold when approaching the apparent branch, and then verifying detected branches with subsequent measurements after the device has moved past each possible branch, thereby reducing the false positives while keeping sensor information obtained near the branches from the original identification of those cases that are later verified to be branches.

When multiple devices are employed, if spaced closely enough, devices passing a branch could communicate verified branch detections to devices upstream of the branch. With a message from a downstream device that it verified its recent passage of a branch, a device could lower its threshold in anticipation of that upcoming branch. The message could come from a downstream device that entered a different branch of the splitting vessel than the device receiving the message. For the example of micron-sized devices in capillaries or similarly-sized vessels, devices using acoustic communication could compare measurements over 100 μm or so (Hogg and Freitas, "Acoustic communication for medical nanorobots," Nano Communication Networks, 2012), which is farther than the typical spacing between branches in capillaries.

Verification After Passing a Curve or Branch

A device can use stresses to identify branches as it encounters them. This contrasts with off-line methods that collect time-stamped information before, during and after a device passes a branch, and later use the entire path history to identify if and when the device passed branches. A possible combination of the two approaches is to use on-line classification to identify likely branches, record information about them, and later verify the branch detection when the device has additional information after passing the possible branch. Information a device could use for this verification task includes indicated changes in vessel diameter, relative position, and/or device speed before and after passing the curve or branch. Typically, these changes are much larger after passing a branch than a curve. Specifically, when a vessel splits into branches, the branches have smaller diameter than the main vessel, but the combined cross sections of the branches is larger than that of the main vessel (Murray, "The physiological principle of minimum work: I. The vascular system and the cost of blood volume," Proceedings of the National Academy of Sciences USA, 1926). Thus, calculating values for vessel diameter before and after the branch gives a direct indication of branching.

The increased total cross sectional area after a vessel splits leads to slower flows in the branches (Sochi, "Fluid flow at branching junctions," International Jounral of Fluid Mechanics Research, 42, 2015), whereas flow in a curve remains nearly constant. This means that a device could also check for changes in its speed through the vessel before and after passing a detected branch or curve to verify the identification. However, slower fluid speed in the branch does not necessarily mean that the device's speed changes in the same proportion, because (as discussed herein when discussing evaluation of device speed) the device's speed depends both on the speed of the flow and how close the device is to the wall (i.e., its relative position). Along with flow speed, the relative position can change as a device passes a branch. However, as previously described for straight vessels, a device can normally accurately determine its distance from the vessel wall and its rate of rotation. Factoring these into any speed change detected makes this a useful test.

Figure 27A:
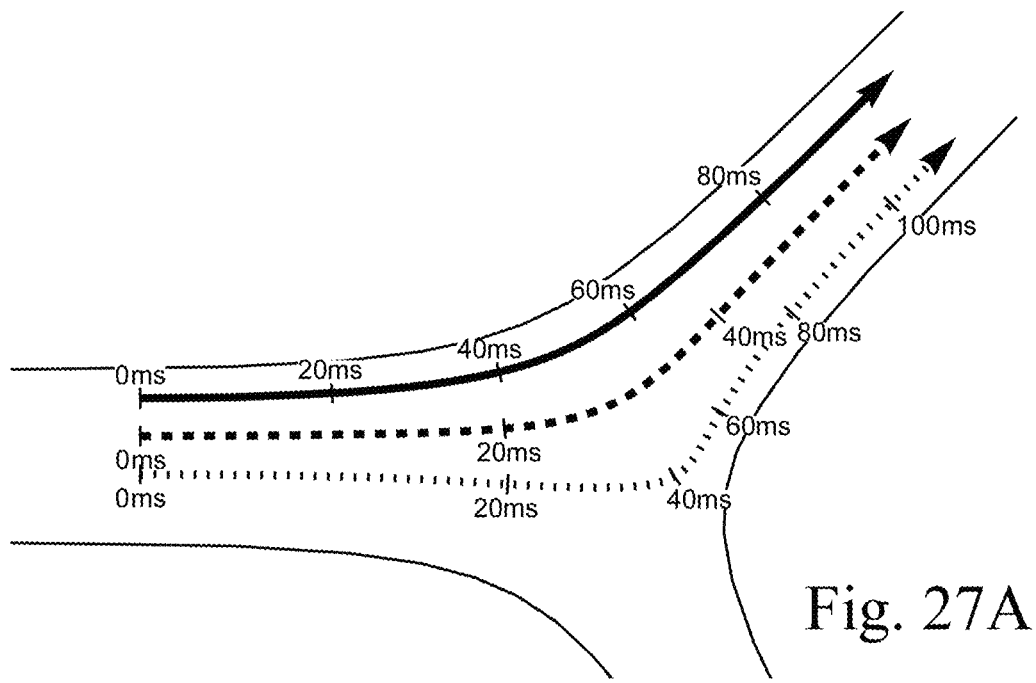
FIGS. 27A and 27B illustrate device paths through branched (FIG. 27A) and curved (FIG. 27B) vessels, starting from different relative positions.
Figure 27B:
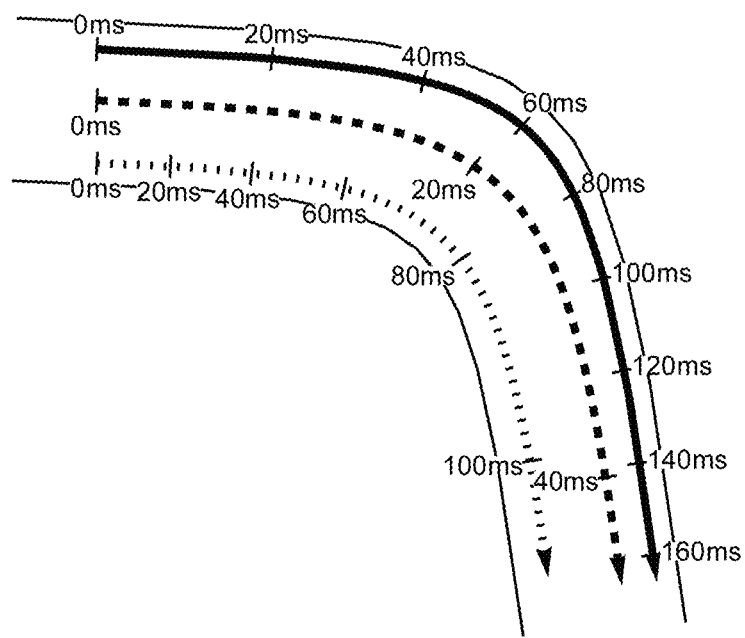

FIGS. 27A & 27B illustrate the behavior of devices passing through a branch (FIG. 27A) and a curve (FIG. 27B), starting at different relative positions in the vessel. Each path shown is for a device traveling by itself through the vessel, passively moved by the fluid flow. Again using the example of micron-sized devices in capillary-sized vessels, the ticks along the paths indicate times, in milliseconds, from the start of each path when the maximum inlet flow speed is 1000 μm/s. Devices along paths near the center of the vessel move more rapidly than those near the walls, indicated by the wider spacing between successive ticks along the central paths. The vessel inlets both have diameters of 7.8 μm.

Devices close the wall remain close upon entering a branch or moving around a curve. However, devices entering a branch near the center of the vessel move to near the wall of the branch, and devices starting between the center and the wall move to near the middle of a branch. This change in relative position can distinguish branching from curved paths in cases where the device is not close to the wall. Similarly, the change in speed is particularly large for branch paths when the device is not near the wall, so its speed reflects the decreasing flow through the branches. When the device is near the wall, in either a branch or curve, it moves relatively slowly and remains near the wall, giving relatively little change to distinguish between a branch and a curve.

Changes in relative position and speed are particularly useful for distinguishing curves and branches for paths near the middle of the vessels, precisely the cases where the correlation-based method (discussed with regard to FIG. 25) are least reliable. Moreover, the larger differences in these measures between curves and branches for paths near the center of the vessel could compensate, to some extent, for the lower accuracy when calculating position and speed from stresses when the device is near the center of the vessel.

Due to errors in evaluating position, speed, and vessel diameter from surface stresses, evaluating changes from a combination of these measures before and after passing a branch or curve is more robust than relying on a single method. Similarly, combinations of various sources of information are likely to be helpful in developing classification schemes for alternative vessel geometries.

Classification Performance

To evaluate the performance of the branch classifier example discussed herein, a set of test samples were studied. In the branch vessels considered in this example, the fluid flows from the larger vessel into the two branches, and thus testing the classifier with these paths evaluates how well a device recognizes when the vessel splits into two smaller vessels, with the device moving into one of them. The situation for flow merging from smaller branches into a larger vessel is similar, since a device at a given location in a vessel experiences stresses on the device surface that are the same for either direction of the flow, due to the reversibility of Stokes flow (Happel and Brenner, "Low Reynolds Number Hydrodynamics," The Hague, Kluwer, 1983). Thus, the stress measurements along a path are the same for paths through merging branches, but in the reverse order. For merging vessels, the classification operates in the same way as for splitting vessels, but with a shift of time $\Delta t$ in when the correlation is measured. For instance, for the device 400 at the location shown in FIG. 21A, the correlation $c(t,\Delta t)$ compares the stresses at the device's indicated location with the stresses when the device's center was at the point along the path 404 indicated by the tick 406' for −10 ms when using $\Delta t$=10 ms. Conversely, a device moving in the reverse direction along the path 404, i.e., from the branch at the upper right into the main vessel at the left, would compare its stress with that 10 ms earlier on the reverse path, corresponding to the location of the tick 406" for 10 ms on the forward path. Thus while stresses are the same along the forward and reversed paths, the comparison used for the correlation and the initial position in the vessel before encountering the branch are different for these two directions. When the device along the reverse path is at the position indicated by the tick 406' for −10 ms, it would compare stresses at the same two times that the device 400 on the forward path 404 does at the position indicated in the figure. So, a device on the reverse path computes the same correlations as a device on the forward path, but with a shift of $\Delta t$ in time. In this comparison, the devices use the same correlation in the classifier. But, because they are at different locations along the path when they evaluate that correlation, they would have different values for the other two values used in the present classifier example: the current stress and the initial relative position.

The classifier training employed for evaluation only included the forward direction for each branch, i.e., moving from a main vessel into one of the branches at a split. As a test of how well the classifier generalizes, each branch test sample was analyzed for higher pressure on the left (causing flow from left to right, thus experiencing a branch) and for higher pressure on the right (causing flow from right to left, thus experiencing a merge). A benefit of analysis under Stokes flow conditions is that the fluid flows are the same except for the velocities being reversed, and thus the stresses at any particular point along the path are the same in both cases.

Since the choice of probability threshold depends on the intended application, instead of characterizing a classifier for a single choice of threshold, a better general measure is the tradeoff between true and false positives over the range of threshold values. At one extreme, a threshold equal to one means the device never recognizes a branch (no true positives) but also never mistakenly considers a curve to be a branch (no false positives). At the other extreme, a threshold equal to zero means the device always considers itself to be encountering branches: this identifies all actual branches, but also mistakenly recognizes curves and straight vessel segments as branches (high false positives). For a perfect classifier, there would exist an intermediate threshold allowing it to identify all branches without also mistaking other vessel geometries for branches.

Figure 28:
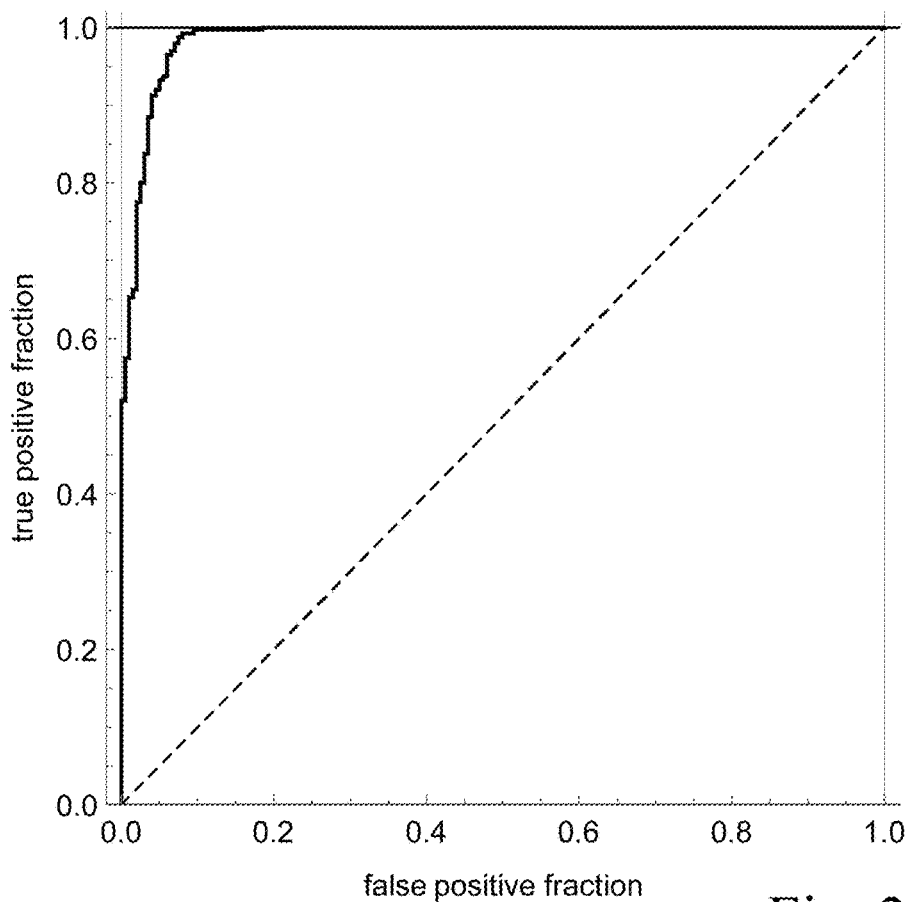
FIG. 28 is a plot illustrating branch classifier performance, plotting fraction of true positives against the fraction of false positives as the probability threshold value for the classifier is changed.

For the branch classifier example discussed herein, FIG. 28 shows the performance as the threshold varies from 1 (at lower left, where there are no true or false positives) to 0 (at upper right, all true and false positives). Specifically, for each threshold value, the figure evaluates $P_{branch}$ with Eq. (19) along the path of each test sample. If $P_{branch}$ exceeds the threshold anywhere along the path, that sample is classified as a branched vessel. The true positives are the branch samples identified as branches using that threshold, and the false positives are the curve samples incorrectly identified as branches. For comparison, the dashed diagonal line indicates how the plot would look if the classifier did not discriminate between paths through branched and curved vessels.

This example of a branch classifier performs well: with suitable threshold, the classifier recognizes most branches with only a few mistakes, as indicated by the curve in FIG. 28 passing close to the ideal behavior of recognizing all true positives and none of the false positives (i.e., the upper left corner of the figure). This tradeoff curve includes both forward and reverse paths. Examining performance separately for each direction (i.e., splitting or merging vessels) shows similar curves. Thus, there is no penalty for not including reverse paths when training the classifier. This is an indication of the robustness of the information used for this classifier, and the simplicity that results from the reversibility of Stokes flow.

A common overall performance measure for classifiers is the area under the curve. The area would be 50% for a classifier that made no distinction between branch and curve (as indicated by the dashed diagonal line in FIG. 28). 100% would be a perfect classifier. The area under the curve in FIG. 28 is 98.6%; this shows that the branch classifier performs very well for many situations, particularly in view of the minimal data and efficient use of CPU resources employed.

Figure 33:
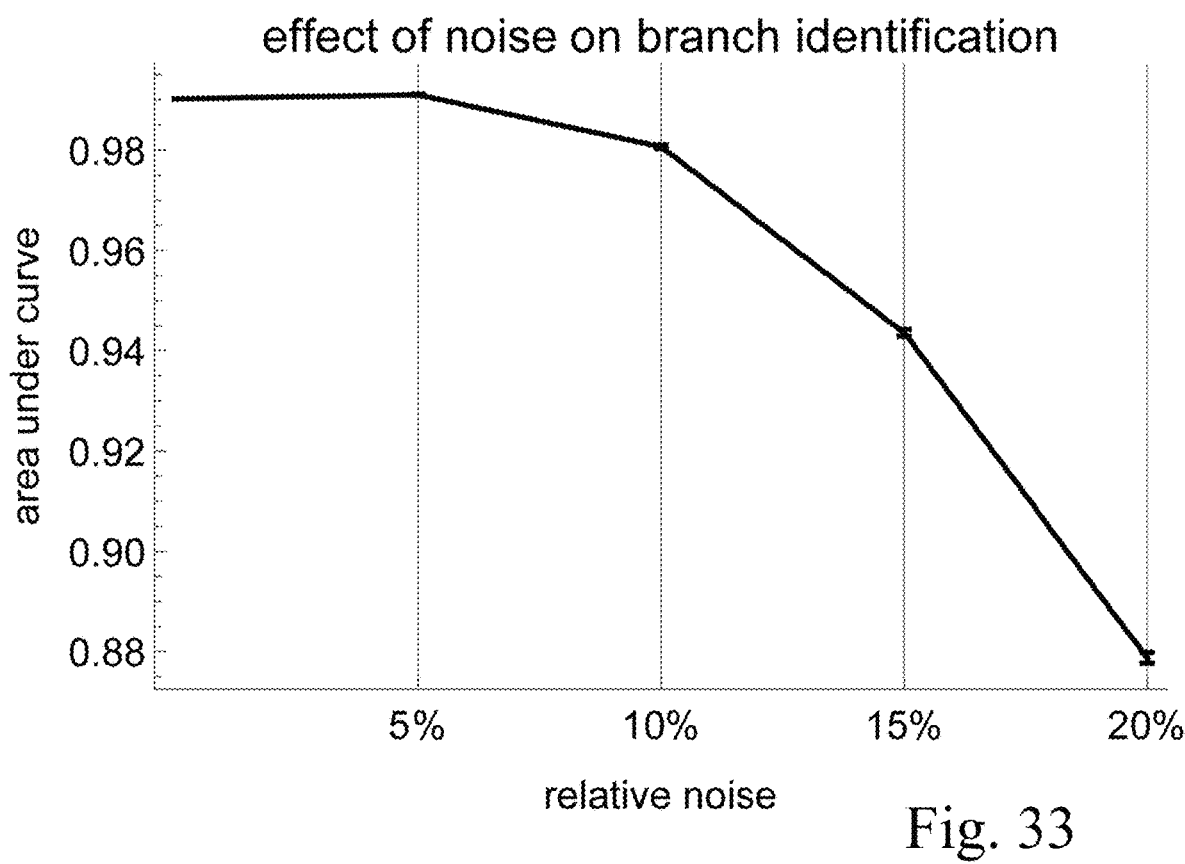
FIG. 33 is a graph evaluating the impact of signal noise on the classifier evaluated with reference to FIG. 28.

FIG. 33 shows the effect of sensor noise on classification accuracy, showing the reduction of the area under the curve shown in FIG. 28 for increasing amount of sensor noise that causes errors in measuring the stresses on the device caused by fluid forces. Up to 5% error in the sensor reading due to noise, noise makes almost no difference, and even at 10% error, it makes little difference (accuracy still above 98%), so these methods should be robust even to imperfect sensor data.

When Branches are Identified

In addition to how accurately this classifier example detects branches, an important performance measure is where along a path the device first detects a branch (i.e., whether the device detects the branch early enough to take action before passing the branch). One of the features this classifier uses is the correlation between stresses at the device's current location and those at the time $\Delta t$=10 ms earlier. Typically, stresses change the most as the device passes through the branch, and during 10 ms the device does not move significantly past the branch. This means the classifier typically detects the branch while the device is within the branching section of the vessel. Again, the time intervals selected for this example could be considerably larger when similar techniques are applied to larger devices and vessels employed with more viscous fluids.

Figure 29:
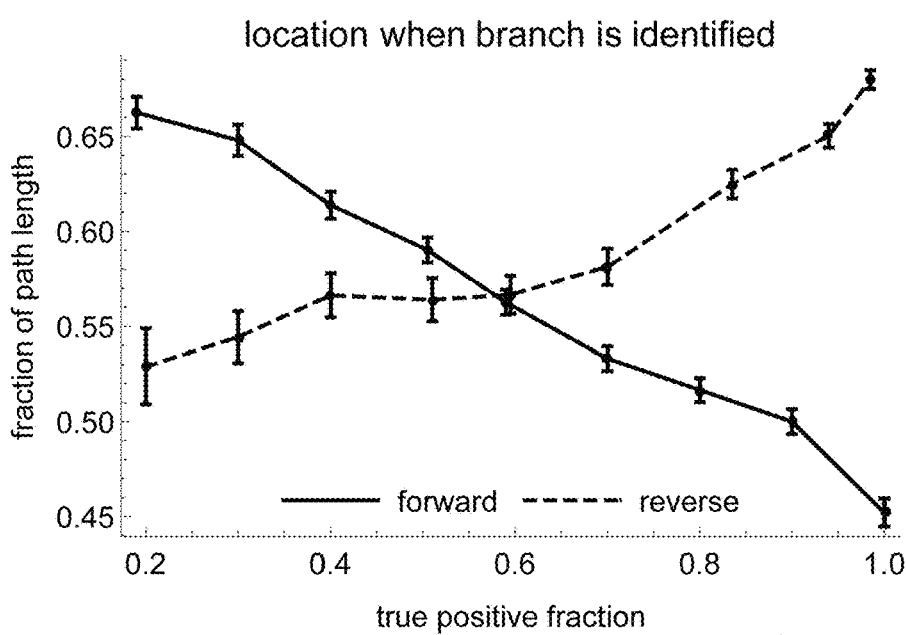
FIG. 29 is a plot illustrating fractional path length required for the classifier to exceed a particular threshold fraction of true positives, for both forward (from large vessel into branch) and reverse (from branch merging into larger vessel) paths.

FIG. 29 shows a plot of the fraction of path length of the test sample paths at which $P_{branch}$ first exceeds the detection threshold corresponding to the true positive fraction (indicated on the horizontal axis). The solid and dashed curves respectively show forward and reverse branch paths, and the error bars show the standard error of the means (indicated by the points). Quantitatively, FIG. 29 shows that this classifier generally identifies branches near the middle of the sample paths. This corresponds to when the device is close to the branch, rather than well before or after passing the branch; thus, this classifier identifies branches while the device is close to them, and a device can use this stress-based classifier to identify when it is passing a branch, well before it passes significantly downstream of the branch. On the other hand, branches are not identified well before the device reaches the branch. Thus, this particular classifier is not as useful for applications that require significant advance notice that the device is approaching a branch.

This classifier can detect most branches (high true positive fraction) with only a few false positives (as discussed with regard to FIG. 28). Thus, applications will likely use thresholds low enough to give true positive fraction above, say, 80% or so, corresponding to the right portion of FIG. 29. With this choice for the threshold, branch detection will generally occur at smaller fractions of the path length for forward paths than for reverse paths. This corresponds to a device moving toward a vessel split detecting the branch just as the main vessel splits. Conversely, a device moving in a vessel that merges with another to form a larger vessel will identify the branch just as the vessels merge. Quantitatively, the difference in path fraction for these two cases shown in FIG. 29 (about 0.15 for thresholds giving true positives above 80%—this is the difference in value between reverse value and forward value at the 0.80 position on the axis), corresponds to a difference of about 6 μm for the path lengths used here (with the parameters discussed herein). Thus the difference in where a branch is first identified for splitting or merging vessels is several times the device diameter.

Vessels Containing Multiple Objects

The above discussions address cases where the fluid moves a single device through the vessel. However, in many cases, vessels could contain additional objects, such as when multiple devices are employed, or when other objects are expected to be entrained in the fluid flow (in the numerical examples discussed herein, addressing vessels comparable to capillaries, blood cells would be typical objects in the fluid). The presence of objects in addition to the particular device under consideration can be considered as variation of vessel geometry. The following discussion illustrates examples of how the techniques described above, developed for a single device far from any other objects in the vessel, can be applied when other objects are nearby.

Vessels with Multiple Devices

In many applications, the use of multiple devices will be desirable to provide greater options in device operation, particularly when the devices communicate with each other to provide each device with more information than it can obtain individually. In some applications, devices could operate in close proximity, and occasionally devices may pass each other, such as when a device near the center of a vessel overtakes slower devices near the wall. Similar situations may arise in cases where other objects besides devices are moving in the fluid flow.

Figure 30:
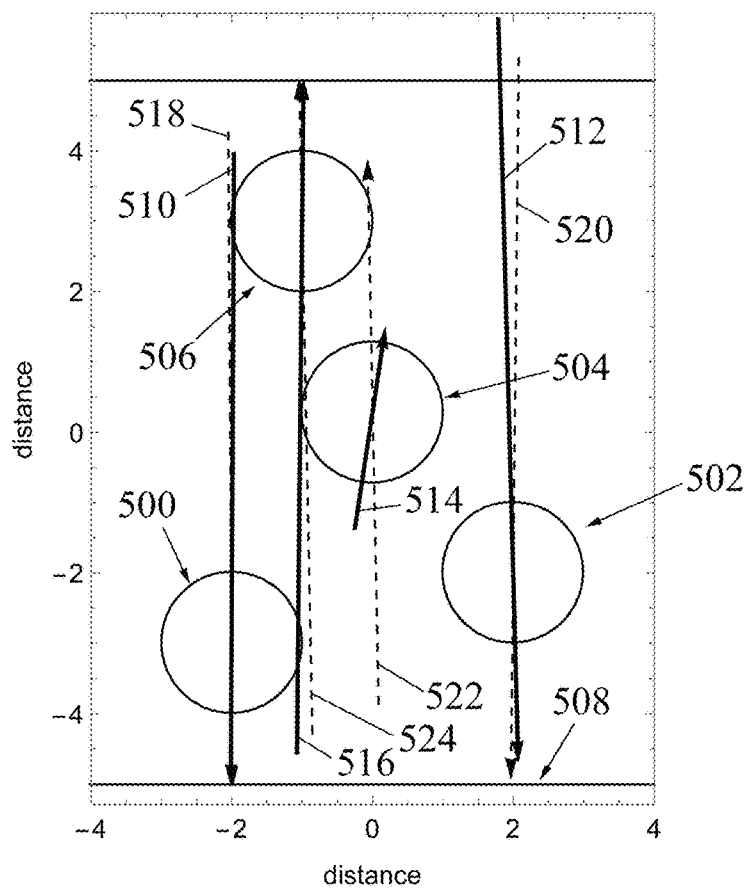
FIG. 30 depicts a graphic representations of calculated values (similar to the graphic representations discussed with reference to FIG. 16) for four devices in a vessel, showing one example of how the presence of other objects can affect the calculated parameters, particularly for a device positioned in the middle of the group.

As one example, FIG. 30 shows graphic representations of the calculated values (as discussed for device 200 shown in FIG. 16) for four devices (500, 502, 504, & 506) near each other in a vessel 508. Positions along the axes are in microns. Flow is from left to right. The solid arrows (510, 512, 514, & 516) through each device (500, 502, 504, & 506) indicate that device's calculated values, while the dashed arrows (518, 520, 522, & 524) are the corresponding calculated values that each device (500, 502, 504, & 506) would have at the indicated position, but if it were by itself in the vessel 508. Table 8 shows relative errors in the calculated values of speed and angular velocity for each device (500, 502, 504, & 506) in the group shown in FIG. 30, compared to the case if that device were by itself in the vessel at the same position. The angular velocity value in this example is from motion over Δt=5 ms leading to the positions shown in FIG. 30.

TABLE 8

| Device | Speed Group | By Itself | Angular Velocity Group | By Itself |
|---|---|---|---|---|
| 500 | −7.7% | −0.04% | 3.6% | −0.7% |
| 502 | −35% | −24% | 5.5% | −1.6% |
| 504 | 130% | −40% | −1050% | −3.3% |
| 506 | −6.5% | −2.0% | 6.2% | −3.0% |

Devices 500, 502, and 506 that are near the vessel wall 526 have similar calculated values with or without the other devices. However, the device 504 located in the middle of the group has significant inaccuracies in these calculated values. The device 504 could tell that it has inaccurate values, since the calculated values 514 indicate the device 504 is moving quickly in a narrow vessel; however, if that were actually the case, the device 504 should encounter large stresses, which would be about 40 times larger than the measured values in this case. Such small measured stresses are not plausible given that they would require the fluid speed or viscosity to decrease by that amount compared to prior measurements, before joining the group. This discrepancy in the readings can provide an indication of a discontinuity in the fluid flow, which could be caused by one or more nearby objects in the fluid flow and/or by a discontinuity in the vessel itself; the development of further classification options based on the methods taught herein, or obvious extensions thereto, will help devices to distinguish between different situations that cause discrepancies. Optionally, the device 504 could compare its measurements with the stresses communicated from the other devices (500, 502, 506), which are not consistent with high speed in a narrow vessel.

The devices (500, 502, 504, 506) could communicate to share calculated values, allowing the group to select the most reliable one, or combine calculated values. For example, one scheme would be to give more weight to devices that determine that they are close to the wall, where the evaluation methods discussed here are more reliable. Another scheme would be to give more weight to devices with higher correlation in their measurements over time.

Vessels with Cells Near the Device

Figure 31:
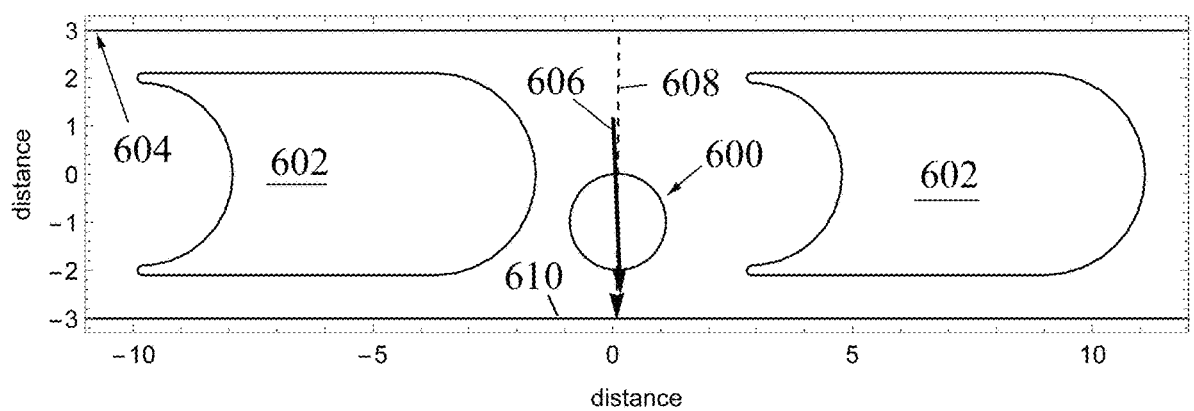
FIG. 31 is an illustration showing an example of a device in a vessel with additional objects; in this case, the vessel could be a capillary and the additional objects could be red blood cells (which can substantially deform in narrow capillaries, hence their geometric representation), however, as is true of all analyses herein, size scales and other specifics may vary greatly as long as the flow is still viscous.

Another example of additional objects in the vessel with a device occurs in the specific example of micron-sized devices in capillaries, where blood cells are likely to be encountered in the flow. Such cells typically deform as they enter capillaries and move through in single file. In such cases, devices will be in fluid between two cells, as shown in FIG. 31. In this example, a device 600 is positioned between two deformed blood cells 602 in a small vessel 604. Positions along the axes are in microns, and flow is from left to right. The solid arrow 606 through the device 600 indicates its calculated values (direction to wall, distance to wall, and vessel diameter as described with regard to the device 200 shown in FIG. 16). The dashed arrow 608 shows the calculated values that would result for the same device 600 in the vessel 604 if the blood cells 602 were not present.

The model for this example includes the distortion of cells 602 as they enter small vessels, including the resulting gap between the cells 602 and a vessel wall 610, but thereafter treats them as rigid bodies in their equilibrium shape, which can take a few tens of milliseconds to reach (Secomb, Hsu et al., "Motion of red blood cells in a capillary with an endothelial surface layer: effect of flow velocity," American J. of Physiology: Heart and Circulatory Physiology, 2001).

The device's position and relation to the vessel are calculated using the methods discussed herein, which were trained on a device in an otherwise empty vessel. The solid arrow 606 through the device in FIG. 31 shows that the device accurately evaluates the direction to the vessel wall 610 with only a small error, but significantly underestimates the vessel diameter, and thus also underestimates its distance to the wall. Table 9 compares actual and calculated device motion for the device 600, indicating the relative errors in the calculated values of device speed and angular velocity for the device shown in FIG. 31 compared to the values for a device at the same position in a vessel without the blood cells. The angular velocity value is from motion over $\Delta t=5$ ms leading to the position shown in FIG. 31.

TABLE 9

|  | Speed | Angular Velocity |
|---|---|---|
| with cells | 42% | 4.9% |
| no cells | 15% | −1.3% |

As indicated, angular velocity is evaluated well, but speed is significantly overestimated. In this case, the fluid moves the device a bit faster than the cells, so the device moves closer to the downstream cell. The device also moves toward the center of the vessel. As the device moves with respect to the cells, the errors in the calculated values are similar to those for the specific case shown in FIG. 31. Thus, the presence of cells near the device significantly affects the accuracy of the calculated values. Nevertheless, the calculated values remain within a factor of two of the actual values, thereby giving approximate values with simple analyses. Given the teachings herein, how to perform more accurate analyses for this, and other cases, would be obvious to one skilled in the appropriate arts.

More Complex Device Geometry and Motion

The discussion above addresses illustrative cases where the devices are spherical and move passively through the vessel. As with the more complex cases of curved and branching vessels, analysis of stresses may be more complicated in other scenarios, such as the case where the devices are elongated rather than spherical, cases where the devices are actively moving rather than passively being carried by the fluid flow, and/or cases where the devices are not neutrally buoyant in the fluid and thus gravitation forces must be considered.

Elongated Devices

In the discussion of spherical devices, the stresses do not depend on the device's orientation. However, other shapes of devices are likely to be advantageous in many cases. For example, elongated shapes could be useful for detecting chemical gradients (Dusenbery, "Living at Micro Scale: The Unexpected Physics of Being Small," Cambridge, Mass., Harvard University Press, 2009) and for locomotion (Hogg, "Using surface-motions for locomotion of microscopic robots in viscous fluids," J. of Micro-Bio Robotics, 2014). The pattern of stress on an elongated device changes as it rotates, typically alternating between relatively long periods with its long axis nearly aligned with the flow and short flips (Dusenbery, "Living at Micro Scale: The Unexpected Physics of Being Small," Cambridge, Mass., Harvard University Press, 2009).

To apply the analysis techniques discussed herein to elongated devices, the interpretation of quantities involved in the evaluation procedures, which use normal and tangential components of the surface stress, can be generalized. For the spherical devices discussed previously, these components not only describe the relation of the stress vector to the surface, but also correspond to forces directed toward and perpendicular to the center of the device. Only the latter forces apply torque around the center. For an elongated shape, these are different decompositions of the stress, e.g., stress normal to the surface is not always directed toward the center, and so can contribute to torque. Either of these vector decompositions, or other choices, may provide useful generalizations for elongated devices. For definiteness, the analysis discussed below uses both the normal and tangential components of the stress on elongated devices.

Figures 32A, 32B, 32C:
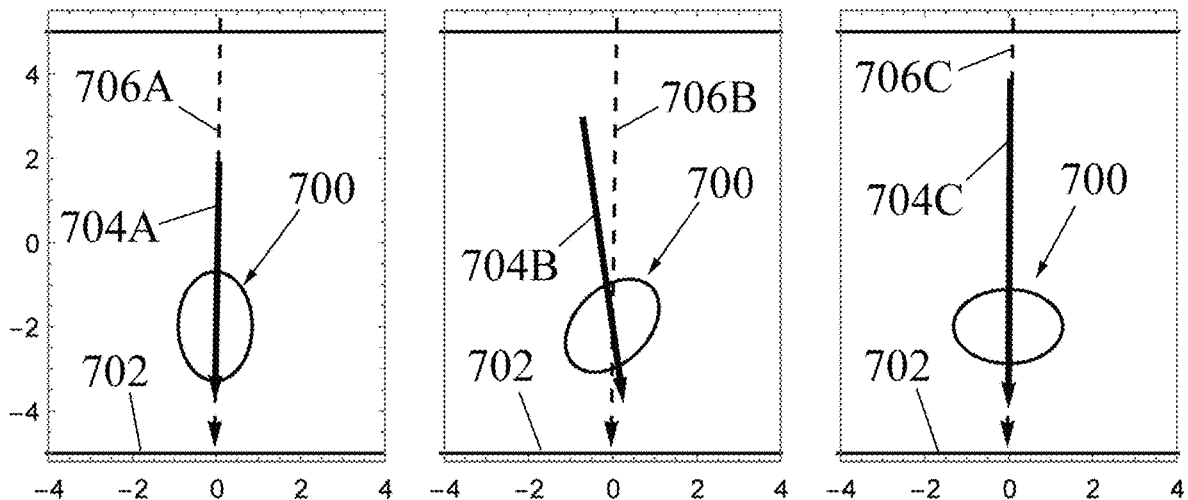
FIGS. 32A-32C illustrate graphic representations of values for a device that is ellipsoidal, rather than spherical. The calculated values change as the device moves with a tumbling motion, from a position with its semi-major axis perpendicular to the vessel wall (FIG. 32A), to a 45° angle (FIG. 32B), to a position where the semi-major axis is parallel to the wall (FIG. 32C).

As one example, a prolate spheroid can be employed, as shown in FIGS. 32A-32C, which show a two-dimensional representation of a device 700. For ease of comparison, the device 700 can be dimensioned to have the same volume as the spherical 1 μm-radius devices (100, 200, 300, etc.), with its semi-major axis a=1.3 μm and semi-minor axis $b=r^{3/2}/\sqrt{a}$. The aspect ratio of this spheroid is a/b=1.5. FIGS. 32A-32C show the device 700 at various orientations, and how the calculated values (using the methods developed for spherical devices, with particular reference to the graphic representation of calculated values shown in FIG. 16) perform for the elongated shape of device 700. Positions along the axes are in microns, and flow is from left to right. The figures illustrate different orientations of the device 700, the front of which is taken to be along the semi-major axis; thus, FIG. 32A shows the device 700 when its semi-major axis is 90° to the axis of the vessel 702, FIG. 32B shows the semi-major axis at 45° to the vessel axis, and FIG. 32C shows the semi-major axis parallel to the vessel axis. Solid arrows (704A, 704B, & 704C) through each view of the device 700 indicate the device's calculated values, while the dashed arrows (706A, 706B, & 706C) show the calculated values for a spherical/circular device with 1 μm radius at the same position.

In FIGS. 32A-C, the calculated relative position gives the position of the device's center, $y_c$, via Eq. (6), by generalizing the radius of the spherical device to be the minimum distance between the device's center and the wall in the calculated direction to the wall, i.e., the distance at which the device would just touch the wall. Table 10 shows the relative errors in the calculated values of device speed and angular velocity for the device shown in FIGS. 32A-C compared to a circular device at the same position. The angular velocity value is from motion over $\Delta t=5$ ms leading to the positions shown in FIGS. 32A-C.

TABLE 10

| shape | orientation | speed | angular velocity |
|---|---|---|---|
| ellipse | 90° | −32% | −0.7% |
| ellipse | 45° | −44% | −1.6% |
| ellipse | 0° | −65% | −3.3% |
| circle | all values | −2.0% | −3.0% |

Similar analyses could be performed for alternative device shapes.

Device Locomotion

The examples discussed above address devices that are passively moved through the vessel by the fluid flow. Devices with locomotion capability, allowing them to actively move through the fluid, may be desirable in many cases, such as to use chemical propulsion (Li, Esteban-Fernandez et al., "Micro/nanorobots for biomedicine: Delivery, surgery, sensing, and detoxification," Science Robotics, 2017) to improve in vivo drug delivery. Locomotion alters the stresses on the device surface compared to passive motion with the fluid.

To account for changes in stress due to locomotion, one approach for locomoting devices is to directly use the stress patterns they encounter. Like other alternative scenarios, this may involve training new evaluators based on stress patterns that occur when the device activates its locomotion with various speeds and patterns (e.g., faster motion on one side of device to change its orientation). The device would select among these trained evaluators based on the current state of its locomotion. This state could be specified in various ways, such as by how rapidly the device moves its locomotion actuators (e.g., treadmills, flagella, cilia, etc.), or by how much force or power the device applies to its locomotion actuators. While this approach is likely the most accurate, it requires extensive additional training over the range of locomotion patterns and values the device will use.

Another approach to handling locomotion is to vary the locomotion speed in such a way that the device can continue to use evaluators based on passive motion in the fluid. Two methods for this approach are briefly discussed.

One approach is to occasionally turn off the locomotion. The fluid quickly reverts to passive flow (e.g., in nanoseconds for micron-sized objects, such as micro-devices and bacteria (Purcell, "Life at low Reynolds number," American J. of Physics, 45, 1977). Thus, in brief periods with no locomotion, the device can measure stresses corresponding to passive motion. The measurement time required with no locomotion depends on the stress magnitudes and sensor noise. This method is most appropriate when this time is short compared to significant passive drift by the device while its locomotion is off.

Another approach is to exploit the linear relation between speeds and stresses in Stokes flow (Kim and Karrila, "Microhydrodynamics," Dover Publications, 2005) when the geometry does not change. For example, the device could measure stresses with locomotion at twice and at half the intended speed, and linearly extrapolate the stresses to obtain the values that would result for zero locomotion speed. This gives the device the stresses it would measure if it were moving passively with the fluid, without needing to turn off locomotion completely. The accuracy of this approach requires there to be negligible change in geometry during this procedure, both for the device and its environment. In particular, this requires that activating the locomotion means itself does not change device geometry significantly (e.g., the device could use surface-based motivators such as treadmills or small surface oscillations, rather than moving extended structures such as flagella; in this case, selection of device hardware could be made with the design objective of simplifying control software to reduce computational requirements, rather than focusing solely on the power efficiency or other performance criteria of the locomotion motivator(s)).

With both the above methods, the device can obtain stress values that correspond to those for passive motion, and so can apply the evaluation techniques for passive motion discussed herein. This approach requires no additional training with locomoting devices.

Computational Requirements

An important metric for the analysis techniques discussed herein is their computational cost. Of course, each device, whether a single device, or part of a group, or external computation means, will have programming, which might also be referred to as instructions or instruction sets, that are used as part of the processes for data storage, data feature extraction and selection, matching data features with system features, and determining device actions, based at least in part on the results of these processes. These processes are described herein in detail, and/or represented at a higher level in the flow charts of FIGS. 34-39. However, as will be appreciated by those skilled in the arts, there are many ways to implement such programming, including not only a virtually infinite number of ways even in the same language, but completely different languages, libraries, or software packages that may be used. For this reason, there is no way to state absolute computational cost. However, we can describe why the computational costs described herein are, generally speaking, quite low.

The most basic methods discussed herein use simple functions of a few Fourier coefficients of stress measurements. For n sensors, a direct evaluation of M Fourier coefficients uses of order Mn arithmetic operations (faster methods are available for computing many modes, but are not necessary if M is fairly small, as in the examples discussed). Normalizing the Fourier coefficients involves summing the magnitudes of the M coefficients and then dividing these magnitudes by this sum. Principal components are linear combinations of the normalized modes. Thus, the arguments used in the examples of regressions discussed herein involve of order Mn multiplications and additions. These evaluations involve a few thousand arithmetic operations for $n \approx 30$ sensors and $M \approx 6$ modes. Based on this, evaluating stress patterns every, say, 10 ms, would require less than $10^6$ operations/s. Expanding the analysis from a 2-dimensional treatment of the stresses to a 3-dimensional analysis would square the number of modes, resulting in 5-10 times the number of calculations for a similar 6-mode analysis. The calculation requirements could be reduced by computing parameters externally and employing look-up tables for comparison to current stress patterns. Another approach may be to reduce the number of modes examined; in the techniques discussed, it was found that most of the information was contained in the first two modes. Also, various dimension reduction techniques such as are well-known in the art could be employed.

The more sophisticated techniques discussed herein, such as using a classifier to detect branches in a vessel, require computational cost both to train the classifiers and to use them. The training can be performed off-line, from sensor measurements collected along a sample of paths, and thus could take place on, e.g., a conventional computer, cluster of computers, or computers with hardware optimized for the problem at hand (e.g., offloading some computations onto GPUs) rather than in a device in a fluid system, with only the resulting regression parameters stored in the device's memory. Thus, the computation cost of training is not significantly constrained by the devices' on-board computational capabilities. Devices applying the classifier would use their on-board computer to repeatedly evaluate the trained classifier from their sensor measurements. Thus, there is a computational requirement for devices using the classifier, and a memory requirement for the device to store the parameters obtained from the training, but these requirements are quite small compared to the generation of training data and the training process itself.

The example of a branch detection classifier discussed herein involves a small set of parameters (see Table 7) and recording several sets of stress measurements (represented by their low-frequency Fourier coefficients) to allow evaluating correlations. This information amounts to about 100 numbers, which could fit in a kilobyte of memory. The regression parameters are just a few additional numbers, so do not add significantly to the memory requirement.

The classifier example uses simple functions of stress measurements. Specifically, Eq. (19) involves correlations, calculated values of a device's relative position, and the principal component of Fourier modes of the stresses. All these quantities can be computed from a few low-frequency Fourier coefficients of stress measurements on the device's surface. Again, a computer capable of $10^6$ operations/s could evaluate these values every few milliseconds. As discussed above, a 3-dimensional analysis is likely to require 5 to 10 times the operations of a 2-dimensional analysis. This is a very small, very efficient set of computations, which could be made even smaller by reducing the Fourier modes used, evaluating input less frequently, or using other techniques well known to those skilled in the art.

Applications of Techniques

The present disclosure shows examples of how devices in viscous flow can use solely instantaneous measurements of surface stresses to determine their position, orientation, and relation to the vessel through which they travel; this information can include, e.g., their direction and distance to the nearest vessel wall, how fast the device is moving, and the vessel diameter. Classification of vessel geometric features (including discontinuities, such as abrupt changes in vessel shape, or the presence of other objects in the fluid flow) can also be made accurately.

This information can then be used to build maps, navigate devices through fluid systems, appropriately task robots (e.g., to remove plaques, plug leaks, adjust sensor, locomotion, or other duty cycles, and set up even more accurate and powerful systems where multiple devices can cooperate to share data or perform specialized tasks (e.g., serving as branch point beacons)). These actions can all be controlled by collecting very small amounts of data and performing calculations that are within the reach of virtually any processor in real-time (once training has been completed, if appropriate).

Similar techniques should be effective for other fluid parameters that can be readily detected by devices equipped with appropriate sensors, such as fluid viscosity, flow speed, etc., and fluidic data could be combined with non-fluidic data (e.g., external location signals) to increase accuracy and versatility.

Note that while the examples given, where a specific physical implementation is referenced, tend to discuss micron-scale devices in micron-scale channels, this is by no means the only size scale to which these techniques apply. The determining factor is not size, but rather the Reynolds and Womersley numbers, which take into account multiple factors, including viscosity. All other things being equal, if a device is made X times larger, and the viscosity of the fluid is also increased X times, the resulting system will behave the same and can be analyzed in the same manner (i.e., systems having the same Reynolds and Womersley numbers have dynamic similarity). Water, and blood (or plasma), are not particularly viscous. Water has a viscosity of 1 cp. Plasma has a viscosity of about 1.3 cp to 1.7 cp. However, there are commercially-important liquids with vastly higher viscosities. For example, motor oil can have a viscosity of >1,000 cp, honey has a viscosity of about 5,000+cp, ketchup has a viscosity of about 5,000+cp, sour cream has a viscosity of about 100,000 cp, and peanut butter has a viscosity of about 10,000 cp to 1,000,000 cp. Because these liquids have viscosities ranging from about 1,000 times higher than blood plasma or water, to over 100,000 times higher than blood plasma or water, devices operating in these fluids can be that many times larger and still be operating in the viscous flow regime. To give some exemplary size and viscosity comparisons, a 1 um device operating in water is equivalent to a 10 cm (3.9 inches) device operating in sour cream, or a 25 cm (9.8 inches) device operating in thick peanut butter. So, in an industrial setting where devices could be used for tasks such as pipe mapping and cleaning, leak or obstruction detection, in viscous liquids the techniques taught herein will work exactly as they would for a device on the micron-scale in water, blood, or plasma.

Table 11 provides representative values for some representative substances and related dimensions covering a broad range of various viscosities.

TABLE 11

| Material | Viscosity (cp) | Velocity (m/s) | Density (kg/m^3) | Characteristic Distance (m) | Reynolds Number |
|---|---|---|---|---|---|
| Peanut butter | 10,000 to 1,000,000 | 1.0 | 1.08 | 0.1 | 0.01 to 0.0001 |
| Peanut butter | 10,000 to 1,000,000 | 1.0 | 1.08 | 1.0 | 0.1 to 0.001 |
| Ketchup | 5,000 to 20,000 | 1.0 | 1.43 | 0.01 | 0.003 to 0.0007 |
| Honey | 5000 | 0.1 | 1.45 | 0.2 | 0.04 |
| Blood Plasma | 1.3 to 1.7 | 0.1 | 1.03 | 0.001 | 0.08 to 0.06 |
| Olive Oil | 56 | 0.1 | 0.93 | 0.1 | 0.17 |
| Water | 1 | 0.1 | 1.00 | 0.01 | 1 |

Note that diffusion rates are directly related to viscosity via the Stokes-Einstein equation, and so it will be obvious that similar comments and analysis apply to, e.g., diffusion of chemicals.

Figure 34:
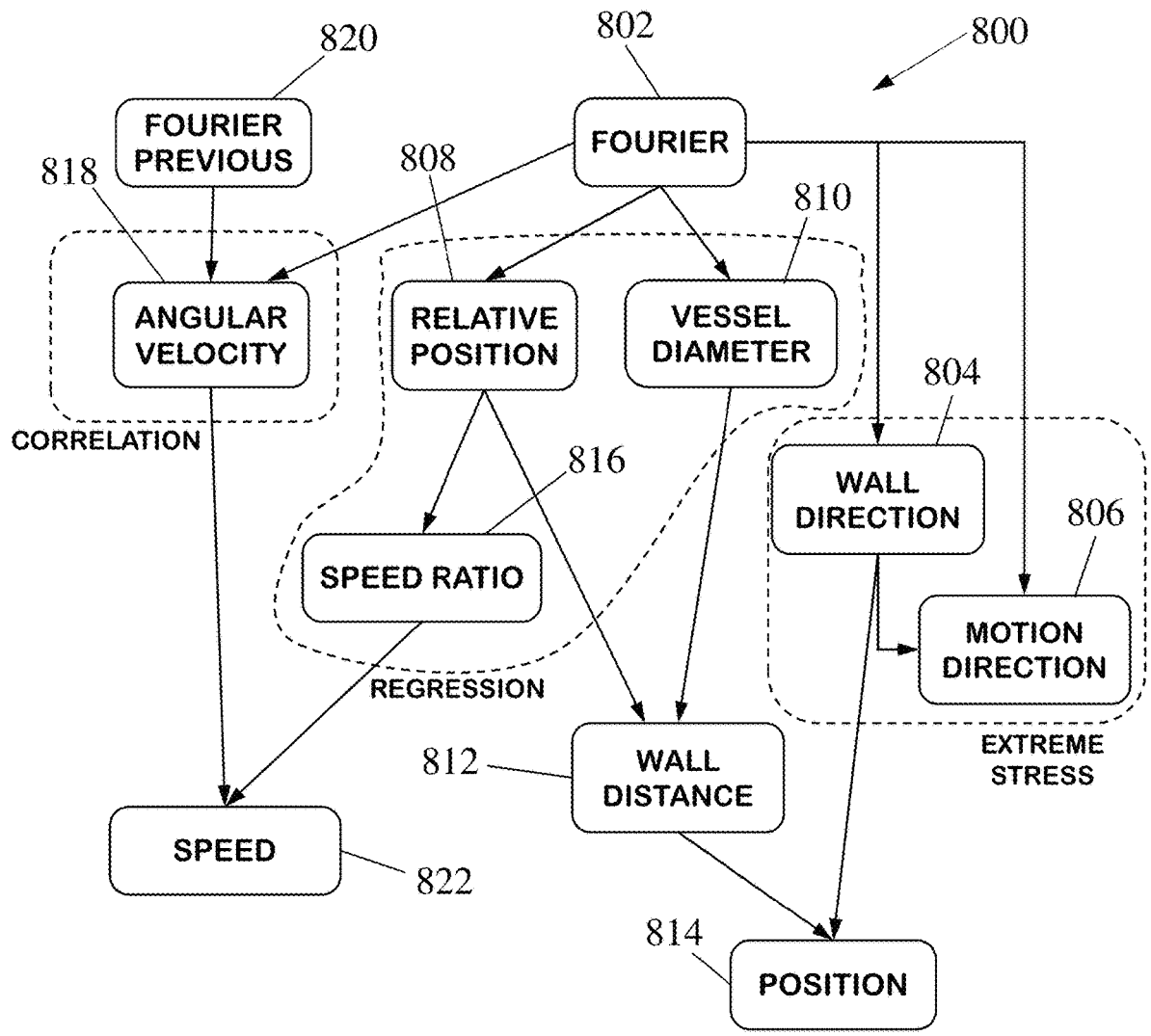
FIG. 34 is a schematic illustration that shows an overview of techniques that can be employed to derive values of several parameters of device position and motion, as well as vessel geometry, according to the examples discussed with respect to FIGS. 1-15.

FIG. 34 schematically illustrates one example of a method 800 for determining calculated parameters using stress measurements and various analysis techniques, such as discussed in the examples of 2-dimensional analysis presented above. From a Fourier transform 802 of the stresses across the surface of the device, the location of extreme stress can be employed to evaluate the direction to the wall 804, and this direction in combination with the Fourier components 802 can be employed to evaluate the direction of motion 806.

From regression analysis of the Fourier components, values can be calculated for the relative position 808 of the device in the vessel and the vessel diameter 810; these two calculated values can, in turn, be used to calculate the distance to the nearest wall 812. The distance 812 and direction 804 to the nearest wall provide a position 814 for the device relative to the cross-section of the vessel.

The relative position 808 can also be related to a ratio 816 of speed to angular velocity 818. Angular velocity 818 in the examples presented is evaluated by correlating the current Fourier values 802 with previous values 820 determined before a time interval. Once an angular velocity value 818 has been calculated, it can be used with the speed ratio 816 to calculate a speed 822 of the device along the vessel.

Figure 35:
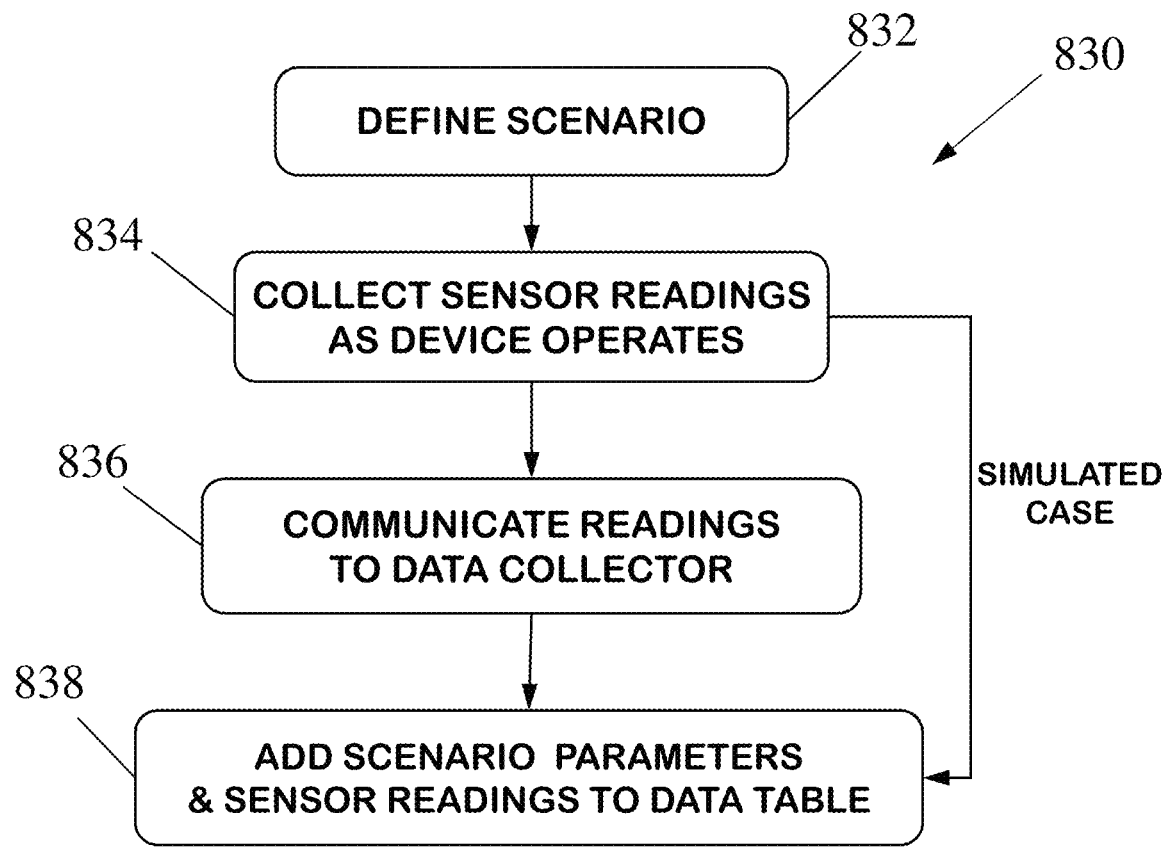
FIGS. 35-37 are flow charts that broadly illustrate examples of methods for collecting data (FIG. 35), training inference models (FIG. 36), and employing such inference models in a device (FIG. 37).
Figure 36:
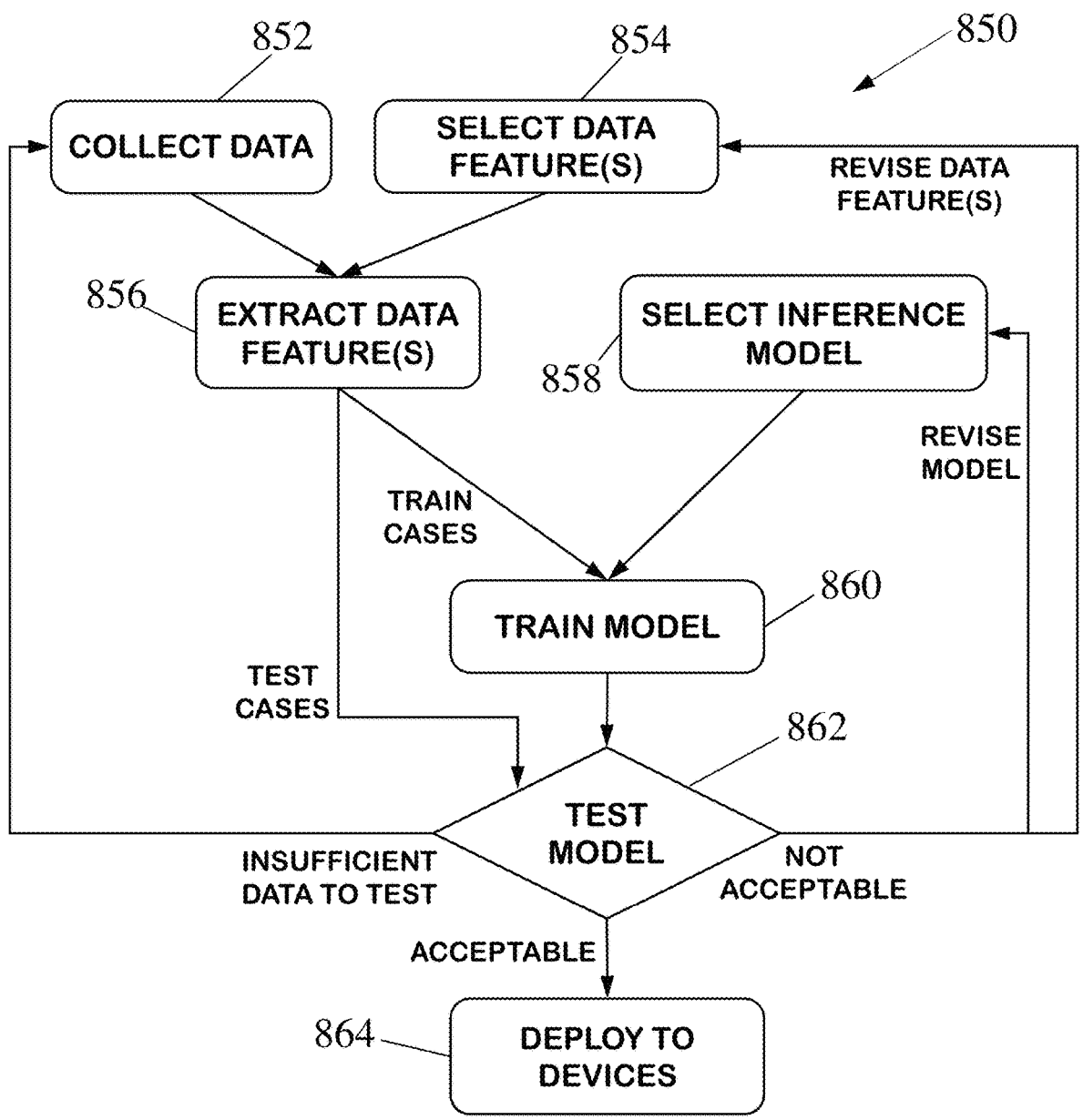
Figure 37:
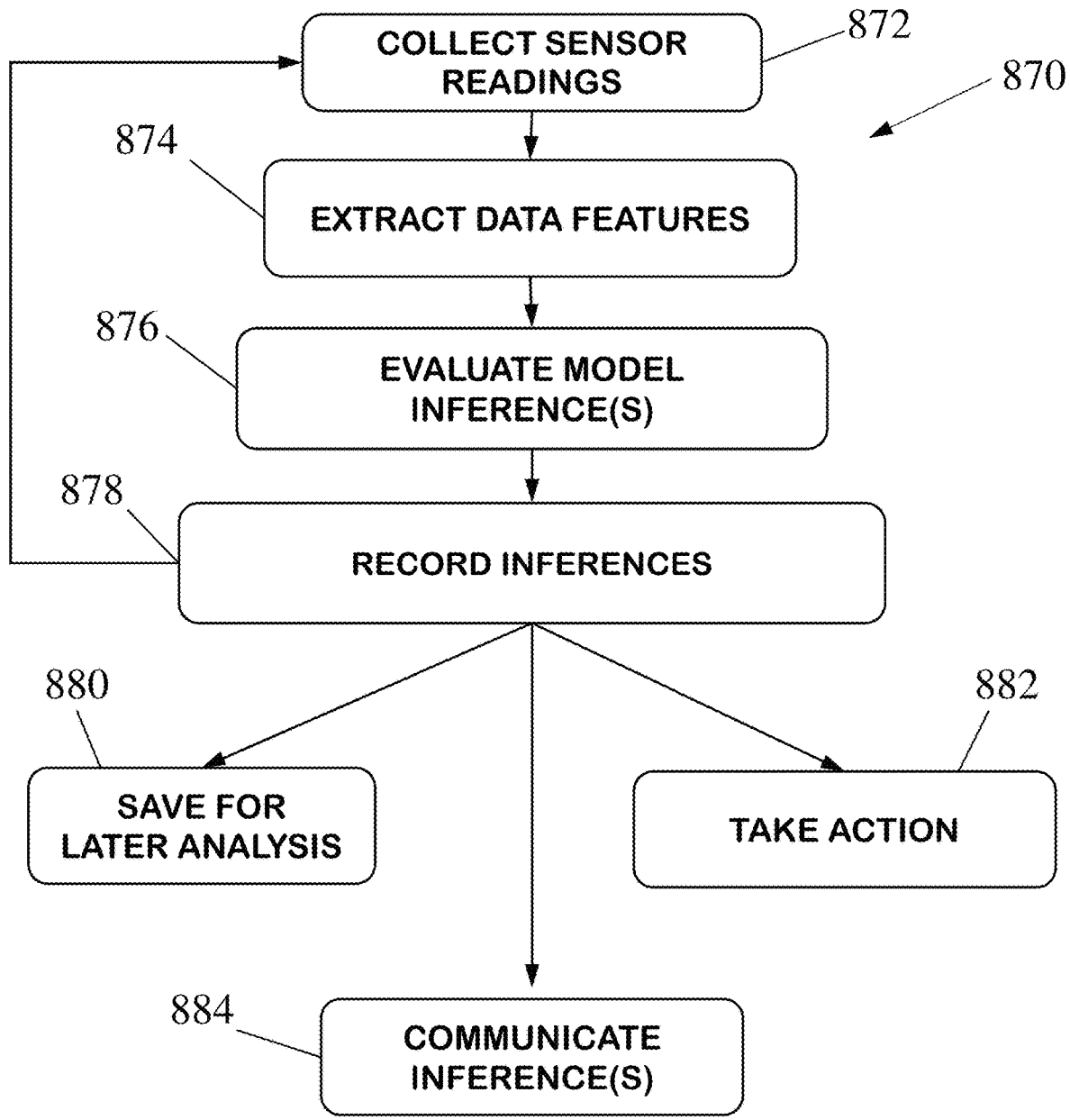

FIGS. 35-37 broadly illustrate examples of methods for collecting data (FIG. 35), training an inference model (FIG. 36), and employing such inference models in a device (FIG. 37). Note that all flow charts herein are merely representative of one possible process for accomplishing a given goal. Given the teachings herein, it will be obvious when some steps might be omitted, repeated, performed in a different order or with different triggering conditions, or where a new step might be added, and the exact work-flow is likely to be goal- and device-dependent.

FIG. 35 shows one example of a method 830 for collecting data, either by use of actual devices or by simulations. First, a scenario 832 is defined for which data are desired; the scenario 832 could be physically modeled, for data collection by devices introduced into the model, or could be constructed as a virtual model for a simulated scenario (one example being the situations and parameters of vessel and device sizes, positions, geometry, flow speed, etc.) As the device operates (either actual devices operating in a physical model or simulated devices operating in a virtual model; the device can be moving or can remain in place while the flow passes it), sensor readings 834 are collected (in the examples discussed herein, simulated sensor readings are calculated based on the parameters of virtual models and simulated device movement) responsive to the movement; in the simulated examples discussed herein, both tangential and normal surface stresses across the device surface were recorded. In the case of physical devices, the collected sensor readings 834 are communicated 836 to a data collector, where the sensor readings 834 are added 838 (along with the relevant parameters of the scenario being sensed) to a data table for analysis. Where extremely small devices with limited memory and computational capability are employed, the data collector is typically located in a remote computer. In the case of a simulated scenario, the virtual model and simulated devices are typically implemented on the same data processing apparatus as the data collector, and thus the sensor readings 834 may be automatically sent to the data collector and added to the data table 838 as they are recorded.

FIG. 36 illustrates one example of a method 850 for training inference models. Data are collected 852, using methods which could include the generic data collection method 830 illustrated in FIG. 35. One or more data features of interest are selected 854; one example of such data features are principal modes of Fourier components, but clearly other features of the data could be employed. The selected data feature(s) 854 are then extracted 856 from the collected sensor data 852; such "extraction" is normally a definite mathematical operation on the data to obtain the selected data feature(s) 854 (e.g., in the examples discussed herein, the Fourier coefficients for the stress pattern data are calculated and then the principal components are evaluated). However, in some cases the data may be used as is, or with simple pre-processing, conditioning, etc. The extracted feature(s) 856 and a selected inference model 858 are employed to train a model 860 for how the extracted feature(s) 856 relate to the inference model 858 (such as the example discussed herein where the first two Fourier mode components are related to vessel diameter or related the relative position of the device). The trained model 860 can then be tested 862 with additional extracted features 856 to evaluate the accuracy of how well the evaluations provided by the trained model 860 match the actual characteristic of the fluid system. In the event that there is insufficient data for extracted features 856 to effectively test 862 the trained model 860, then data collection 852 is continued. If there are a sufficient number of extracted features 856, but the accuracy of the trained model 860 is not acceptable for the particular desired application, then the inference model 858 and/or the selected feature(s) 854 are revised to find an inference model 858 and associated features 856 that provide a sufficient degree of accuracy for the intended purpose. In the case of revising the inference model 858, such revision could include keeping the same basic technique (such as a regression) but considering additional terms, employing a different machine learning technique, or using a mix of techniques (which is well-known in the field of machine learning and data mining and which can involve, e.g., weighting and voting schemes to combine the outputs of multiple techniques). In the case of revising the extracted feature(s) 856, additional terms could be considered (such as considering more than the first two principal components, in the examples discussed herein) or alternative dimension reduction techniques could be employed on the sensor data. It should be noted that the selection of an inference model 858 could be at least partially automated, such as by using software that checks and compares different models for effectiveness in classifying a particular set of data (e.g., the automated selection of machine learning method available in Mathematica, Weka (https://www.cs.waikato.ac.nz/ml/weka/) or any of numerous other such software packages). After revision, the model 860 is retrained using the extracted features 856 (using either the same features 856 as previously employed with a revised inference model 858, or revised features 856 used with either the previous or a revised inference model 858). This revision process can be continued iteratively until the trained model 860 shows the desired degree of accuracy for the intended application. When the test 862 shows the trained model 860 to be sufficiently accurate for the desired application, the trained model 860 can be provided 864 to devices for use, either for further data collection, analysis, and refinement of analysis techniques, or for actual operation to accomplish a desired mission (such as by the method 870 shown in FIG. 37).

FIG. 37 is a flow chart showing one example of a method 870 for using a trained inference model such as the trained model 860 discussed above. First, the device collects sensor data 872, and then data features 874 are extracted from the data (either by the device or by a remote computer), according to the selection of extracted features 856 for the particular inference model 858 employed in the trained model 860 being used. The trained model 860 is then employed to provide an evaluation 876 of a characteristic of the device position, movement, and/or vessel geometry based on the extracted features 874. The inference 876 may then be recorded 878, at least in local memory, for reference by the device in determining further operation (if the inference is that the characteristic is not important to current operations, it may be ignored rather than recorded). Note that recording could be transient, e.g., in RAM or the equivalent, or can be saved for later analysis 880, in a more permanent memory (e.g., in traditional non-volatile storage); it should be noted that this step is optional, and a device could go directly from evaluating an inference to, e.g., taking action. Subsequently, data collection 872 continues. Depending on the mission of the device and the particular inference 876, one or more of various actions can be taken, with three typical actions being shown in FIG. 37. As noted, the current inference 876 can be saved 880 for later analysis (i.e., stored in the memory of the device and/or a remote computer), possibly in combination with the sensor data 872 and/or the extracted features 874; these data can then be used for later refinement of the inference model, and/or possibly in coordination with other inferences to provide a record of inferred data that can be used for mapping the fluid system and similar purposes. The device can take action 882, such as moving to enter a branch or move closer to a wall, and/or may activate or deactivate capabilities appropriate to the particular inferred condition 876 relative to the mission of the device. The device can also communicate 884 the inference 876, such as to nearby devices or to an external location accessible to the operator. One example of communicating 884 to one or more other devices occurs in the situation where multiple devices with differing capabilities are employed together in a group to optimize the function of each; in a typical case, devices optimized for sensing transmit their analysis results to devices optimized to take a desired action at the particular feature location (e.g., releasing a medication at the location of a tumor, applying a sealant at the location of a leak, etc.)

Operation Example—Fluid System Mapping

Figure 38:
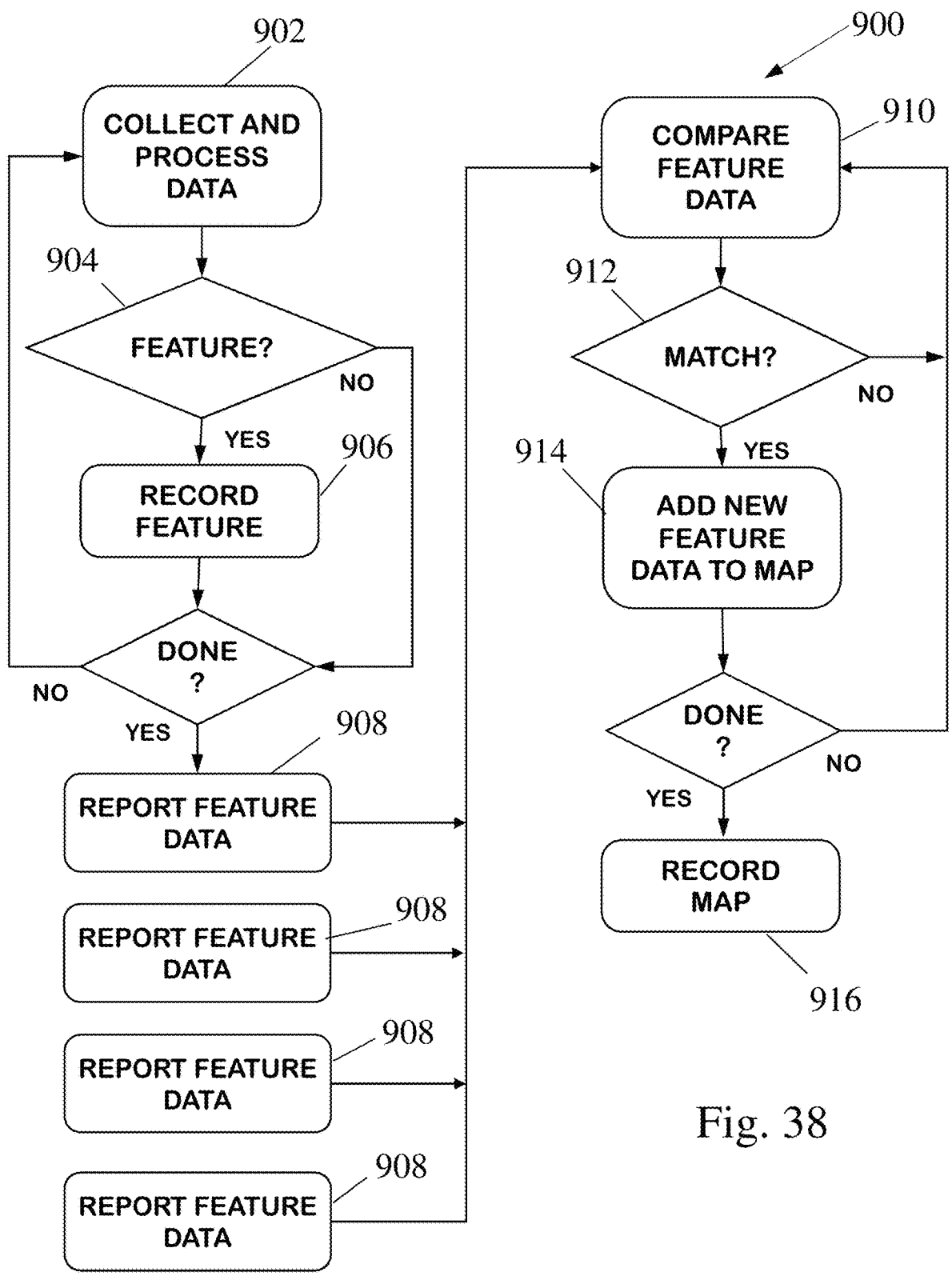
FIGS. 38 & 39 are flow charts illustrating examples of a mapping procedure (FIG. 38) for comparing feature data from multiple devices and constructing a map of a fluid system, and a procedure (FIG. 39) for a device to use such a map to aid in performing a prescribed mission.
Figure 39:
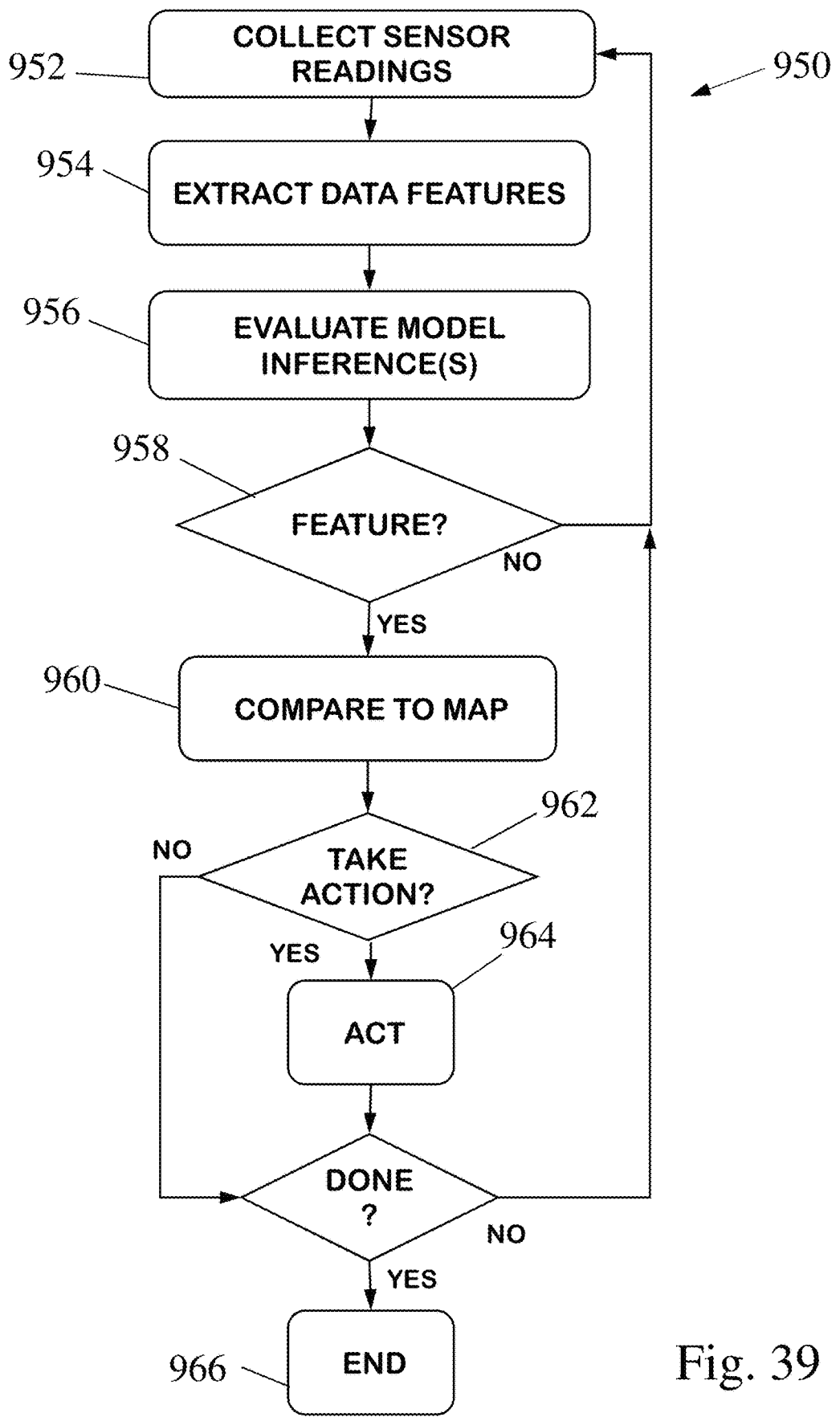

FIGS. 38 and 39 illustrate two examples of operations that could be done using the passive sensing and analysis techniques such as discussed herein (as well as in combination with many other techniques discussed herein, and well-known in the art). FIG. 38 shows an example of constructing a map of a fluid system, while FIG. 39 illustrates an example of a device employing such a map.

FIG. 38 shows a method 900 for constructing a map, which relies on one or more devices operating to collect and process data using passive sensors. The processing of the data can be done, e.g., using a trained inference model; this operating step 902 can be essentially similar to the steps 872, 874, and 876 in the method 870 illustrated in FIG. 37, with the addition of recording position information. In the simplest case, position information can be a distance derived from elapsed time (measured by a timer) and a fluid speed value obtained from angular velocity and speed ratio, as discussed in the description of FIG. 34.

When a feature of interest, such as a branch or merge is detected 904, the position and any available characteristics of such feature are recorded 906, and the steps 902, 904, & 906 are repeated until it is determined that the data collection procedure is completed, at which point the recorded positions and characteristics of features are reported 908 to one or more central databases ("database" being used in the general sense of any type of data storage), if offloading such functions to an external computer, or stored in device memory. In addition to the locations of branches and merges, additional data on the fluid system at a given location may be collected and evaluated such as changes in vessel diameter, curvature, asymmetry, etc. This additional data can help to distinguish the branches, such as branches having differing diameters, different degree of curvature, etc. When the device has additional sensing capabilities, additional data can be employed for further refine the position and/or to characterize the branches. As examples, gravity and/or magnetic field detection could provide a global index of direction, an on-board gyroscope could provide a consistent local index of direction, reception of electromagnetic or acoustic signals (either already present in the fluid system or deliberately induced) could provide references for direction, detection of chemical gradients could provide relative directions with respect to a source or sink for such chemicals, etc. In some cases, the "position" of a feature may be expressed solely in terms of some parameter of interest being sensed, rather than absolute location; for example, if the device senses chemical gradients, the "position" of a feature might be expressed solely in terms of chemical concentrations, rather than absolute location. While discussed in terms of branches and merges, it should be appreciated that other features could be mapped, such as curvature, irregularities in the channel, partial obstructions, points of apparent leakage, etc.

When the procedure is considered to be complete can be determined by various factors, such as when sufficient data has been collected to reach a desired level of accuracy, when the use of additional device memory is not desirable, when the device has limited power and running the sensors is not a priority, when the device exits the portion of the fluid system of interest, or when the device has become immobile. The data-collection procedure can be done multiple times and can be done by a number of different devices, each reporting 908 its record of feature positions and other data to a central database that can be used both to offload computation, and to allow one device to access data acquired by another device. Because the devices can employ relatively simple sensors (such as stress and shear sensors) and require only modest computational capacity, they can be fabricated more inexpensively than more complex devices, and a mapping operation may employ a single device, but may also employ dozens, hundreds, thousands, or even millions or more of devices.

Once the records of feature positions and any relevant characteristics from one or more devices have been reported 908, they are compared 910 to identify areas where the features match (including a match with overlap, which can be used to help combine contiguous segments of the map, similar to the way shotgun sequencing for DNA is performed). Where a match is detected 912, new positions and available characteristics of one or more features are added 914 to a map stored in memory. It should be noted that "new" features could include duplicate reports of features previously added, with the additional report adding to the confidence of the position and characteristics, and/or refining the position and characteristics for greater accuracy.

The steps of comparison 910, identifying matching overlaps 912, and adding features 914 are repeated until the map-construction procedure is considered complete; such completion could be determined by various criteria, such as whether the map is considered sufficiently complete and accurate, or whether, in a multi-device scenario, a threshold number of devices have reported 908 their records. When map construction is considered to be done, the completed map is recorded 916 for future use (although the incomplete map can, and probably would, be recorded incrementally and used to aid the mapping process itself, such as by providing data that can direct a device to an area that is not believed to be accurate enough, or where coverage is completely lacking, or to let a device know how to exit the system for repair, recharge, wired data downloads and uploads, etc.)

FIG. 39 illustrates one example of a device employing a map, such as the map recorded in step 916 shown in FIG. 38. The device performs a navigation procedure 950, which includes the steps of collecting sensor readings 952, extracting data features 954 from the sensor measurements, and applying a trained model to the extracted data features to evaluate 956 one or more parameters of the device position and/or movement, the fluid flow, and/or the fluid system geometry. These steps can be essentially similar, respectively, to the steps 872, 874, and 876 of the method 870 shown in FIG. 37, with an additional record of position (such as distance traveled) typically being maintained, as discussed for step 902 of the method 900. When the evaluation 956 indicates the presence of a feature 958 of interest in the fluid system, the position and any characteristics which can be evaluated (diameter, curvature of the branches, etc.) is compared 960 to the map to identify the particular feature.

Based on the map and the particular mission of the device, a decision 962 is made whether or not the device should take action 964 at this particular feature location. The action 964 to be taken depends on the particular mission of the device and how the detected feature location relates to such mission. For a device with locomotion, the action could be to move into one branch versus the other, depending on the desired mission of the device. For example, the device might choose a branch in order to reach a particular destination, might purposefully leave known areas of a map to gather additional data to extend the map, might repeat a known route to refine the map, might choose to avoid known areas of high risk (e.g., in a biological context, the sinusoid slits of the spleen, might be a likely location for devices to get stuck, and in any system, sharp turns, reduced channel diameters, changes in heat or pressure, or other factors, might all put a device at risk of becoming stuck or damaged), or might simply take a different route than other devices have taken, to provide more complete coverage of the overall fluid system.

Another option for a device with locomotion would be to move to the nearest vessel wall and anchor to it so as to be stationed at that location, such as to provide a location beacon, to detect passing objects, etc. In another example of a possible action, the particular mapped location may be one where there is evidence of tumor growth, and the device could be designed to release a tumor-killing chemical at such location. In an industrial setting, the device might affix itself to an area believed to be leaking, either sealing the leak with its own body, releasing some type of sealing material, or being used as a homing beacon for other devices inside, or outside, the system. Similarly, the device could, e.g., affix itself to an area with some type of waste or plaque buildup, and scrape or dissolve it off (potentially taking it into its own body so as not to contaminate the fluid). It should be noted that the sensing/analysis and action functions could be incorporated into separate physical devices, such as a multi-device group where one or more devices perform the sensing functions and transmit the analysis results to one or more other devices that take action based on the results.

Where additional sensor data beyond that used for feature identification/location is available, such additional data could inform the decision of whether or not to take action, and/or the determination of which of multiple action choices should be taken. It should be appreciated that the variety of possible actions is commensurate with the variety of possible missions to be undertaken by such devices.

Some of scenarios present options even for devices that lack locomotion. For example, if a device flows through a system randomly, if it is in a portion of the system that has already been mapped, it may elect to shut sensors down for some period of time to conserve power. If it randomly flows past a system feature of interest, it may elect to broadcast that information as a priority to other devices or to a central database. It may also emit or absorb chemicals (e.g., as in the tumor killing example—locomotion would be useful, but not necessary), or affix itself to the wall. Clearly, depending on many factors, such as the device's mission, what capabilities the device has, and whether it is operating alone or in a group, with or without locomotion, there can be many actions to be taken.

Whether or not an action 964 is taken at the location, the sensing 952, extraction 954, evaluation 956, feature detection 958, comparison 960 to mapped features, determination 962, and action taken 964 (when appropriate) are repeated until the procedure is considered complete and is ended 966. Such end could be based on the device becoming inactive, the action 964 being considered to complete the mission, the device leaving the fluid system or having traveled a prescribed distance, or other criteria depending on the situation.

While the novel features of the present techniques are described in terms of particular examples and preferred applications, it should be appreciated by one skilled in the art that, given the teachings herein, which demonstrate the surprisingly accurate inferences that can be made from simple sensor data, and which analyzed in a manner that computationally allows acting on the inferences in essentially real-time, which greatly improves device function and versatility, the techniques discussed are applicable to a variety of other situations in viscous flow, and that alternative analysis schemes could be employed without departing from the spirit of the invention, and which would be apparent from the teachings herein.

REFERENCES

The following publications provide background information on many of the technical topics discussed above.

Akers, W. (2004), "A Molecular Rotor as Viscosity Sensor in Aqueous Colloid Solutions", Journal of Biomechanical Engineering.

Aster, R., Borchers, B., et al., (2012), "Parameter Estimation and Inverse Problems, 2nd Edition," Academic Press.

Augustin, H. and Koh, G. (2017), "Organotypic vasculature: From descriptive heterogeneity to functional pathophysiology", Science.

Berg, H., (1993), "Random Walks in Biology," Princeton University Press.

Bishop, C., (2011), "Pattern Recognition and Machine Learning (Information Science and Statistics)," Springer.

Bleckmann, H. and Zelick, R. (2009), "Lateral line system of fish", Integrative Zoology.

CASSOT, F., LAUWERS, F., et al. (2006), "A Novel Three-Dimensional Computer-Assisted Method for a Quantitative Study of Microvascular Networks of the Human Cerebral Cortex", Microcirculation.

Chambers, L. D., Akanyeti, O., et al. (2014), "A fish perspective: detecting flow features while moving using an artificial lateral line in steady and unsteady flow", J R Soc Interface.

Dobson, A. and Barnett, A., (2008), "An Introduction to Generalized Linear Models," CRC Press.

Dusenbery, D. B., (2009), "Living at Micro Scale: The Unexpected Physics of Being Small," Cambridge, Mass., Harvard University Press.

Eswaran, P. and Malarvizhi, S. (2013), "MEMS Capacitive Pressure Sensors: A Review on Recent Development and Prospective", International Journal of Engineering and Technology.

Everitt, B. and Hothorn, T., (2010), "A Handbook of Statistical Analysis Using R, 2nd Edition," CRC Press.

Freitas, R., (1999), "Nanomedicine, Volume I: Basic Capabilities," Landes Bioscience.

Géron, A., (2017), "Hands-On Machine Learning with Scikit-Learn and TensorFlow: Concepts, Tools, and Techniques to Build Intelligent Systems," O'Reilly Media.

Golub, G. and Loan, C. V., (1983), "Matrix Computations," Baltimore, Md., John Hopkins University Press.

Goodfellow, I., Bengio, Y., et al., (2016), "Deep Learning (Adaptive Computation and Machine Learning series)," MIT Press.

Grosse, S. and Schroder, W. (2009), "The Micro-Pillar Shear-Stress Sensor MPS(3) for Turbulent Flow", Sensors.

Gunter Pawlik, A. R., and Richard J. Bing (1981), "Quantitative capillary topography and blood flow in the cerebral cortex of cats: an in vivo microscopic study", Brain Research.

Haidekker, M., (2009), U.S. Pat. No. 7,517,695, "Local flow and shear stress sensor based on molecular rotors".

Haidekker, M., Grant, S., et al., (2010), U.S. Pat. No. 7,670,844, "Supported molecular biolfluid viscosity sensors for invitro and in vivo use".

Haidekker, M., Grant, S., et al., (2011), U.S. Pat. No. 7,943,390, "Supported molecular biofluid viscosity sensors for in vitro and in vivo use".

Haidekker, M. A., Akers, W., et al. (2005), "Sensing of Flow and Shear Stress Using Fluorescent Molecular Rotors", Sensor Letters.

Happel, J. and Brenner, H., (1983), "Low Reynolds Number Hydrodynamics," The Hague, Kluwer.

Hastie, T., Tibshirani, R., et al., (2009), "The Elements of Statistical Learning: Data Mining, Inference, and Prediction," Springer.

Herrera-May, A. L., Aguilera-Cortes, L. A., et al. (2009), "Resonant Magnetic Field Sensors Based On MEMS Technology", Sensors (Basel).

Hogg T. (2007), "Coordinating microscopic robots in viscous fluids", Autonomous Agents and Multi-Agent Systems.

Hogg T. (2014), "Using surface-motions for locomotion of microscopic robots in viscous fluids", J. of Micro-Bio Robotics.

Hogg, T. (2018), "Identifying Vessel Branching from Fluid Stresses on Microscopic Robots".

Hogg, T. (2018), "Stress-based navigation for microscopic robots in viscous fluids", Journal of Micro-Bio-Robotics.

Hogg T. and Freitas, R. (2012), "Acoustic communication for medical nanorobots", Nano Communication Networks.

Huikai, X. and Fedder, G. K. (2003), "Fabrication, characterization, and analysis of a DRIE CMOS-MEMS gyroscope", IEEE Sensors Journal.

Jain, R. K., Martin, J. D., et al. (2014), "The role of mechanical forces in tumor growth and therapy", Annual Review of Biomedical Engineering.

Jordan, M. I. and Mitchell, T. M. (2015), "Machine learning: Trends, perspectives, and prospects", Science.

Kantsler, V., Dunkel, J., et al. (2014), "Rheotaxis facilitates upstream navigation of mammalian sperm cells", eLife.

Karimi, A., Yazdi, S., et al. (2013), "Hydrodynamic mechanisms of cell and particle trapping in microfluidics", Biomicrofluidics.

Kim, S. and Karrila, S., (2005), "Microhydrodynamics," Dover Publications.

Koka, A. and Sodano, H. A. (2013), "High-sensitivity accelerometer composed of ultra-long vertically aligned barium titanate nanowire arrays", Nat Commun.

Li, J., Esteban-Fernandez, B., et al. (2017), "Micro/nanorobots for biomedicine: Delivery, surgery, sensing, and detoxification", Science Robotics.

Liu, G., Wang, A., et al. (2016), "A Review of Artificial Lateral Line in Sensor Fabrication and Bionic Applications for Robot Fish", Appl Bionics Biomech.

Lofdahl, L. and Gad-el-Hak, M. (1999), "MEMS-based pressure and shear stress sensors for turbulent flows", Meas. Sci. Technol.

LUTZ, R., CANNON, J., et al. (1977), "Wall Shear Stress Distribution in a Model Canine Artery during Steady Flow", Circulation Research.

Martel, J. M. and Toner, M. (2014), "Inertial focusing in microfluidics", Annu Rev Biomed Eng.

Martin, H. P., Brooks, N. J., et al. (2010), "Complex fluids under microflow probed by SAXS: rapid microfabrication and analysis", Journal of Physics: Conference Series.

Merkle, R., Freitas, R., et al., (2016), "Molecular Mechanical Computing Systems," Institute for Molecular Manufacturing.

Merkle, R., Freitas, R., et al. (2018), "Mechanical computing systems using only links and rotary joints", ASME Journal on Mechanisms and Robotics.

Merkle, R., Freitas, R., et al., (2015), US Patent Application 20170192748, "Mechanical Computing Systems".

Middlemiss, R. P., Bramsiepe, S. G., et al. (2017), "Field Tests of a Portable MEMS Gravimeter", Sensors (Basel).

Mostafa, Y., Ismail, M., et al., (2012), "Learning From Data," AMLBook.

Murray, C. (1926), "The physiological principle of minimum work: I. The vascular system and the cost of blood volume", Proceedings of the National Academy of Sciences USA.

Mustafic, A., Huang, H. M., et al. (2010), "Imaging of flow patterns with fluorescent molecular rotors", J Fluoresc.

Nagy, A., Chang, S., et al. (2009), "Why are tumour blood vessels abnormal and why is it important to know?", British J. of Cancer.

Petersson, F., Aberg, L., et al. (2007), "Free Flow Acoustophoresis: Microfluidic-Based Mode of Particle and Cell Separation", Anal. Chem.

Pillapakkam, S., Barbier, C., et al., (2007), "Experimental and numerical investigation of a fish artifical lateral line canal."

Purcell, E. M. (1977), "Life at low Reynolds number", American J. of Physics.

Secomb, T., Hsu, R., et al. (2001), "Motion of red blood cells in a capillary with an endothelial surface layer: effect of flow velocity", American J. of Physiology: Heart and Circulatory Physiology.

Sharp, K., Adrian, R., et al., (2005), "Liquid Flows in Microchannels," CRC Press.

Sochi, T. (2015), "Fluid flow at branching junctions", International Jounral of Fluid Mechanics Research.

Soundararajan, G., Rouhanizadeh, M., et al. (2005), "MEMS shear stress sensors for microcirculation", Sensors and Actuators A: Physical.

Tang, Z., Feng, H., et al. (2019), "Design and simulation of artificial fish lateral line", International Journal of Advanced Robotic Systems.

Turduev, M., Cabrita, G., et al. (2014), "Experimental studies on chemical concentration map building by a multi-robot system using bio-inspired algorithms", Autonomous Agents and Multi-Agent Systems.

Varma, S., Hou, H. W., et al., (2013), "A Cell-based Sensor of Fluid Shear Stress for Microfluidics," Freiburg, Germany.

Vollmayr, A., (2014), "Snookie: An autonomous underwater vehicle with artificial lateralline system," Springer.

Wang, Y., Chen, C., et al. (2009), "MEMS-based gas flow sensors", Microfluidics and Nanofluidics.

Witten, I., Frank, E., et al., (2011), "Data Mining, Practical Machine Learning Tools and Techniques, 3rd Edition," Burlington, Mass., Elsevier.

Wu, J., Day, D., et al. (2010), "Shear stress mapping in microfluidic devices by optical tweezers", OPTICS EXPRESS.

Yang, Y., Chen, J., et al. (2006), "Distant touch hydrodynamic imaging with an artificial lateral line", Proceedings of the National Academy of Sciences USA.

Zhang, G., Sun, Y., et al. (2015), "Red-Emitting Mitochondrial Probe with Ultrahigh Signal-to-Noise Ratio Enables High-Fidelity Fluorescent Images in Two-Photon Microscopy", Anal Chem.

Zou, X., Liu, Y., et al. (2010), "Flow-induced beta-hairpin folding of the glycoprotein Ibalpha beta-switch", Biophys J.

The invention claimed is:

1. A system for operating a device within a fluid flow system under conditions where the fluid flow is characterized by a Reynolds number of less than 1, the system comprising:

an array of sensors distributed on the device which take measurements of fluid flow initial parameters that provide a representation of such initial parameters of the fluid flow at an instant of time;

a data processor and a memory accessible by said data processor;

at least one analysis instruction set for directing said data processor to operate on the measurements to determine a likely value for at least one value for a derived parameter selected from the group of:

parameters defining the position of the device relative to the fluid system, parameters defining the character of the motion of the device relative to the fluid system, parameters relating to the character of the fluid flow, and parameters defining the geometry of the fluid system.

2. The system of claim 1 wherein at least a subset of said sensors take passive measurements.

3. The system of claim 2 wherein at least a subset of said sensors measure stresses around said device.

4. The system of claim 1 wherein said at least one analysis instruction set includes instructions for comparing the most recent of the measurements representing at least a subset of the initial parameters at a most recent instant of time with at least one set of the measurements representing the same parameters at an earlier instant of time.

5. The system of claim 1 wherein said at least one analysis instruction set directs said data processor to determine a likely value for at least one derived parameter selected from the group of:

direction to nearest fluid system wall;
relative position of said device with respect to the cross-section of the fluid system;
angular velocity of said device;
linear velocity of the device; and
a dimension of the fluid system.

6. The system of claim 1 wherein said at least one instruction set includes directions for instructing said data processor to characterize at least one feature of fluid system geometry.

7. The system of claim 6 wherein at least a portion of said memory resides on said device and stores evaluation parameters used by said data processor when implementing said directions to characterize the at least one feature of fluid system geometry.

8. The system of claim 6 further comprising:

at least one comparison instruction set for directing said data processor to compare the characterized feature(s) to criteria identifying one or more prescribed features, yielding a degree of certainty that the characterized feature(s) match the one or more prescribed features of interest; and at least one control instruction set that directs said device to take a prescribed action based on the degree of certainty with which the characterized feature(s) match the feature(s) of interest.

9. The system of claim 8 wherein the prescribed action includes at least one action selected from the group of:

where said device has a locomotive capability and the characterized feature is a branch or a merger, activating said locomotive capability to move into a select one of multiple branches;
where said device has a locomotive capability, activating said locomotive capability to move to a wall of the fluid system;
releasing a stored chemical;
taking in a chemical present in the fluid environment;
transmitting a signal to remote receiver;
saving a record of the characterized feature location; and
changing operating parameters of said device.

10. The system of claim 9 wherein the prescribed action includes moving to a wall of the fluid system, and wherein the prescribed action further includes moving to whichever wall is nearest.

11. The system of claim 9 wherein the prescribed action includes transmitting a signal to a remote receiver, and wherein such action of transmitting further comprises at least one action selected from the group of:

transmitting location data for the characterized feature;
transmitting data that further characterizes the feature; and
transmitting identifying information for said device.

12. The system of claim 11 wherein said remote receiver is located on another device operating within the fluid system, which is provided with instructions to perform a prescribed action responsive to receiving the transmitted signal.

13. The system of claim 8 wherein said data processor, said memory, and said instruction sets reside at least partially on said device.

14. The system of claim 8 wherein at least a portion of said data processor and said instruction sets reside external to said device.

15. The system of claim 8 further comprising at least a partial map of the fluid system stored in said memory, and wherein said comparison instruction set includes instructions for comparing the characterized feature(s) to specific features located on said map.

16. The system of claim 8 wherein the prescribed feature is not defined with respect to its location in the fluid system.

17. The system of claim 16 wherein the prescribed feature is at least one feature selected from the group of:

a branch point;
a merger point;
a degree of curvature above a defined minimum;
an apparent discontinuity in any nearby wall of the fluid system; and
another object in the fluid flow.

18. The system of claim 1 wherein said device has a locomotive capability and said instruction set for directing said data processor to operate on the measurements to determine a likely value for at least one value of a derived parameter includes directions for compensating for the action of said locomotive capability.

19. A system for mapping a fluid system comprising:

at least one device equipped with passive sensors for taking measurements as said at least one device travels within the fluid system, the measurements providing representations of parameters of the fluid flow at instants of time when the measurements are taken;

a data processor that receives the measurements taken by said device(s) and which is programmed to operate on the measurements to characterize at least one geometry feature of the fluid system, at the time when a particular set of measurements are taken, with a prescribed degree of confidence;

a memory for storing the characterizations of geometry features and position information recorded for each characterized geometry feature; and an instruction set for directing said data processor to compare the geometry feature characterizations to identify matches and to place matching features characterized in different data records into relative position with respect to each other to form a map of the fluid system.

20. The system of claim 19 wherein said data processor and said memory are at least partially located on said at least one device.

21. The system of claim 20 wherein said data processor on said at least one device operates on the measurements using classification parameters stored in said memory on said at least one device.

22. The system of claim 19 wherein said at least one device equipped with passive sensors comprises an array of sensors distributed on the device which take measurements of fluid flow initial parameters that provide a representation of such initial parameters of the fluid flow at an instant of time; and further wherein said data processor is additionally programmed with,
at least one analysis instruction set for directing said data processor to operate on the measurements to determine a likely value for at least one value for a derived parameter selected from the group of:
parameters defining the position of the device relative to the fluid system,
parameters defining the character of the motion of the device relative to the fluid system,
parameters relating to the character of the fluid flow, and
parameters defining the geometry of the fluid system, said at least one instruction set including directions for instructing said data processor to characterize at least one feature of fluid system geometry, and
at least one comparison instruction set for directing said data processor to compare the characterized feature(s) to criteria identifying one or more prescribed features, yielding a degree of certainty that the characterized feature(s) match the one or more prescribed features of interest.

23. A method for operating a device within a fluid flow system under conditions where the fluid flow is characterized by a Reynolds number of less than 1, the method comprising the steps of:

measuring at least one initial parameter of the fluid using sensors distributed with respect to the device to provide a representation of the initial parameter(s) of the fluid flow around the device at an instant of time; and
analyzing the measurements using a quasi-static model of fluid forces to determine a likely value for at least one value for a derived parameter selected from the group of:
parameters defining the position of the device relative to the fluid system,
parameters defining the character of the motion of the device relative to the fluid system,
parameters relating to the character of the fluid flow, and
parameters defining the geometry of the fluid system.

24. The method of claim 23 wherein at least a subset of the sensors passively measure the initial parameter(s) of the fluid.

25. The method of claim 24 wherein at least a subset of the sensors measure stresses on the surface of the device.

26. The method of claim 23 wherein said step of analyzing the measurements includes comparing the most recent of the measurements representing initial parameters at a most recent instant of time with at least one set of the measurements representing the same parameters at an earlier instant of time.

27. The method of claim 23 wherein said step of analyzing the measurements determines a likely value for at least one derived parameter selected from the group of:
direction to nearest fluid system wall;
relative position of the device with respect to the cross-section of the fluid system;
angular velocity of the device;
linear velocity of the device; and
a dimension of the fluid system.

28. The method of claim 23 wherein said step of analyzing the measurements includes characterizing at least one feature of fluid system geometry.

29. The method of claim 28 wherein said step of analyzing the measurements uses evaluation parameters stored in a memory on the device when performing said step of characterizing at least one feature of fluid system geometry.

30. The method of claim 28 further comprising the steps of:
comparing the characterized feature(s) to criteria identifying one or more prescribed features to provide a degree of certainty that the characterized feature(s) match the one or more prescribed features of interest; and
directing the device to take a prescribed action based on the degree of certainty with which the characterized feature(s) match the feature(s) of interest.

31. The method of claim 30 wherein the prescribed action includes at least one step selected from the group of:
where the device has a locomotive capability and the characterized feature is a branch or a merger, activating said locomotive capability to move into a select one of multiple branches;
where the device has a locomotive capability, activating said locomotive capability to move to a wall of the fluid system;
releasing a stored chemical;
taking in a chemical present in the fluid environment;
transmitting a signal from the device to remote receiver;
saving a record of the characterized feature location; and
changing operating parameters of the device.

32. The method of claim 31 wherein the prescribed action includes moving to a wall of the fluid system, and wherein the prescribed action further includes moving to whichever wall is nearest.

33. The method of claim 30 wherein the prescribed action includes transmitting a signal to a remote receiver, and wherein said step of transmitting further comprises at least one action selected from the group of:
transmitting location data for the characterized feature;
transmitting data that further characterizes the feature; and
transmitting identifying information for the device.

34. The method of claim 33 wherein the remote receiver is located on another device operating within the fluid system, which is provided with instructions to perform a prescribed action responsive to receiving the transmitted signal.

35. The method of claim 30 for use in situations where at least a partial map of the fluid system is available, wherein said step of comparing the characterized feature(s) compares the characterized feature(s) to specific features located on the map.

36. The method of claim 30 wherein the prescribed feature is not defined with respect to its location in the fluid system.

37. The method of claim 36 wherein the prescribed feature is at least one feature selected from the group of:
   a branch point;
   a merger point;
   a degree of curvature above a defined minimum;
   an apparent discontinuity in any nearby wall of the fluid system; and
   another object in the fluid flow.

38. The method of claim 23 wherein the device has a locomotive capability and said step of analyzing the measurements includes directing the device to vary the operation of its locomotive capacity and compensating for the action of said locomotive capability.

39. A method for mapping a fluid system comprising:
   taking measurements using at least one device as the device(s) travels within the fluid system, the measurements providing representations of parameters of the fluid flow at instants of time when the measurements are taken;
   operating on the measurements to characterize at least one geometry feature of the fluid system at the time when a particular set of measurements are taken with a prescribed degree of confidence;
   storing geometry characterizations in a memory;
   comparing the geometry feature characterizations in memory to each other to identify overlaps and matches; and
   where a match or overlap is identified, placing matching or overlapping features characterized into relative position with respect to each other to form a map of the fluid system.

40. The method of claim 39 wherein said memory is at least partially located on said at least one device.

41. The method of claim 40 wherein said step of characterizing at least one geometry feature is performed using classification parameters stored in said memory on said at least one device.

42. The method of claim 39 wherein said step of taking measurements using at least one device comprises measuring at least one initial parameter of the fluid using sensors distributed with respect to the device to provide the representations of parameters of the fluid flow at instants of time when the measurements are taken; and
   further wherein said step of operating on the measurements to characterize at least one geometry feature of the fluid system further comprises the steps of:
      analyzing the measurements using a quasi-static model of fluid forces to determine a likely value for at least one value for a derived parameter selected from the group of:
         parameters defining the position of the device relative to the fluid system,
         parameters defining the character of the motion of the device relative to the fluid system,
         parameters relating to the character of the fluid flow, and
         parameters defining the geometry of the fluid system,
      characterizing at least one feature of fluid system geometry, and
      comparing the characterized feature(s) to criteria identifying one or more prescribed features to provide a degree of certainty that the characterized feature(s) match the one or more prescribed features of interest.

* * * * *